United States Patent
Hareyama et al.

(10) Patent No.: US 6,740,085 B2
(45) Date of Patent: May 25, 2004

(54) HEATING TREATMENT SYSTEM

(75) Inventors: Norihiko Hareyama, Hachioji (JP); Taisuke Sato, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/014,698

(22) Filed: Nov. 13, 2001

(65) Prior Publication Data

US 2002/0082593 A1 Jun. 27, 2002

(30) Foreign Application Priority Data

Nov. 16, 2000 (JP) ........................................ 2000-350116
Feb. 14, 2001 (JP) ........................................ 2001-037357

(51) Int. Cl.[7] .............................................. A61B 18/18
(52) U.S. Cl. ........................................... 606/51; 606/50
(58) Field of Search ................................. 606/50, 51, 52, 606/41, 49

(56) References Cited

U.S. PATENT DOCUMENTS

| | | | | |
|---|---|---|---|---|
| 3,826,263 A | * | 7/1974 | Cage et al. | |
| RE30,190 E | * | 1/1980 | Shaw | |
| 4,232,676 A | * | 11/1980 | Herczog | 128/303.14 |
| RE31,723 E | * | 11/1984 | Shaw | |
| 4,532,924 A | * | 8/1985 | Auth et al. | 128/303.17 |
| 5,383,874 A | * | 1/1995 | Jackson et al. | 606/1 |
| 5,496,312 A | * | 3/1996 | Klicek | 606/34 |
| 6,083,223 A | * | 7/2000 | Baker | 606/52 |
| 6,165,169 A | * | 12/2000 | Panescu et al. | 606/1 |
| 6,210,411 B1 | * | 4/2001 | Hofmann et al. | 606/52 |
| 6,214,003 B1 | * | 4/2001 | Morgan et al. | 606/50 |
| 6,228,082 B1 | * | 5/2001 | Baker et al. | 606/49 |
| 6,277,116 B1 | * | 8/2001 | Utely et al. | 606/42 |
| 6,277,117 B1 | * | 8/2001 | Tetzlaff et al. | 606/48 |
| 6,334,861 B1 | * | 1/2002 | Chandler et al. | 606/50 |
| 6,383,183 B1 | * | 5/2002 | Sekino et al. | 606/34 |
| 6,398,782 B1 | * | 6/2002 | Pecor et al. | 606/50 |
| H2037 H | * | 7/2002 | Yates et al. | 606/51 |

FOREIGN PATENT DOCUMENTS

| | | | |
|---|---|---|---|
| JP | 53-9031 | * | 4/1978 |
| JP | 2578250 | * | 11/1996 |
| JP | 2000-250 | * | 1/2000 |

* cited by examiner

*Primary Examiner*—Roy D. Gibson
*Assistant Examiner*—Aaron Roane
(74) *Attorney, Agent, or Firm*—Scully, Scott, Murphy & Presser

(57) ABSTRACT

A heating treatment system consists mainly of coagulating/incising forceps in which a plurality of heating elements are incorporated, and a main unit that feeds power to the heating elements incorporated in the coagulating/incising forceps and that drives and controls the heating elements. The main unit can be connected to coagulating/incising forceps in which up to four heating elements are incorporated. The main unit includes element temperature measurement/output control units and temperature setting units which are associated with four channels allocated to the heating elements. A control unit controls the element temperature measurement/output control units and temperature setting units. The control unit judges the type of connected forceps by referencing data stored in advance in a memory using information of the type of forceps received from the coagulating/incising forceps, and controls power feed to the heating elements.

20 Claims, 30 Drawing Sheets

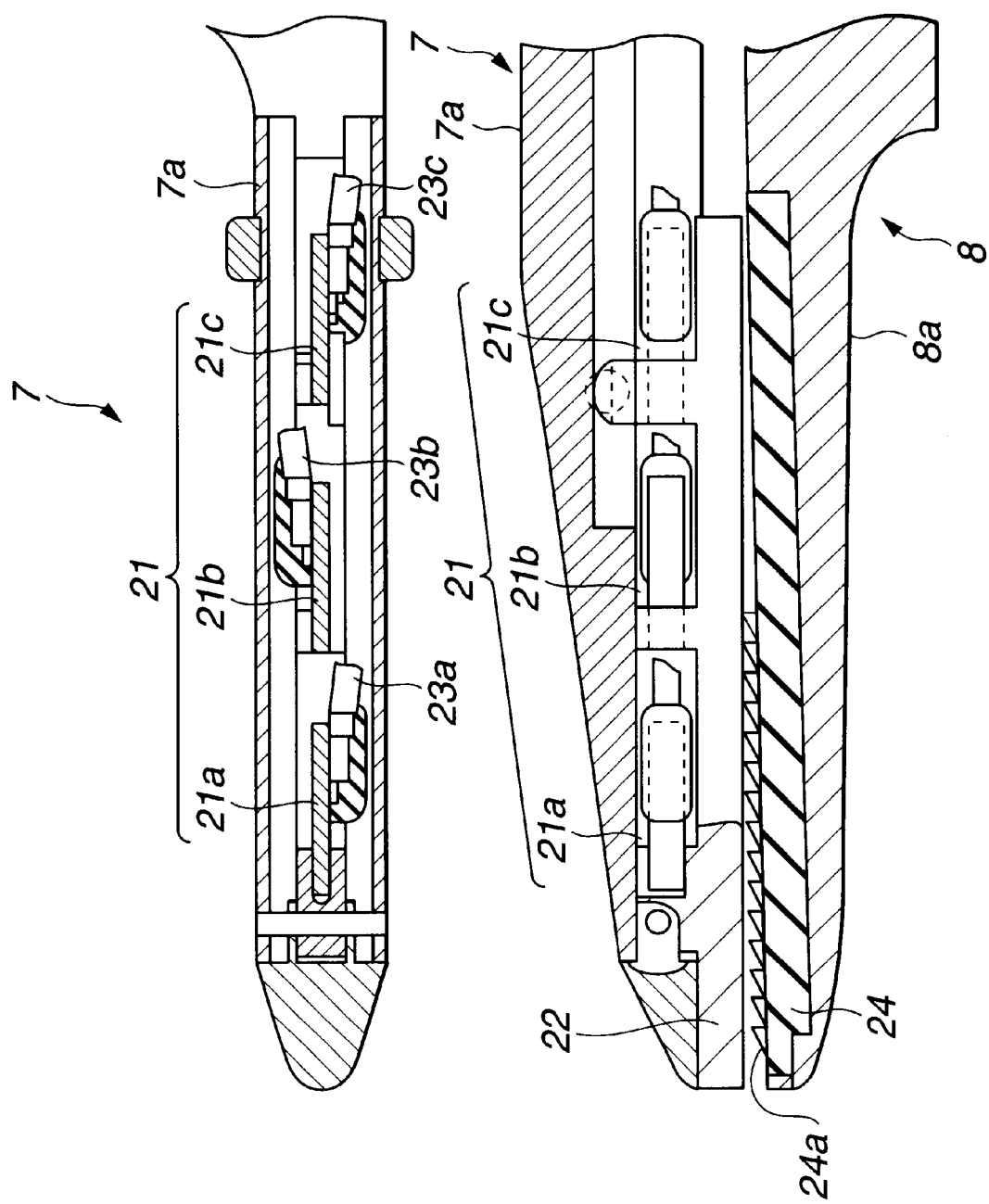

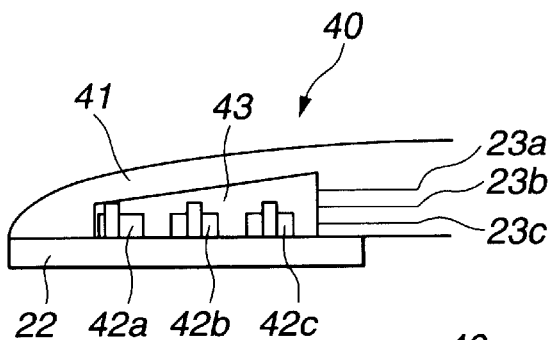
FIG.9A
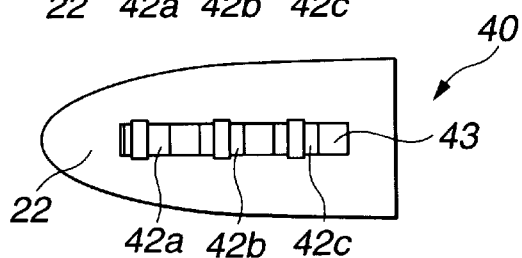
FIG.9B
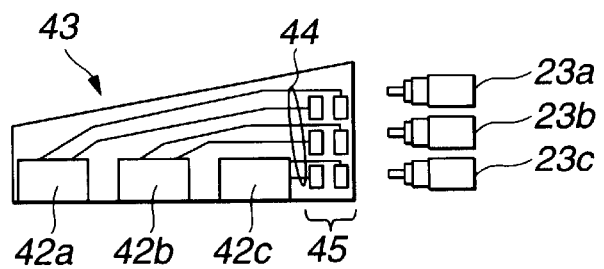
FIG.9C
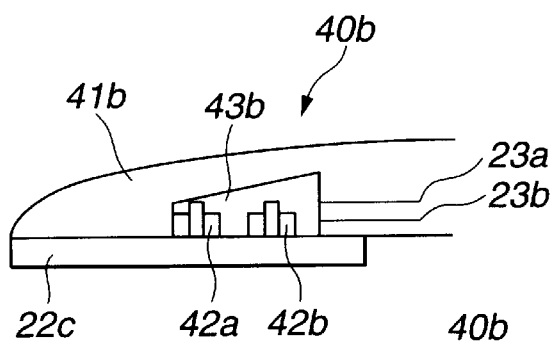
FIG.10A
FIG.10B
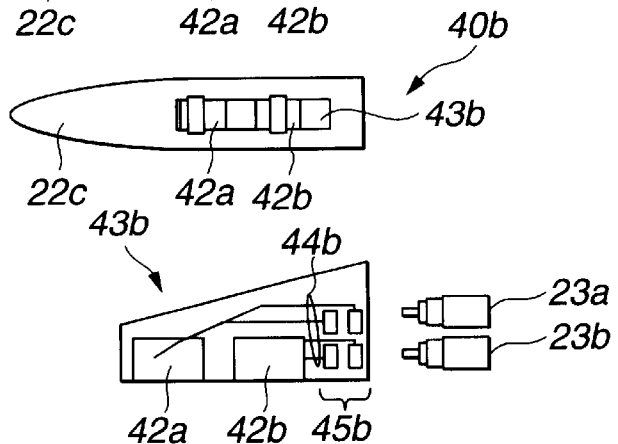
FIG.10C

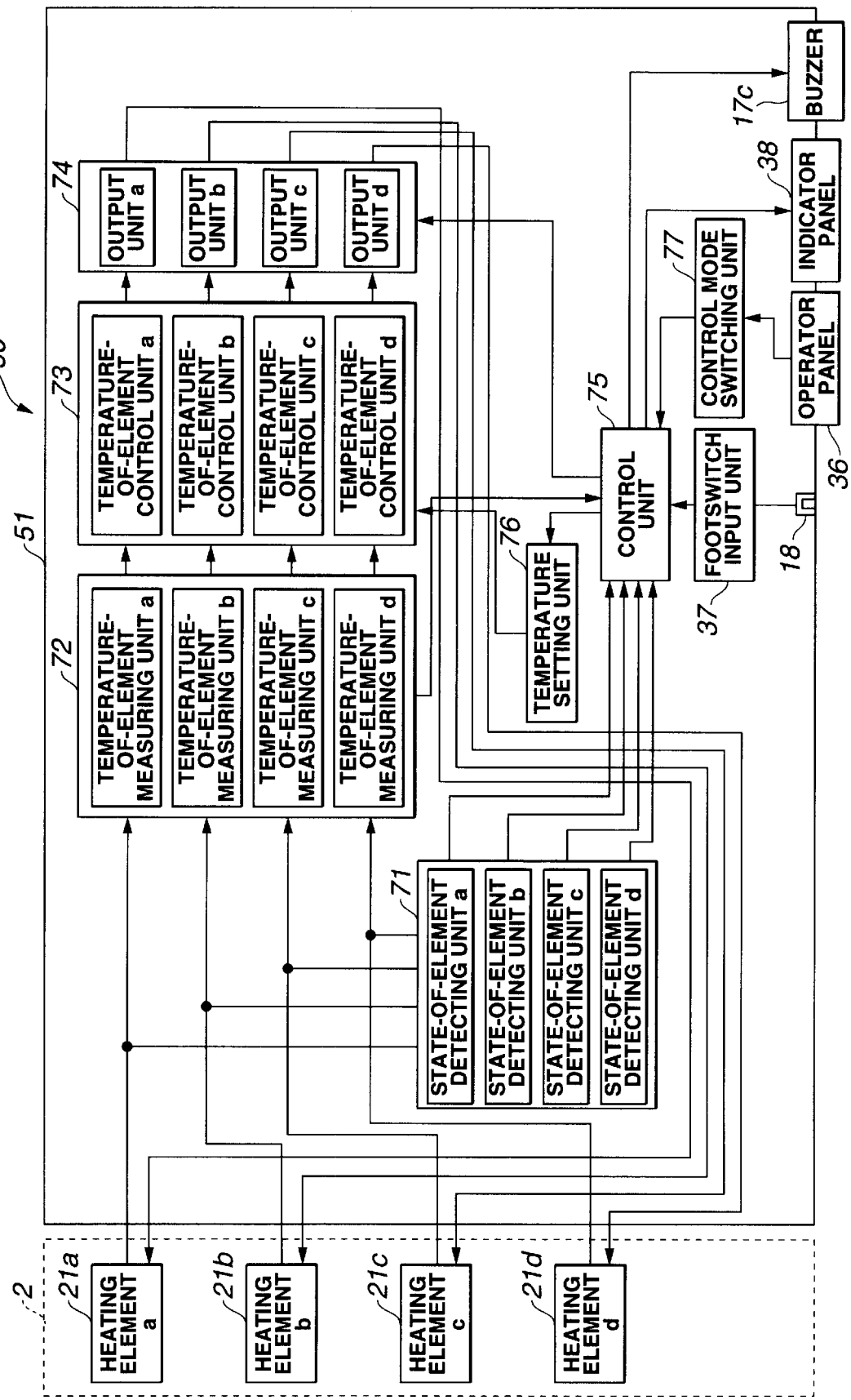

HEATING TREATMENT SYSTEM

This application claims benefit of Japanese Application Nos. 2000-350116 filed on Nov. 16, 2000 and 2001-037357 filed on Feb. 14, 2001, the contents of which are incorporated by this reference.

BACKGROUND OF THE INVENTION

1. Field of the Invention

The present invention relates to a heating treatment system, or more particularly, a heating treatment system that heats an affected part for treatment.

2. Description of the Related Art

In general, heating treatment systems are used to incise an affected part, coagulate or arrest bleeding during a surgical operation or an internal operation. The heating treatment system includes a treatment unit in which a heating means for heating an affected part or a lesion is incorporated. Heat dissipated from the heating means in the treatment unit is applied to the affected part for the purpose of incision, coagulation, hemostasis, or any other treatment.

As one type of heating treatment system, a heating treatment system having a treatment unit, which includes a plurality of heater segments, as a heating means has been proposed as described, for example, in Japanese Examined Patent Application Publication No. 53-9031.

The treatment unit applies heat, which is dissipated from the plurality of heater segments that is set to the same temperature, to an affected part for the purpose of treatment.

However, the heating treatment system described in the Japanese Examined Patent Application Publication No. 53-9031 heats the plurality of heater segments up to the same temperature. When the heater segments are adapted to a treatment unit having a different shape, a distribution of temperature values in the treatment unit may become uneven.

SUMMARY OF THE INVENTION

The present invention attempts to break through the foregoing situation. An object of the present invention is to provide a heating treatment system capable of producing an appropriate distribution of temperature values in any of various shapes of treatment unit, and achieving treatment on a stable basis.

A heating treatment system for treating a living tissue according to the present invention consists mainly of a therapeutic instrument, a temperature level switch, a temperature-of-heating element setting circuit, and a plurality of output circuits. The therapeutic instrument includes a plurality of heating elements that dissipate heat in proportion to fed driving power, and a heat transfer plate coupled to the heating element. The temperature level switch is used to input an instruction for adjusting the temperature of the heat transfer plate. The temperature-of-heating element setting circuit sets temperature values, up to which the heating elements are heated, in response to the instruction given using the temperature level switch. The plurality of output circuits feed driving power to the heating elements according to the plurality of temperature values up to which the heating elements are heated and which are set by the temperature-of-heating element setting circuit.

The above and other objects, features and advantages of the invention will become more clearly understood from the following description referring to the accompanying drawings.

BRIEF DESCRIPTION OF THE DRAWINGS

FIG. 7A is a top sectional view showing the upper side of the heating treatment member of the coagulating/incising forceps shown in FIG. 3 in the vertical direction;

FIG. 7B is a side sectional view showing the lateral side of the treatment unit of the coagulating/incising forceps shown in FIG. 7A in the horizontal direction;

FIG. 9A is a schematic diagram showing a heating treatment member of coagulating/incising forceps included in a heating treatment system in accordance with a second embodiment of the present invention;

FIG. 9B is a schematic diagram showing the upper side of the heating treatment system shown in FIG. 9A in the vertical direction;

FIG. 9C is an enlarged view of heater block included in the heating treatment member shown in FIG. 9A;

FIG. 10A is a schematic diagram showing a variant of the coagulating/incising forceps shown in FIG. 9A and the lateral side of a heating treatment member in the horizontal direction;

FIG. 10B is a schematic diagram showing the upper side of the heating treatment member shown in FIG. 10A in the vertical direction;

FIG. 10C is an enlarged view showing heater block included in the coagulating/incising forceps shown in FIG. 10A;

FIG. 15 is a circuit block diagram for explaining the heating treatment system in accordance with the third embodiment of the present invention;

DESCRIPTION OF THE PREFERRED EMBODIMENTS

Figure 1:
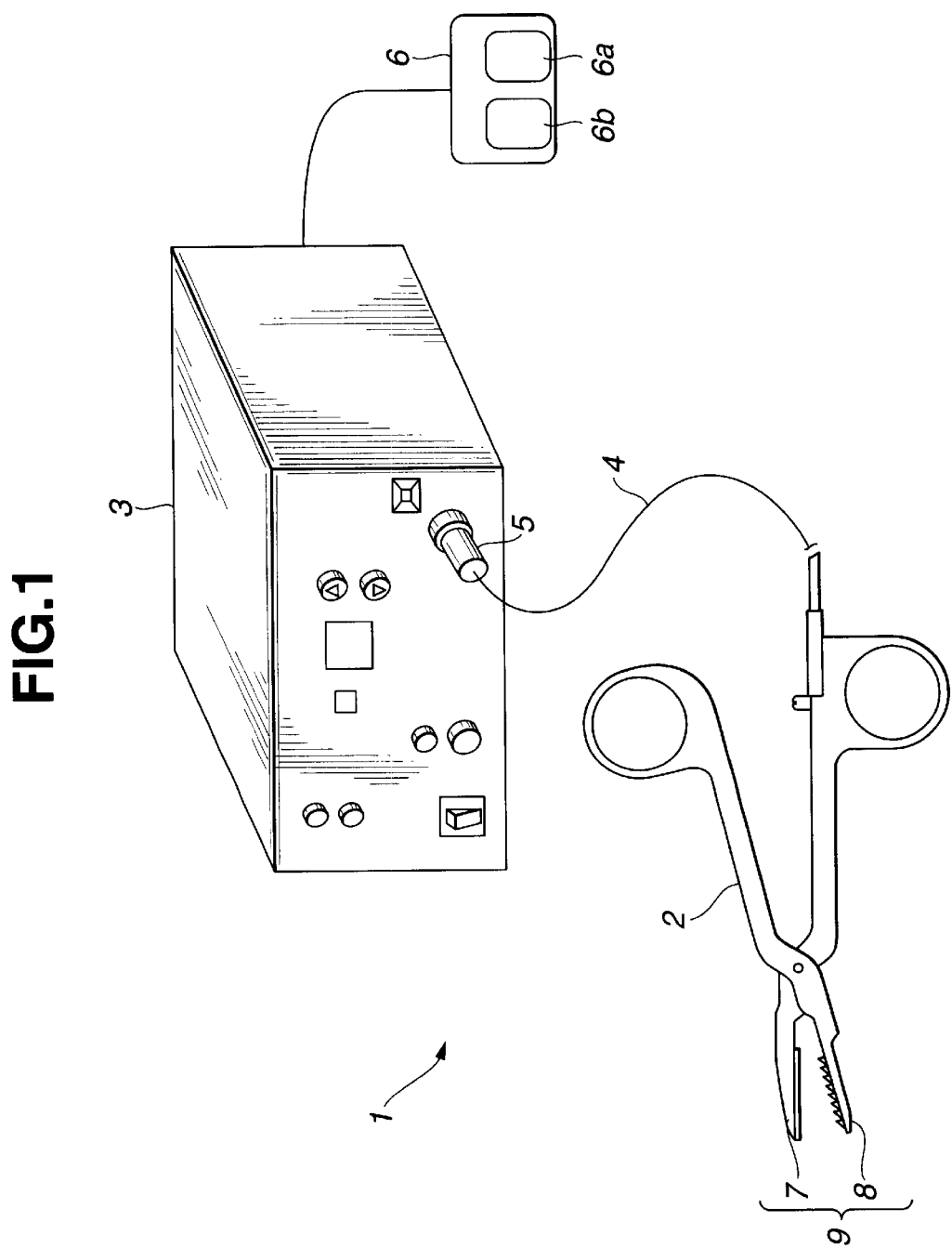
FIG. 1 shows the overall configuration of a heating treatment system in accordance with a first embodiment of the present invention.

Referring to the drawings, embodiments of the present invention will be described below.

(First Embodiment)

Figure 2A:
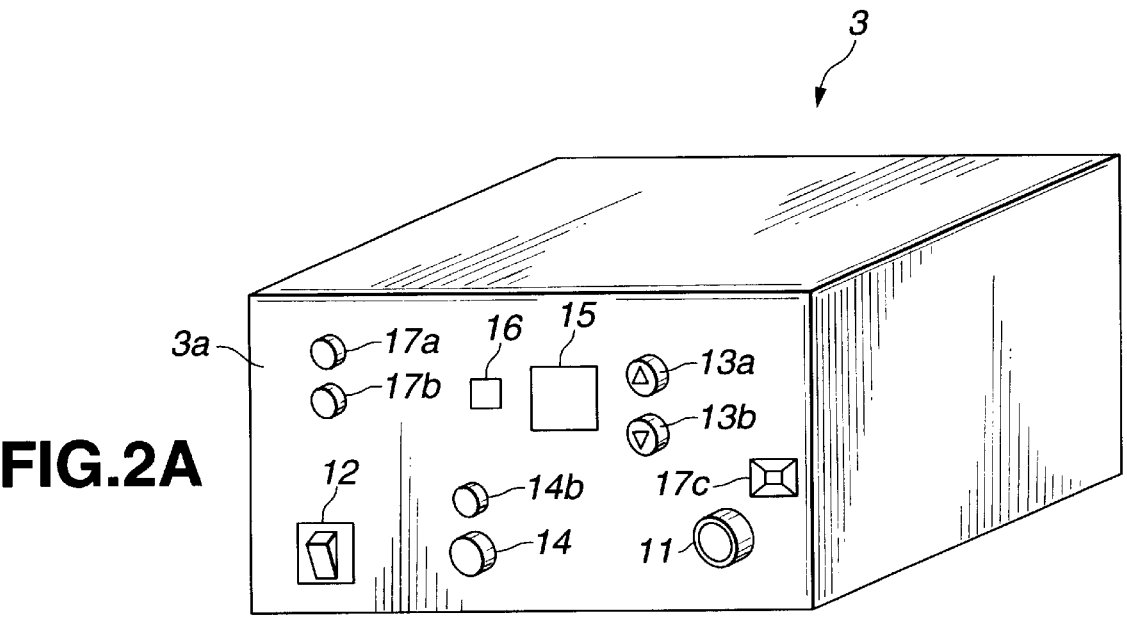
FIG. 2A is a perspective view showing the appearance of a main unit included in the heating treatment system shown in FIG. 1.
Figure 2B:
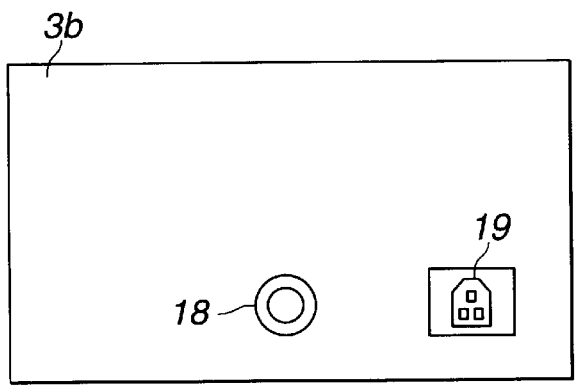
FIG. 2B is a rear view showing the back of the main unit included in the heating treatment system shown in FIG. 1.
Figure 3:
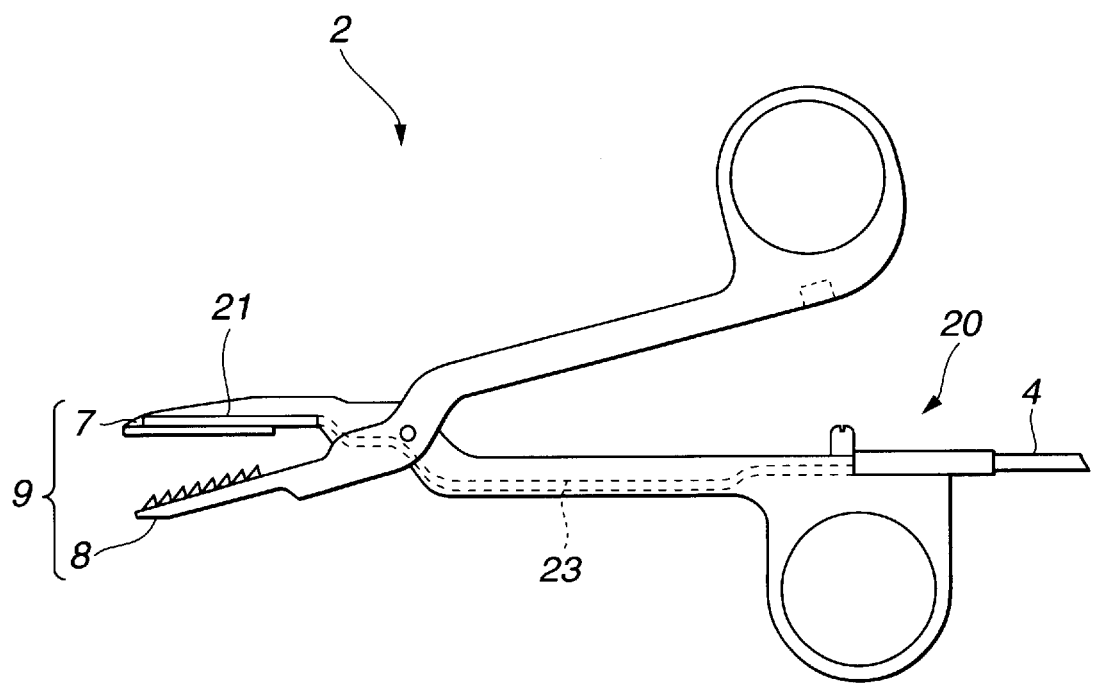
FIG. 3 is an explanatory diagram showing coagulating/incising forceps included in the heating treatment system shown in FIG. 1.
Figure 8:
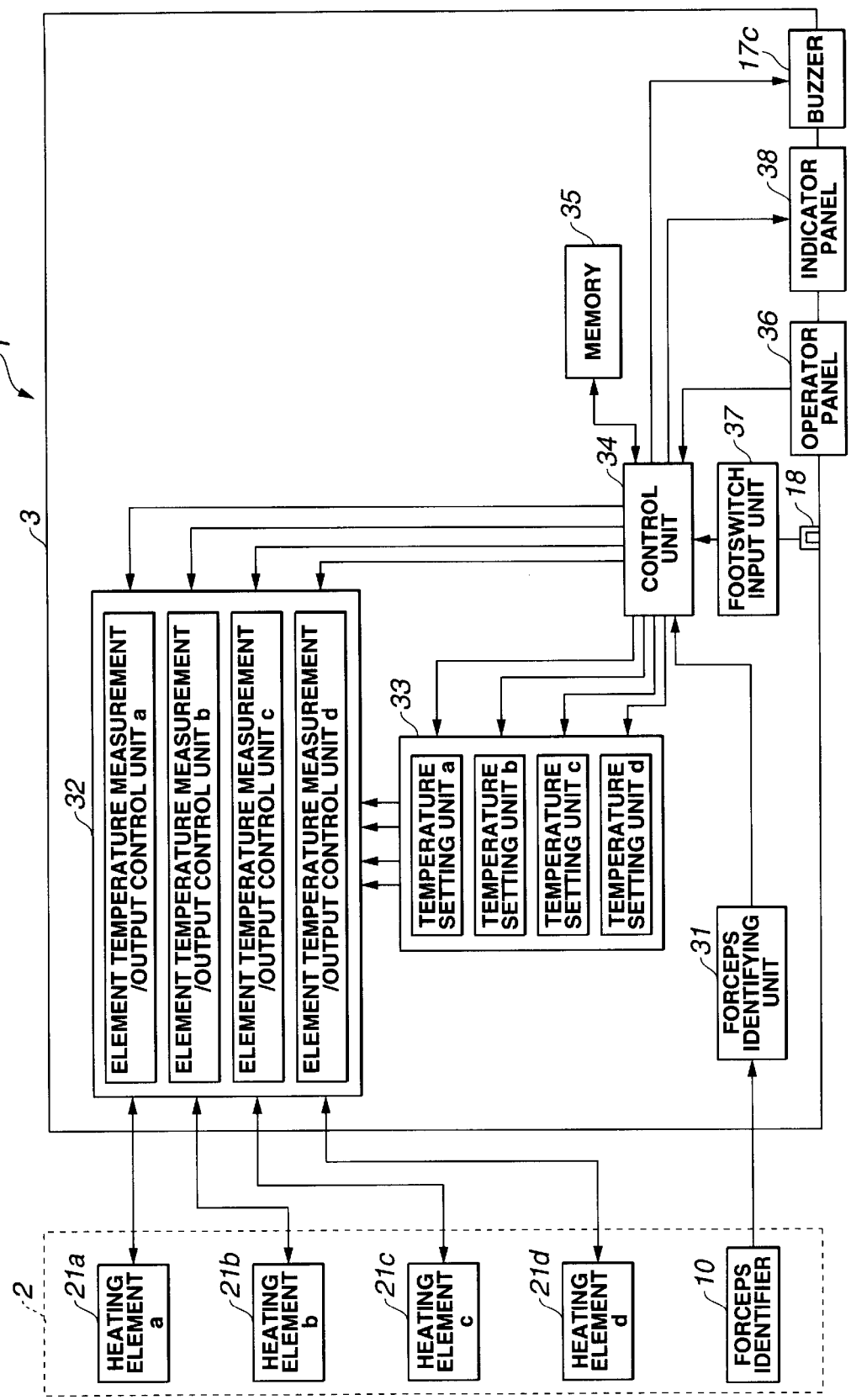
FIG. 8 is a circuit block diagram for use in explaining the heating treatment system in accordance with the first embodiment of the present invention.

FIG. 1 to FIG. 8 are concerned with a first embodiment of the present invention. FIG. 1 shows the overall configuration of a heating treatment system in accordance with the first embodiment of the present invention. FIG. 2A and FIG. 2B show the appearance of a main unit of the heating treatment system shown in FIG. 1. FIG. 2A shows the appearance of the main unit seen from the front panel thereof. FIG. 2B shows a back panel of the main unit. FIG. 3 is an explanatory diagram showing coagulating/incising forceps included in the heating treatment system shown in FIG. 1. FIG. 4A and FIG. 4B are explanatory diagrams showing a heating treatment member of the coagulating/incising forceps shown in FIG. 3. FIG. 4A is a schematic diagram showing the lateral side of the heating treatment member in the horizontal direction. FIG. 4B is a schematic diagram showing the upper side of the heating treatment member shown in FIG. 4A in the vertical direction. FIG. 5A and FIG. 5B are explanatory diagrams showing a variant of the coagulating/incising forceps shown in FIG. 4A. FIG. 5A is a schematic diagram showing the lateral side of the heating treatment member in the horizontal direction. FIG. 5B is a schematic diagram showing the upper side of the heating treatment member shown in FIG. 5A in the vertical direction. FIG. 6A and FIG. 6B are explanatory diagrams showing another variant of the coagulating/incising forceps shown in FIG. 4A. FIG. 6A is a schematic diagram showing the lateral side of the heating treatment member in the horizontal direction. FIG. 6B is a schematic diagram showing the upper side of the heating treatment member shown in FIG. 6A in the vertical direction. FIG. 7A and FIG. 7B are explanatory diagrams showing the treatment unit of the coagulating/incising forceps shown in FIG. 3. FIG. 7A is a top sectional view showing the upper side of the heating treatment member in the vertical direction. FIG. 7B is a side sectional view showing the lateral side of the treatment unit of the coagulating/incising forceps in the horizontal direction. FIG. 8 is a circuit block diagram for explaining the heating treatment system in accordance with the first embodiment of the present invention.

As shown in FIG. 1, a heating treatment system 1 in accordance with the present embodiment consists mainly of coagulating/incising forceps 2 and a main unit 3. The coagulating/incising forceps 2 are a therapeutic instrument having heating elements, which will be described later, incorporated therein. The coagulating/incising forceps 2 are connected to the main unit 3 so that it can be disconnected freely. The main unit 3 feeds power to the heating elements incorporated in the coagulating/incising forceps 2, and thus driving and controlling the coagulating/incising forceps 2. A footswitch 6 can be connected to the main unit 3. The footswitch 6 includes two switches of a maximum temperature level output switch 6a and a designated temperature level output switch 6b which serve as an input means.

The coagulating/incising forceps 2 has a main unit connector 5 attached to the rear end of a connection cable 4 extending from the rear end thereof. The main unit connector 5 is coupled to the main unit 3 so that it can be uncoupled freely The coagulating/incising forceps 2 include a treatment unit 9 that consists of a heating treatment member 7 and an elastic receptor 8 and that clamps a living tissue. A plurality of heating elements is incorporated in the heating treatment member 7, and the elastic receptor 8 can approach to or recede from the heating treatment member 7.

The heating treatment member 7 and elastic receptor 8 of the treatment unit 9 clamp a living tissue. When the heating treatment member 7 dissipates heat while being heated with electricity conducted from the main unit 3, the clamped living tissue is coagulated and incised. Moreover, the number of heating elements varies depending on the type of forceps that are suitable for a purpose of treatment. A forceps identifier 10 (see FIG. 8) that indicates the type of forceps is incorporated in the main unit connector 5. The forceps identifier 10 is, for example, an electrically resistive element.

As shown in FIG. 2A and FIG. 2B, the main unit 3 has a front panel 3a and back panel 3b.

As shown in FIG. 2A, the front panel 3a has a connector receptacle 11 to which the main unit connector 5 attached to the cable extending from the coagulating/incising forceps 2 is joined so that the main unit connector 5 can be disjoined freely. Moreover, the front panel 3a has a power switch 12, a temperature level up switch 13a and a temperature level down switch 13b, and a standby switch 14. The power switch 12 is used to turn on or off the power supply. The temperature level up switch 13a and temperature level down switch 13b are used to designate any of temperature levels 1 to 5 based on which the heating treatment member 7 of the coagulating/incising forceps 2 is heated. The standby switch 14 is used to change a standby state into an output enabled state or vice versa.

Moreover, the front panel 3a has a standby indicator LED 14b, a temperature level indicator LED 15, an output indicator LED 16, a forceps error indicator LED 17a, a power error indicator LED 17b, and a buzzer 17c. The standby indicator LED 14b is lit when the standby state is established and power feed is disabled. The temperature level indicator LED 15 indicates a temperature level designated using the temperature level up switch 13a and temperature level down switch 13b. The output indicator LED 16 indicates that electricity is being conducted to the heating elements incorporated in the coagulating/incising forceps 2. The forceps error indicator LED 17a is lit when the coagulating/incising forceps 2 become abnormal. The power error indicator LED 17b is lit when any internal circuit becomes abnormal. The buzzer 17c generates a warning sound.

As shown in FIG. 2B, the back panel 3b has a footswitch connector receptacle 18 and a power inlet 19. The coagulating/incising forceps 2 in which up to four heating elements is incorporated can be connected to the main unit 3 employed in the present embodiment.

Referring to FIG. 3, the coagulating/incising forceps 2 includes, as mentioned above, the treatment unit 9 composed of the heating treatment member 7 and elastic receptor 8. Moreover, the coagulating/incising forceps 2 has a handle pair 20 that is opened or closed in order to clamp a living tissue using the treatment unit 9. The connection cable 4 extends from the rear end of the handle pair 20.

Figure 4A:
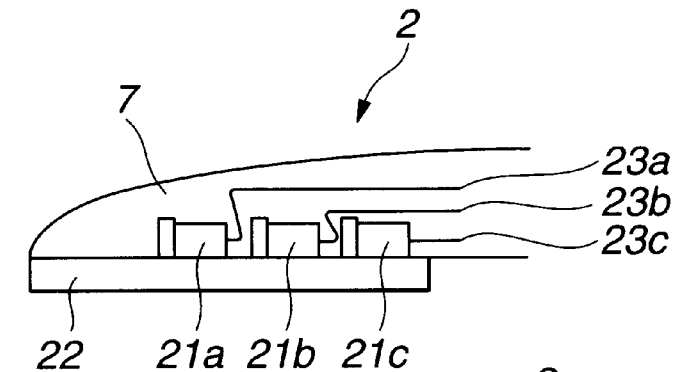
FIG. 4A is a schematic diagram showing the lateral side of a heating treatment member of the coagulating/incising forceps shown in FIG. 3 in the horizontal direction.
Figure 4B:
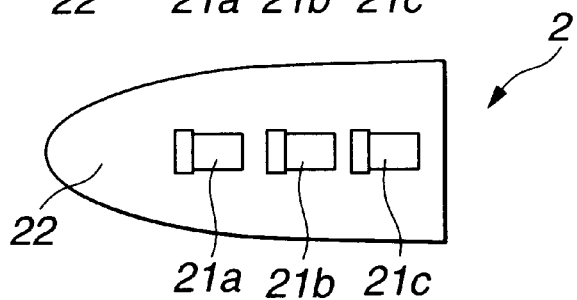
FIG. 4B is a schematic diagram showing the upper side of the heating treatment member shown in FIG. 4A in the vertical direction.

As shown in FIG. 4A and FIG. 4B, the heating treatment member 7 of the coagulating/incising forceps 2 has the plurality of heating elements 21, for example, three identical heating elements 21a, 21b, and 21c thermally coupled to one another and placed on a heat transfer plate 22.

Figure 5A:
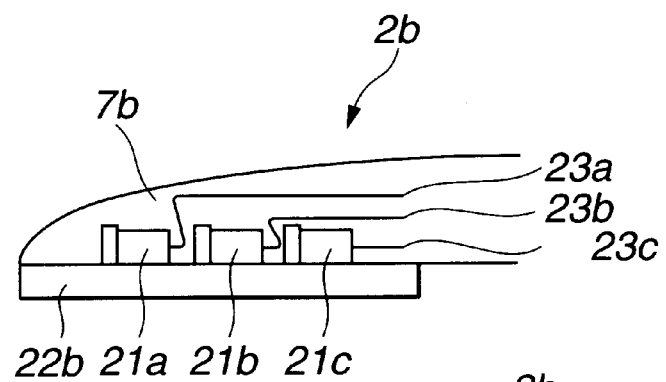
FIG. 5A is a schematic diagram showing a variant of the coagulating/incising forceps shown in FIG. 4A and the lateral side of the heating treatment member in the horizontal direction.

FIG. 5A to FIG. 6B show variants of the coagulating/incising forceps 2. A heating treatment member 7b of coagulating/incising forceps 2b shown in FIG. 5A and FIG. 5B is different from the heating treatment member 7 of the coagulating/incising forceps 2 described in conjunction with FIG. 4A and FIG. 4B in a point that the heating elements 21a, 21b, and 21c are juxtaposed near the distal end of the heating treatment member 7b. Moreover, a heat transfer plate 22b has a smaller width. A heating treatment member 7c of coagulating/incising forceps 2c shown in FIG. 6A and FIG. 6B has two heating elements 21a and 21b incorporated therein. The heating elements 21a and 21b are juxtaposed near the proximity end of a heat transfer plate 22c compared with the heating elements incorporated in the heating treatment member 7b of the coagulating/incising forceps 2. The width of the heat transfer plate 22c is smaller than that of the heat transfer plate 22b included in the heating treatment member 7b of the coagulating/incising forceps 2b shown in FIG. 5A and FIG. 5B.

According to the present embodiment, the temperatures to which the heating elements 21 are set are varied depending on the shape of forceps or the arrangement of the heating elements 21. This is intended to minimize uneven temperature occurring in the heating treatment member 22.

Next, the detailed structure of the treatment unit 9 composed of the heating treatment member 7 and elastic receptor 8 will be described below.

The heating treatment member 7 has, as shown in FIG. 7A and FIG. 7B, the heating elements 21 (21a to 21c) incorporated in a heating treatment member body 7a. Herein, the heating element is a thin-film resistor formed, for example, on a ceramic plate. One end of each of coaxial leads 23 (23a, 23b, and 23c) over which electricity is conducted is coupled to the heating elements 21 (21a to 21c). The other end of each of the leads 23 is spliced to the connection cable 4 and coupled to a pin, which is not shown, of the main unit connector 5.

As mentioned above, the heating elements 21 (21a to 21c) are thermally coupled to the heat transfer plate 22. Heat dissipated from the heating elements 21 (21a to 21c) is propagated to the heat transfer plate 22.

The elastic receptor 8 is formed by fixing an elastic member 24, which has a sawtooth 24a that cooperates with the heat transfer plate 22 of the heating treatment member 7 in clamping a living tissue, to an elastic receptor body 8a. By closing the handle pair 20, the elastic receptor 8 approaches to the heating treatment member 7. Consequently, the heat transfer plate 22 of the heating treatment member 7 and the sawtooth 24a of the elastic receptor 8 elastically clamp a living tissue. The living tissue sandwiched between the heat transfer plate 22 and elastic member 24 is coagulated or incised with heat transferred from the heat transfer plate 22.

As shown in FIG. 8, when the main unit connector 5 of the coagulating/incising forceps 2 is coupled to the main unit 3, a forceps identifying unit 31 receives information of the type of forceps sent from the forceps identifier 10 incorporated in the main unit connector 5.

When the forceps identifier 10 is realized with an electrically resistive element, the forceps identifying unit 31 measures the resistance of the resistive element so as to identify the type of forceps. The type of forceps is a category to which the structure of forceps belongs when being judged in terms of the number of incorporated heating elements 21, the arrangement thereof, and the shape of the heat transfer plate 22.

The main unit 3 can be connected to a coagulating/incising forceps that includes, for example, up to four heating elements 21 (21a, 21b, 21c, and 21d). The main unit 3 includes element temperature measurement/output control units 32 (32a to 32d) and temperature setting units 33 (33a to 33d) that are associated with four channels allocated to the heating elements 21 (21a, 21b, 21c, and 21d). The element temperature measurement/output control units 32 (32a to 32d) and temperature setting units 33 (33a to 33d) are controlled by a control unit 34. Each of the temperature setting units 33 is a circuit for setting a temperature value to which an associated heating element is heated. When the number of heating elements 21 incorporated in the coagulating/incising forceps 2 is three or less, the heating elements are allocated in order to the channels.

The element temperature measurement/output control unit 32 (any of 32a to 32d) calculates the temperature of an associated heating element from the resistance value exhibited by the heating element 21 (any of 21a to 21d). Any of the element temperature measurement/output control units 32 controls power feed to the heating element 21 (any of 21a to 21d) so that the heating element will be retained at the temperature value set by the temperature setting unit 33 (any of 33a to 33d).

The control unit 34 identifies the type of connected forceps by referencing data pre-stored in a memory 35 according to the information of the type of forceps transferred from the forceps identifying unit 31. The control unit 34 changes the temperature values set by the temperature setting units 33 (33a to 33d) by acquiring the set values pre-stored in the memory 35 according to the judged type of forceps. Moreover, the control unit 34 controls power feed from the element temperature measurement/output control units 32 (32a to 32d). The set values pre-stored in the memory 35 are defined based on the number of heating elements 21, the arrangement thereof, and the shape of the heat transfer plate 22.

Moreover, the control unit 34 sets the temperature setting units 33 (33a to 33d) to a temperature level that is designated using an operator panel 36 or to a maximum temperature level or to designated temperature level that is transmitted from the footswitch 6 via a footswitch input unit 37. What is referred to as the operator panel 36 is a generic term for various switches including the temperature level up switch 13a exposed on the aforesaid front panel 3a. Moreover, an indicator panel 38 is a generic term for various indicator LEDs exposed on the front panel 3a. Moreover, when an abnormality of a circuit is detected, the control unit 34 lights the forceps error indicator LED 17a and sounds the buzzer 17c.

Referring to FIG. 4A to FIG. 6B, operation to be exerted by the heating treatment system 1 having the foregoing components will be described in conjunction with Table 1 to Table 3. To begin with, a description will be made of a case where the coagulating/incising forceps 2 including the heating treatment member 7 described with reference to FIG. 4A and FIG. 4B are connected to the main unit.

The power switch 12 is turned on in order to activate the whole heating treatment system 1.

When the coagulating/incising forceps 2 is connected to the main unit 3, the forceps identifying unit 31 receives information concerning the type of forceps from the forceps identifier 10. The forceps identifying unit 31 duly identifies the type of coagulating/incising forceps 2, and transmits the information of the identified type of forceps to the control unit 34.

The control unit 34 identifies the type of connected forceps as the type including the heating treatment member 7 described in conjunction with FIG. 4 by referencing the data stored in the memory 35 according to the information concerning the type of forceps received from the forceps identifying unit 31.

The control unit 34 reads the numerical information of the heating elements 21, references a set temperature table, and thus acquires set values concerning the identified coagulating/incising forceps 2. What is referred to as the set temperature table is a listing of temperature values which are associated with designated temperature levels and to which the heating elements 21 are set. The designated temperature levels include five levels ranging from, for example, as listed in Table 1, level 1 to level 5.

TABLE 1

Temperature to which each heating element is set [° C.]

| Designated temperature level | Heating element 1 | Heating element 2 | Heating element 3 | Heating element 4 |
| --- | --- | --- | --- | --- |
| 1 | 180 | 160 | 170 | NC |
| 2 | 190 | 170 | 180 | NC |
| 3 | 200 | 180 | 190 | NC |
| 4 | 210 | 190 | 200 | NC |
| 5 | 220 | 200 | 210 | NC |

The set temperature table of Table 1 lists set temperature values so that the heating element 21a will be heated to the highest temperature, the heating element 21c will be heated to the second highest temperature, and the heating element 21b will be heated to the lowest temperature.

This is intended to minimize uneven temperature occurring on the surface of the heat transfer plate 22 that comes into contact with a living tissue. For this reason, the heating element 21a responsible for heating the distal part of the heat transfer plate 22 is set to the highest temperature, the heating element 21c responsible for heating a relatively large width is set to the second highest temperature, and the heating element 21b interposed between the two heating elements 21a and 21c and incurring the smallest load is set to the lowest temperature.

Herein, if the standby switch 14 is pressed, the control unit 34 discontinues the standby state and puts out the standby indicator LED 14b. Consequently, an output enabled state is established in order to enable power feed. When the footswitch 6 is stepped on, electricity is conducted to the heating elements 21 incorporated in the coagulating/incising forceps 2. If the standby switch 14 is pressed again, the control unit 34 changes the output enabled state to the standby state, and lights the standby indicator LED 14b. Consequently, the output enabled state is discontinued.

If the maximum temperature level output switch 6a of the footswitch 6 is stepped on, the control unit 34 instructs the temperature setting units 33 (33a to 33d) associated with the heating elements to set the temperature values associated with the temperature level of level 5 for the heating elements irrespective of what temperature level has been designated. Specifically, 220° C. is set for the heating element 21a, 200° C. is set for the heating element 21b, and 210° C. is set for the heating element 21c. The control unit 34 brings the element temperature measurement/output control units 32a to 32c to an output control state. At this time, the control unit 34 lights the output indicator LED 14 and sounds the buzzer continuously.

The element temperature measurement/output control units 32a to 32c control power feed. In other words, the element temperature measurement/output control units 32a to 32c feed driving power to the heating elements 21a to 21c while measuring the temperatures of the heating elements so that the heating elements will be heated to the set temperature values. The temperature values are set in association with the temperature level of level 5 by the temperature setting units 33a to 33c.

If the designated temperature level output switch 6b of the footswitch 6 is stepped on, the control unit 34 instructs the temperature setting units 33 (33a to 33d) associated with the heating elements to set the temperature values associated with a designated temperature level for the heating elements. The element temperature measurement/output control units 32a to 32c are brought to an output control state, and power feed is started. At this time, the control unit 34 flickers the output indicator LED 14 and sounds the buzzer intermittently.

For example, if the temperature level of level 3 is designated, 200° C. is set for the heating element 21a, 180° C. is set for the heating element 21b, and 190° C. is set for the heating element 21c. Power feed is then started. Consequently, compared with when power is fed with the same temperature value set for all the heating elements 21 (21a to 21c), uneven temperature occurring on the surface of the heat transfer plate 22 that comes into contact with a living tissue can be minimized and made almost even.

Figure 5B:
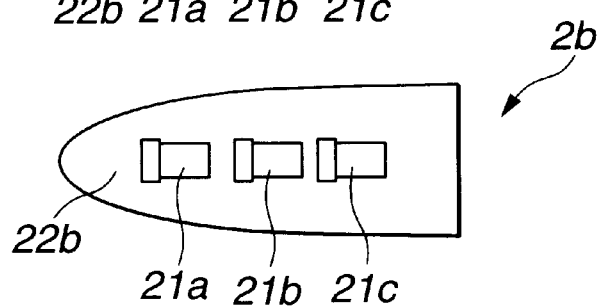
FIG. 5B is a schematic diagram showing the heating treatment member shown in FIG. 5A and the upper side of the member in the vertical direction.

Next, a description will be made of a case where the coagulating/incising forceps 2b having the heating treatment member 7b described in conjunction with FIG. 5A and FIG. 5B are connected to the main unit 3.

Similarly to when the coagulating/incising forceps 2 having the heating treatment member 7 is connected to the main unit 3, when the coagulating/incising forceps 2b is connected to the main unit 3, the forceps identifying unit 31 identifies the type of forceps according to information concerning the type of forceps received from the forceps identifier 10. The forceps identifying unit 31 then transmits the information of the identified type of forceps to the control unit 34.

The control unit 34 identifies the type of connected forceps as the coagulating/incising forceps 2b having the heating treatment member 7b described in conjunction with FIG. 5A and FIG. 5B. The control unit 34 then reads numerical information concerning the heating elements 21 and a set temperature table, which are relevant to the coagulating/incising forceps 2b, from the memory 35.

TABLE 2

Temperature to which each heating element is set [° C.]

| Designated temperature level | Heating element 1 | Heating element 2 | Heating element 3 | Heating element 4 |
|---|---|---|---|---|
| 1 | 170 | 170 | 180 | NC |
| 2 | 180 | 180 | 190 | NC |
| 3 | 190 | 190 | 200 | NC |
| 4 | 200 | 200 | 210 | NC |
| 5 | 210 | 210 | 220 | NC |

The set temperature table of Table 2 lists temperature values so that the heating element 21c responsible for heating a wide portion of the heat transfer plate 22b will be heated to the highest temperature, and the remaining heating elements 21a and 21b will be heated to the same temperature. This is intended to minimize uneven temperature occurring on the surface of the heat transfer plate 22b that comes into contact with a living tissue.

Herein, if the standby switch 14 is pressed, the control unit 34 discontinues the standby state, puts out the standby indicator LED 14b, and thus establishes an output enabled state. If the maximum temperature level output switch 6a of the footswitch 6 is stepped on, the control unit 34 instructs the temperature setting units 33 (33a to 33d) to set the temperature values associated with the temperature level of level 5 for the heating elements. Moreover, the control unit 34 brings the element temperature measurement/output control units 32 (32a to 32d) to an output control state. Consequently, 210° C. is set for the heating elements 21a and 21b, and 220° C. is set for the heating element 21c.

If the designated temperature level output switch 6b of the footswitch 6 is stepped on, the control unit 34 instructs the temperature setting units 33 (33a to 33d) to set the temperature values associated with the temperature of level 3 for the heating elements. The control unit 34 then brings the element temperature measurement/output control units 32a to 32c to the output control state. Consequently, 190° C. is set for the heating elements 21a and 21b and 200° C. is set for the heating element 21c. Power feed is then started.

Figure 6A:
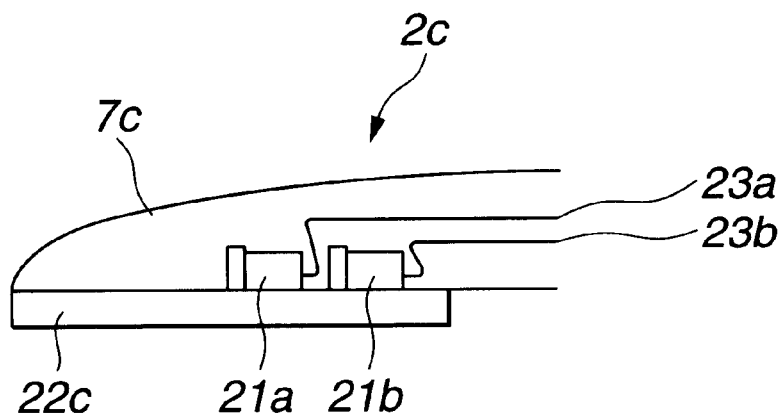
FIG. 6A is a schematic diagram showing another variant of the coagulating/incising forceps shown in FIG. 4A and the lateral side of the heating treatment member in the horizontal direction.
Figure 6B:
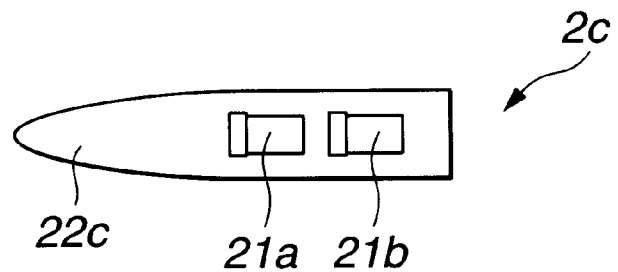
FIG. 6B is a schematic diagram showing the upper side of the heating treatment member shown in FIG. 6A in the vertical direction.

Next, a description will be made of a case where the coagulating/incising forceps 2c having the heating treatment member 7c described in conjunction with FIG. 6A and FIG. 6B is connected to the main unit.

The heating treatment member 7c has, as mentioned above, two heating elements 21 incorporated therein. The heating elements 21 are juxtaposed near the proximal end of the elongated heat transfer plate 22b.

Similarly to when the coagulating/incising forceps 2 having the heating treatment member 7 is connected to the main unit 3, when the coagulating/incising forceps 2c having the heating treatment member 7c is connected to the main unit 3, the forceps identifying unit 31 identifies the type of forceps according to information concerning the type of forceps received from the forceps identifier 10. The forceps identifying unit 31 then transmits information of the type of forceps to the control unit 34.

The control unit 34 identifies the type of connected forceps as the coagulating/incising forceps 2c having the heating treatment member 7c as described in conjunction with FIG. 6A and FIG. 6B. The control unit 34 then reads numerical information concerning the heating elements 21 and a set temperature table, which are relevant to the coagulating/incising forceps 2c, from the memory 35.

TABLE 3

Temperature to which each heating element is set [° C.]

| Designated temperature level | Heating element 1 | Heating element 2 | Heating element 3 | Heating element 4 |
|---|---|---|---|---|
| 1 | 180 | 160 | NC | NC |
| 2 | 190 | 170 | NC | NC |
| 3 | 200 | 180 | NC | NC |
| 4 | 210 | 190 | NC | NC |
| 5 | 220 | 200 | NC | NC |

The set temperature table of Table 3 lists temperature values so that the heating element 21a responsible for heating the distal part of the heat transfer plate 22b that extends largely will be heated to the higher temperature and the heating element 21b will be heated to the lower temperature. This is intended to minimize uneven temperature occurring on the surface of the heat transfer plate 22 that comes into contact with a living tissue.

If the standby switch 14 is pressed, the control unit 34 discontinues the standby state, puts out the standby indicator LED 14b, and thus establishes the output enabled state. If the maximum temperature level output switch 6a of the footswitch 6 is stepped on, the control unit 34 instructs the temperature setting units 33 (33a to 33d) to set the temperature values associated with the temperature level of level 5 for the heating elements. Moreover, the control unit 34 brings the element temperature measurement/output control units 32a and 32b to an output control state. Consequently, 220° C. is set for the heating element 21a, and 200° C. is set for the heating element 21b. Power feed is then started.

If the designated temperature level output switch 6b of the footswitch 6 is stepped on, the control unit 34 instructs the temperature setting units 33 (33a to 33d) to set the temperature values associated with, for example, the temperature level of level 3 for the heating elements. Moreover, the control unit 34 brings the element temperature measurement/output control units 32a and 32b to the output control state. Consequently, 200° C. is set for the heating element 21a, and 180° C. is set for the heating element 21b. Power feed is then started.

Consequently, according to the present embodiment, the temperature values to be set for the heating elements 21 are varied depending on the shape of forceps or the arrangement of the heating elements 21. Thus, uneven temperature occurring on the heat transfer plate 22 can be minimized and a stable capability for coagulation or incision can be offered.

(Second Embodiment)

Figure 11:
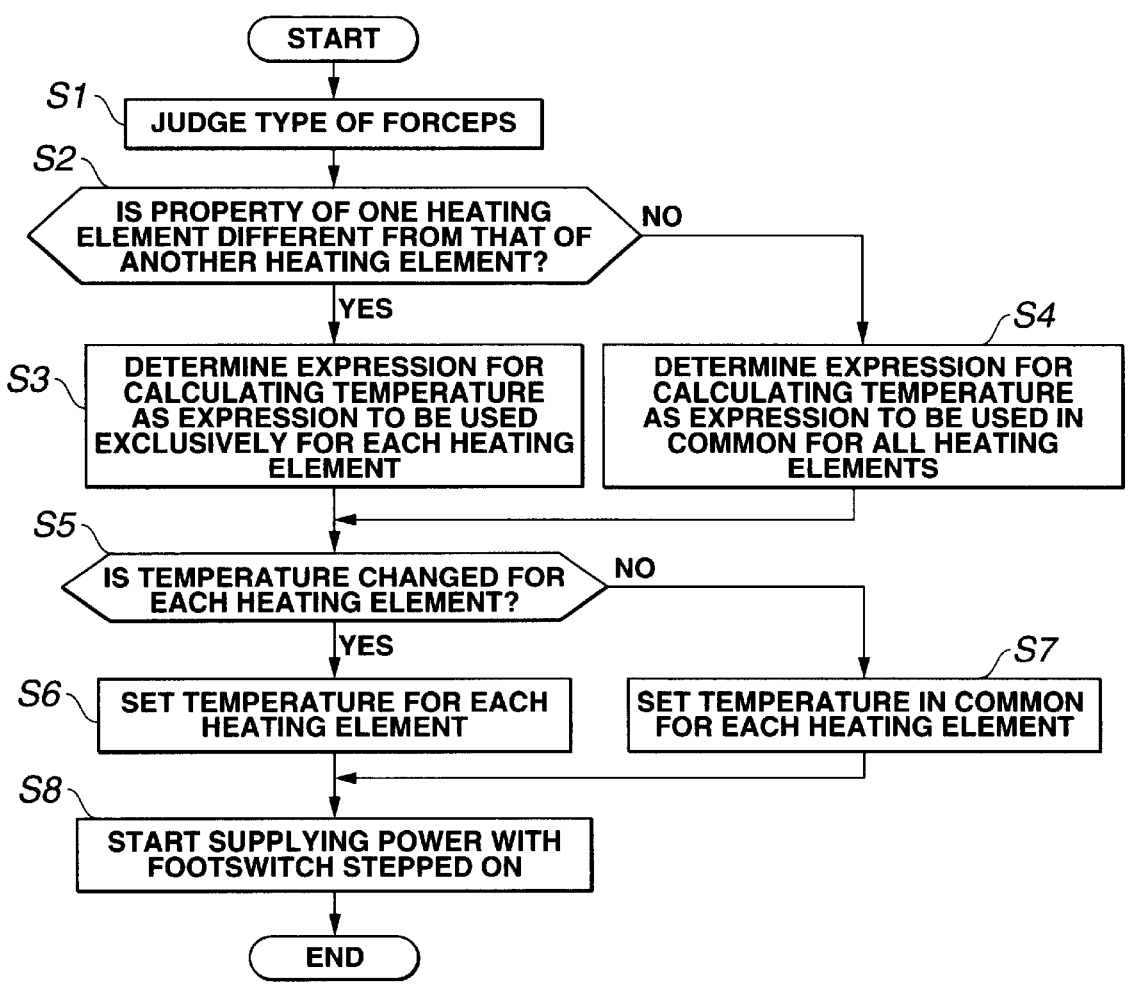
FIG. 11 is a flowchart describing operation to be performed by the heating treatment system in accordance with the second embodiment of the present invention.
Figure 12:
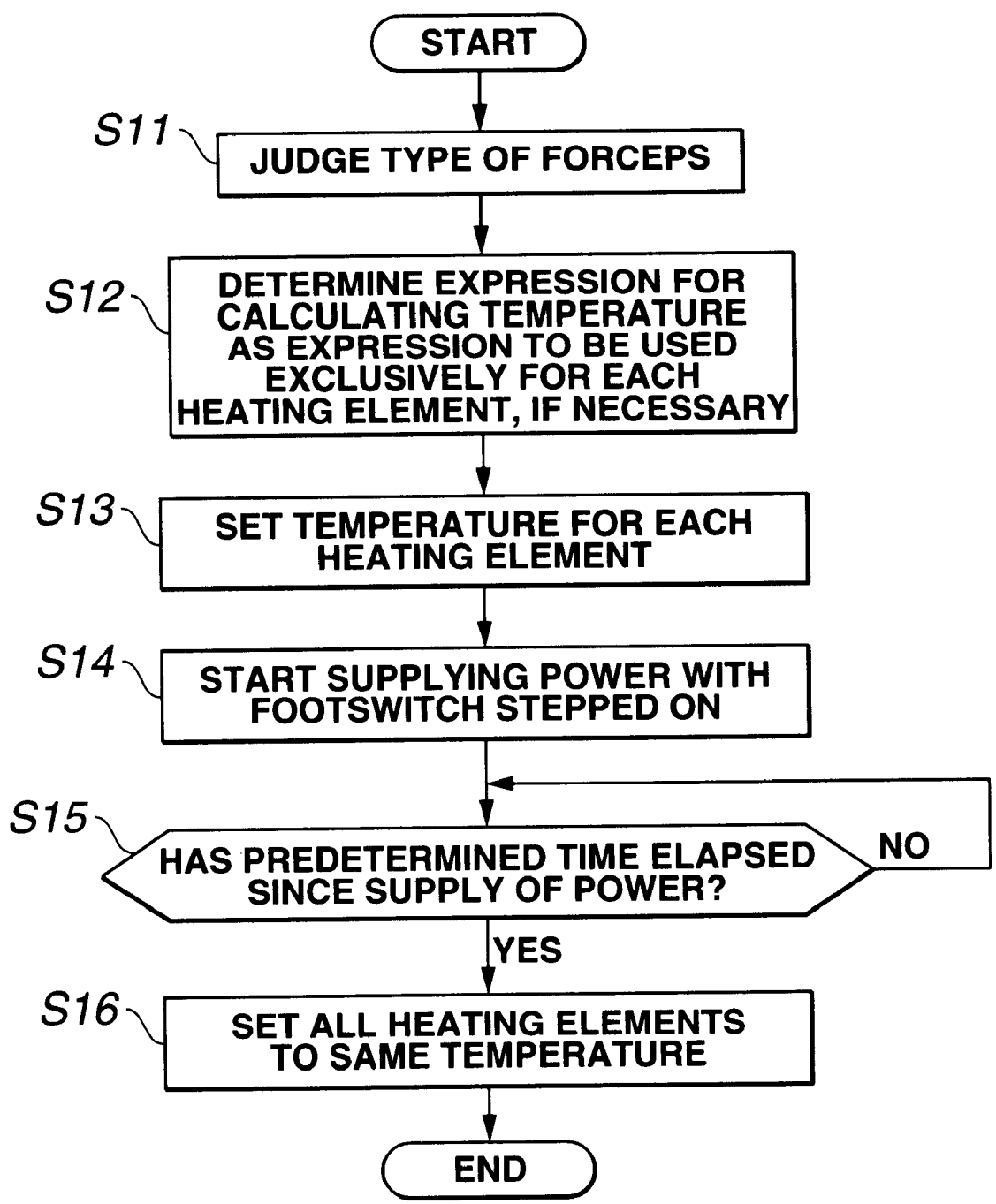
FIG. 12 is a flowchart describing operation to be performed by a variant of the heating treatment system shown in FIG. 11.

FIG. 9A to FIG. 12 are concerned with a second embodiment of the present invention. FIG. 9A, FIG. 9B, and FIG. 9C are schematic explanatory diagrams showing a heating treatment member of coagulating/incising forceps included in a heating treatment system in accordance with the second embodiment of the present invention. FIG. 9A is a schematic diagram showing the heating treatment member from a direction horizontal to the lateral side of the member. FIG. 9B is a schematic diagram showing the upper side of the heating treatment member in the vertical direction. FIG. 9C is an enlarged diagram showing heaters shown in FIG. 9A. FIG. 10A, FIG. 10B, and FIG. 10C are schematic explanatory diagrams showing a variant of the coagulating/incising forceps shown in FIG. 9A. FIG. 10A is a schematic diagram showing the lateral side of the heating treatment member in the horizontal direction. FIG. 10B is a schematic diagram showing the upper side of the heating treatment member shown in FIG. 10A in the vertical direction. FIG. 10C is an enlarged view showing a heater block shown in FIG. 10A. FIG. 11 is a flowchart describing operation to be performed by the heating treatment system in accordance with the second embodiment of the present invention. FIG. 12 is a variant of the flowchart of FIG. 11.

According to the first embodiment, the present invention is implemented in the heating treatment system that includes the coagulating/incising forceps 2 having the heating treatment member 7 in which the plurality of heating elements 21 is thermally coupled to the heat transfer plate 22. According to the second embodiment, the present invention is implemented in the heating treatment system that includes coagulating/incising forceps having one heating element in which a plurality of heating bodies is thermally coupled to a heat transfer plate. The other features are identical to those of the first embodiment, and the description of the identical features is omitted. The same reference numerals are assigned to components identical to those of the first embodiment.

As shown in FIG. 9A, FIG. 9B, and FIG. 9C, the heating treatment system in accordance with the second embodiment includes coagulating/incising forceps 40 having a heating treatment member 41 in which heating elements of a different shape are incorporated.

The heating treatment member 41 has, as shown in FIG. 9A and FIG. 9B, a heater block 43 thermally coupled as heating elements to the heat transfer plate 22. The heater block 43 includes a plurality of heating elements 42, for example, three heating elements 42a, 42b, and 42c. What is referred to as a heater element herein is a thin-film resistor formed, for example, on a ceramic substrate or a metallic substrate.

The heater block 43 has, as shown in FIG. 9C, the heating elements 42 (42a to 42c) electrically connected to an electrode unit 45 by way of a wiring pattern 44. The electrode unit 45 has coaxial leads 23a, 23b, and 23c coupled to the proximal end thereof. Electricity is conducted to the heating elements 42a, 42b, and 42c over the coaxial leads 23a, 23b, and 23c.

The heating elements 42 (42a to 42c) are thermally coupled to the heat transfer plate 22. The heat transfer plate 22 is heated in order to coagulate or incise a living tissue.

Consequently, the heating treatment member 41 employed in the second embodiment can provide the same advantages as the heating treatment member 7 employed in the first embodiment. Moreover, the number of components can be decreased.

FIG. 10A, FIG. 10B, and FIG. 10C show a variant of the coagulating/incising forceps 40.

A heating treatment member 41b of the coagulating/incising forceps 40b shown in FIG. 10A, FIG. 10B, and FIG. 10C includes a heater block 43b in which two heating elements 42a and 42b are incorporated. The heater 43b is placed near the proximal end of a heat transfer plate 22 that is thinner than the heat transfer plate 22 included in the heating treatment member 41 of the coagulating/incising forceps 40 shown in FIGS. 9A to 9C. The heating treatment member 41b has the same capability for coagulation or incision as the heating treatment member 7b of the coagulating/incising forceps 2b described in relation to the first embodiment.

The heating treatment members 41 and 41b shown in FIG. 9A to FIG. 10C are different from each other in the length of the wiring pattern 44. A resistance given by the electrode unit 45 is therefore different from the one given by an electrode unit 45b.

The element temperature measurement/output control units 32 (32a to 32d) described in relation to the first embodiment calculate the temperature values of the heating elements 21 from the resistance values exhibited by the heating elements 21 (21a, 21b, and 21c). According to the present embodiment, an expression for calculating a temperature value is differentiated among the heating elements 42 (42a, 42b, and 42c).

Referring to FIG. 9A to FIG. 10C, operation to be exerted by the heating treatment system having the foregoing components will be described in conjunction with the flowchart of FIG. 11.

Similarly to the first embodiment, when coagulating/incising forceps is connected to the main unit 3, the forceps identifying unit 31 identifies the type of forceps according to information concerning the type of forceps received from the forceps identifier 10. The forceps identifying unit 31 then transmits the identified type of forceps to the control unit 34.

The control unit 34 judges the type of connected forceps by referencing data stored in the memory 35 according to the information concerning the type of forceps received from the forceps identifying unit 31 (step S1). The control unit 34 then judges from the identified type of forceps whether the heating elements 42 exhibit the same resistance-versus-temperature characteristic among the elements (step S2).

Assuming that the connected coagulating/incising forceps includes the heater block 43 or 43b described with reference to FIG. 9A to FIG. 10, the heating elements included in the heater block are different from one another in the resistance-versus-temperature characteristic. In this case, the control unit 34 determines an expression for calculating temperature relative to each of the heating elements by referencing the data stored in the memory 35 (step S3).

When the connected coagulating/incising forceps has the heating treatment member 7 composed of the same heating elements 21 as shown in FIG. 4A to FIG. 6C, a common expression for calculating temperature is used relative to all the heating elements (step S4).

Thereafter, the control unit 34 judges from the data stored in the memory 35 whether a temperature value set for each heating element must be changed (step S5).

When the connected coagulating/incising forceps is the coagulating/incising forceps 2 having the heating treatment member 7 as shown in FIG. 4A to FIG. 6c, a temperature value is set for each heating element according to a designated temperature level as described in relation to the first embodiment (step S6).

When the connected coagulating/incising forceps is the coagulating/incising forceps 40 having the heating treatment member 41 as described with reference to FIG. 9A, FIG. 9B, and FIG. 9C, the control unit 34 references Table 1 of the set temperature table as described in relation to the first embodiment. The control unit 34 then sets a temperature value for each heating element according to a designated temperature level. At this time, operation identical to those performed when the coagulating/incising forceps having the heating treatment member 7 is connected is performed as described in relation to the first embodiment.

When the connected coagulating/incising forceps is the coagulating/incising forceps 40 having the heating treatment member 41b as described with reference to FIG. 10A, FIG. 10B, and FIG. 10C, the control unit 34 references Table 3 of the set temperature table as described in relation to the first embodiment. The control unit 34 then sets a temperature value for each heating element according to a designated temperature level. Operation to be performed at this time is identical to those performed when the coagulating/incising forceps 2c is connected to the main unit 3 as described in relation to the first embodiment.

In a case where it is unnecessary to set different temperature values for the heating elements, though a concrete case will not be presented in this stage, the control unit 34 sets the same temperature value for all the heating elements 42 (step S7). For example, temperature levels 1 to 5 are predefined at intervals of 10° C. within the range from 170° C. to 210° C.

The temperature values are then set according to a designated one of the temperature levels. Similarly to the first embodiment, coagulation or incision is performed depending on whichever of the maximum temperature level output switch 6a and designated temperature level output switch 6b of the footswitch 6 is stepped on (step S8).

Consequently, according to the second embodiment, even when the coagulating/incising forceps 40 having the heater block 43 (heating elements) in which the plurality of heating elements exhibiting different temperature characteristics is incorporated is connected to the main unit, power feed can be achieved using the same power supply. Moreover, the same advantages as those of the first embodiment are provided.

Incidentally, the heating treatment system may operates as described in the flowchart of FIG. 12.

Similarly to the operation described in the flowchart of FIG. 11, when coagulating/incising forceps is connected to the main unit 3, the forceps identifying unit 31 identifies the type of forceps according to information concerning the type of forceps received from the forceps identifier 10. The forceps identifying unit 31 then transmits the information of the type of forceps to the control unit 34.

The control unit 34 identifies the type of connected forceps by referencing the data stored in the memory 35 according to the information of the type of forceps received from the forceps identifying unit 31 (step S11). Herein, the control unit 34 determines an expression for calculating temperature relative to each heating element according to the identified type of forceps (step S12), if necessary. Thereafter, the control unit 34 sets a temperature value for each heating element according to a designated temperature level (step S13).

When the maximum temperature level output switch 6a or designated temperature level output switch 6b of the footswitch is stepped on, power feed is started (step S14).

The control unit 34 uses a built-in timer that is not shown to measure the time that has elapsed since the start of power feed, and judges whether a predetermined time, for example, 3 sec has elapsed (step S15).

If the predetermined time has elapsed, the control unit 34 sets the smallest one of the temperature values for the heating elements that have been heated up to the temperature values independently set for the heating elements. Thus, the different temperature values are re-set to the same temperature value (step S16).

For example, as described in relation to the first embodiment, assume that the temperature values read from in Table 1 of the set temperature table in association with a designated temperature level of level 3 are set for the heating elements. In this case, when 3 sec has elapsed since the start of power feed, the control unit 34 sets the smallest temperature value of 180° C., which is specified for heating element 2 in Table 1, for the three heating elements.

Although different temperature values are set for the heating elements in order to minimize uneven temperature occurring on the heat transfer plate at the start of heating, once the time during which the temperatures of the heating elements presumably rise evenly has elapsed, the different temperature values are re-set to the same temperature value. Consequently, even when power must be fed for a prolonged period of time, the temperature of the heat transfer plate can be held even.

(Third Embodiment)

Figure 13:
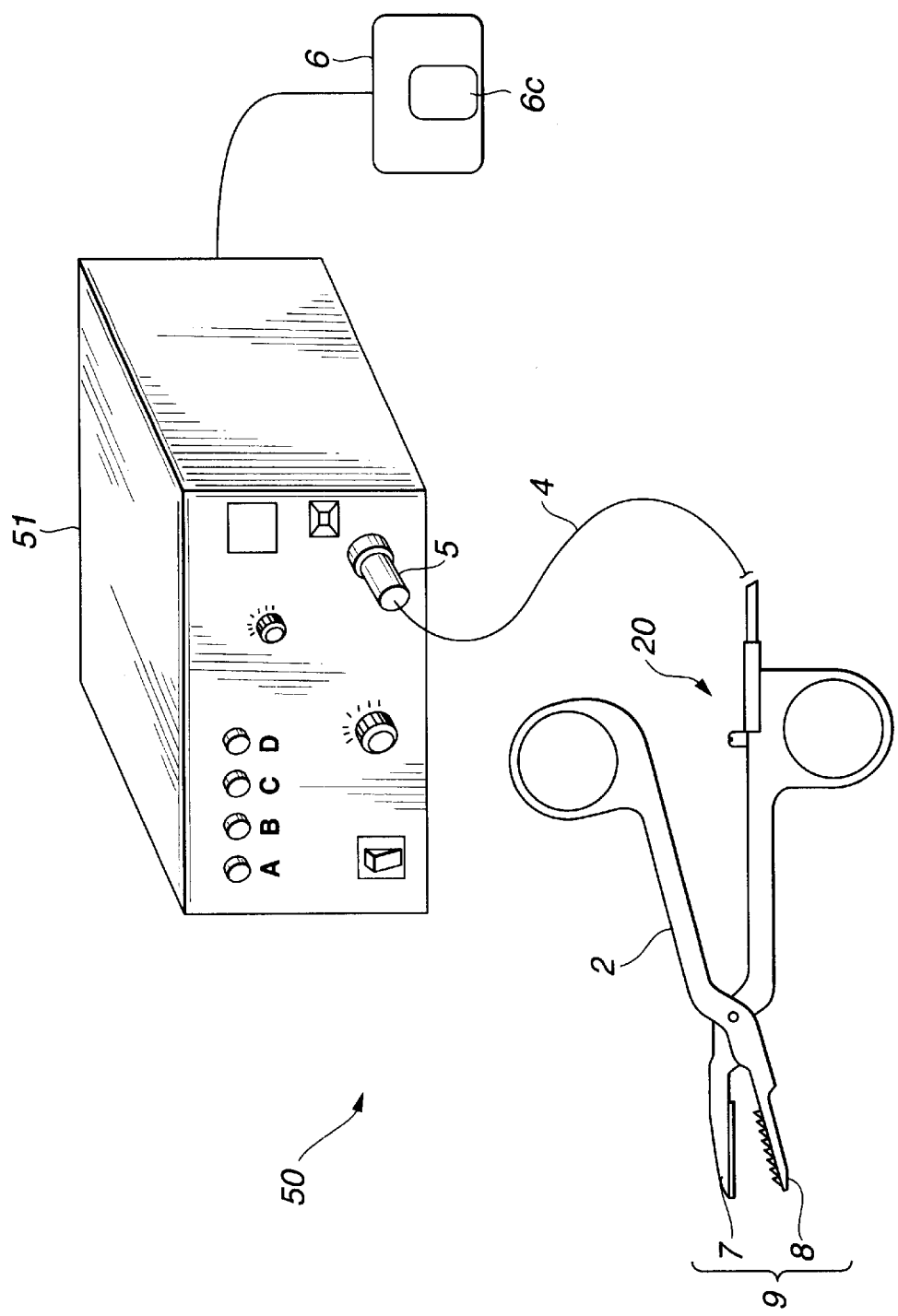
FIG. 13 shows the overall configuration of a heating treatment system in accordance with a third embodiment of the present invention.
Figure 16:
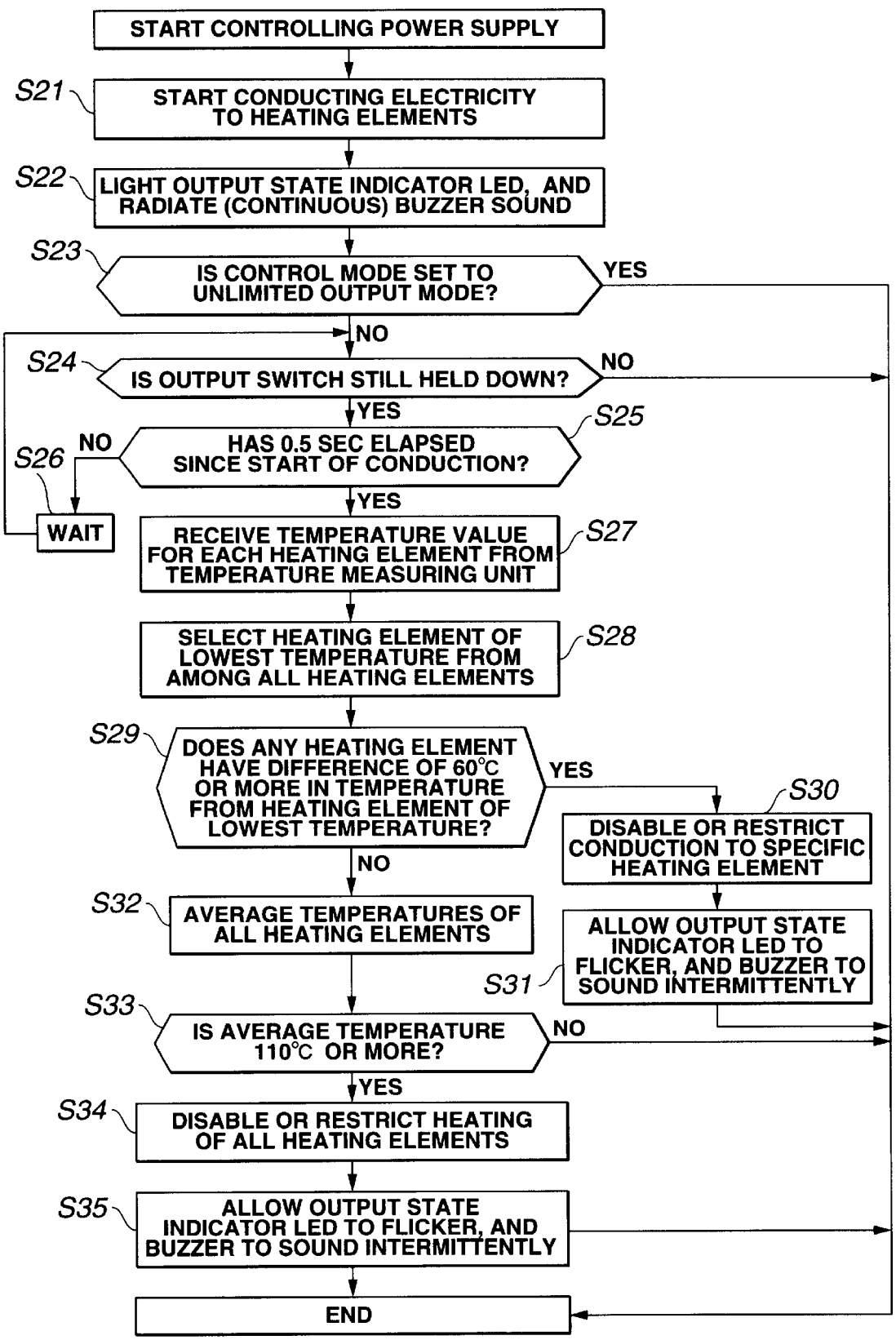
FIG. 16 is a flowchart for explaining operation to be performed by the heating treatment system in accordance with the third embodiment of the present invention.
Figure 17:
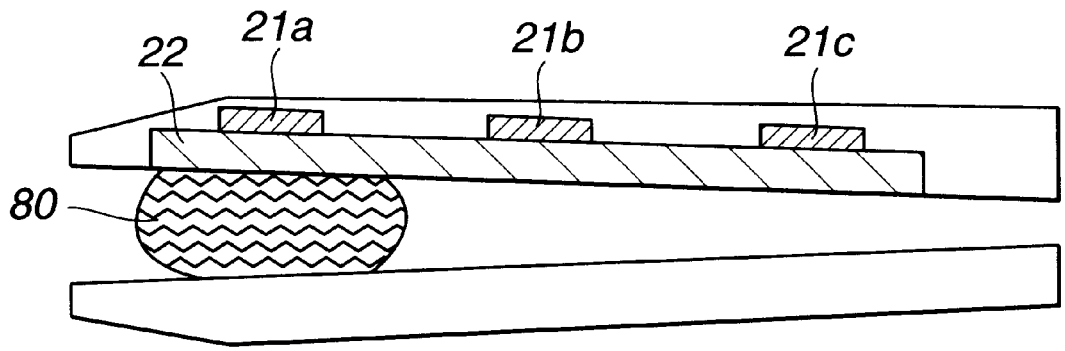
FIG. 17 is an explanatory diagram showing a use situation of the treatment unit of the coagulating/incising forceps part of which is used to clamp a living tissue.
Figure 18:
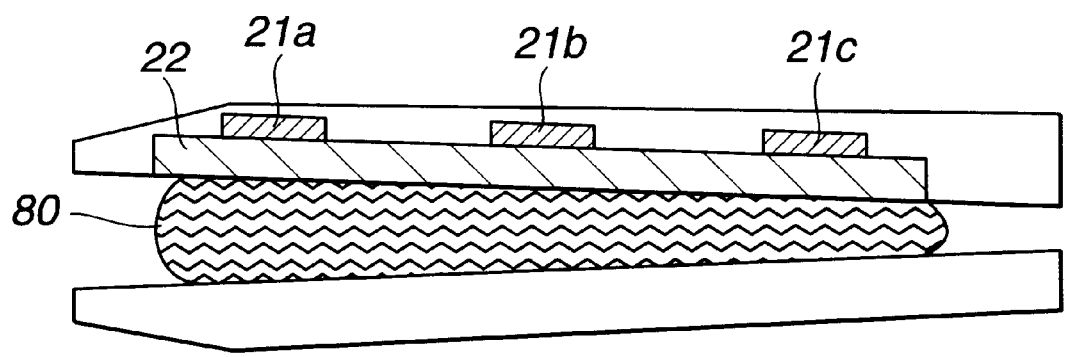
FIG. 18 is an explanatory diagram showing a use situation of the treatment unit of the coagulating/incising forceps that is entirely used to clamp a living tissue.
Figure 19:
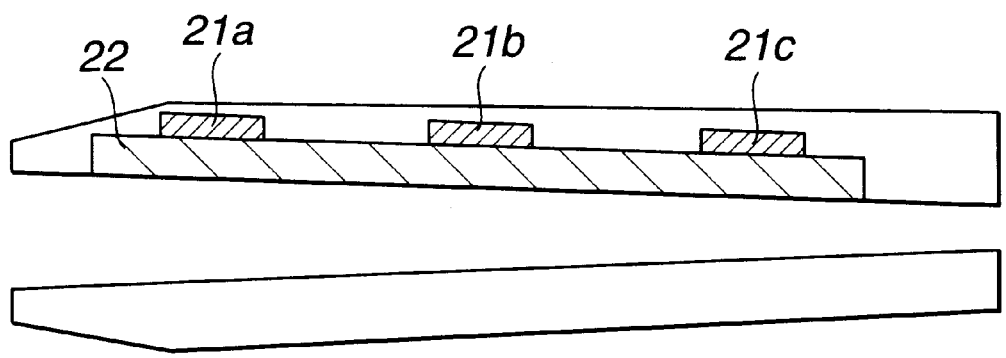
FIG. 19 is an explanatory diagram showing an unused situation of the treatment unit of the coagulating/incising forceps to clamp a living tissue.
Figure 20:
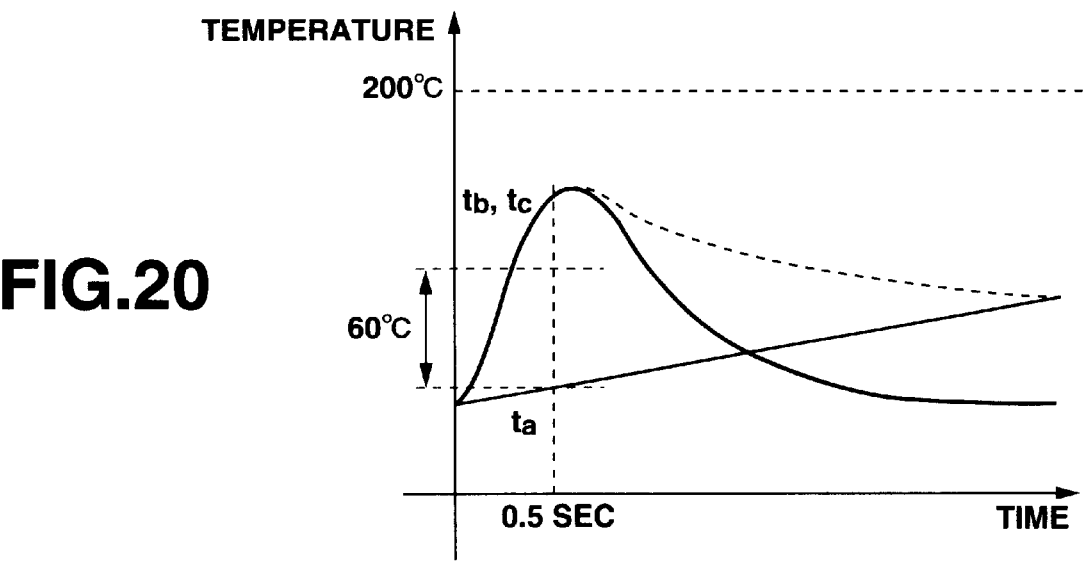
FIG. 20 is a graph indicating changes in the temperatures of heating elements occurring in the use situation shown in FIG. 17 during electrical conduction.
Figure 21:
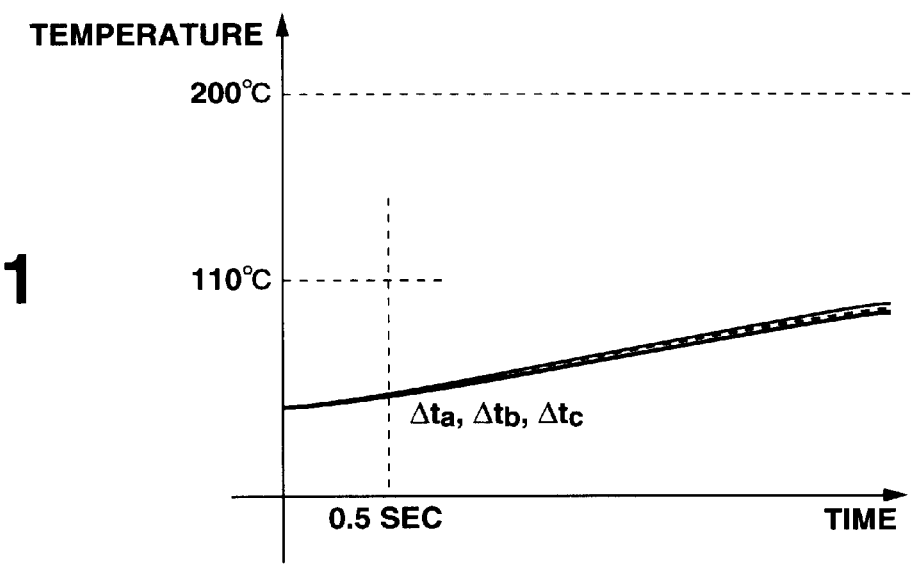
FIG. 21 is a graph indicating changes in the temperatures of the heating elements occurring in the use situation shown in FIG. 18 during electrical conduction.
Figure 22:
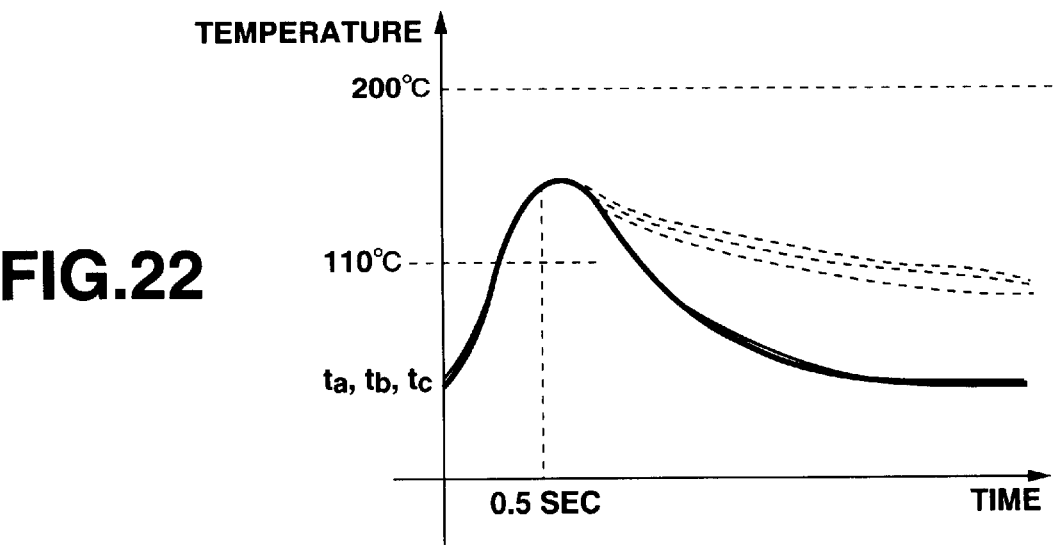
FIG. 22 is a graph indicating changes in the temperatures of the heating elements occurring in the use situation shown in FIG. 19 during electrical conduction.

FIG. 13 to FIG. 22 are concerned with a third embodiment of the present invention. FIG. 13 shows the overall configuration of a heating treatment system in accordance with the third embodiment of the present invention. FIG. 14A and FIG. 14B show the appearance of a main unit of the heating treatment system shown in FIG. 13. FIG. 14A is a perspective view of the appearance of the main unit seen from the front panel thereof. FIG. 14B shows the appearance of the back panel of the main unit. FIG. 15 is a circuit block diagram for explaining the heating treatment system in accordance with the third embodiment of the present invention. FIG. 16 is a flowchart describing operation to be performed by the heating treatment system in accordance with the third embodiment of the present invention. FIG. 17 is an explanatory diagram showing a use situation of a treatment unit of coagulating/incising forceps part of which is used to clamp a living tissue. FIG. 18 is an explanatory diagram showing a use situation of the treatment unit of the coagulating/incising forceps that is entirely used to clamp a living tissue. FIG. 19 is an explanatory diagram showing a use situation of the treatment unit of the coagulating/incising forceps that clamps no living tissue. FIG. 20 is a graph indicating changes in the temperatures of heating elements occurring in the use situation shown in FIG. 17 during electrical conduction. FIG. 21 is a graph indicating changes in the temperatures of the heating elements occurring in the use situation shown in FIG. 18 during electrical conduction. FIG. 22 is a graph indicating changes in the temperatures of the heating elements occurring in the use situation shown in FIG. 19 during electrical conduction.

According to the first and second embodiment, the type of connected forceps is judged by referencing data stored in advance in the memory 35 according to information concerning the type of forceps received from the coagulating/incising forceps 2. Feed of power to the heating elements 21 is controlled based on the judged type of connected forceps. According to the third embodiment, a difference in temperature between the heating elements 21 is detected in order to judge the use situation of the treatment unit 9 signifying how the treatment unit 9 is used to treat a living tissue. Consequently, power feed to the heating elements 21 is controlled based on the use situation of the treatment unit 9. The other features are identical to those of the first embodiment, and the description of the features is therefore omitted. The same reference numerals are assigned to components identical to those of the first embodiment.

As shown in FIG. 13, a heating treatment system 50 in accordance with the third embodiment of the present invention consists mainly of coagulating/incising forceps 2 in which a plurality of heating elements 21 is incorporated in the same manner as that in the first embodiment, and of a main unit 51. A footswitch 6 having an output switch 6c can be connected to the main unit 51.

The coagulating/incising forceps 2 has a main unit connector 5 attached to a connection cable 4 extending therefrom. The main unit connector 5 is coupled to the main unit 51 so that it can be uncoupled freely. The coagulating/incising forceps 2 has a treatment unit 9 that includes a heating treatment member 7 and an elastic receptor 8. The heating treatment member 7 has a plurality of heating elements 21 incorporated therein, and the elastic receptor 8 can approach to or recede from the heating treatment member 7.

The number of heating elements incorporated in the heating treatment member 7 varies depending on the type of forceps suitable for a treatment. The detailed structures of the heating treatment 7 and elastic receptor 8 are identical to those shown in FIG. 7A and FIG. 7B and described in relation to the first embodiment The coagulating/incising forceps 2 employed in the present embodiment may not include the forceps identifier 10 that indicates the type of forceps as described in relation to the first and second embodiments.

The main unit 51 can conduct electricity to up to four heating elements simultaneously. The coagulating/incising forceps having up to four heating elements incorporated therein can therefore be connected to the main unit 51.

Figure 14A:
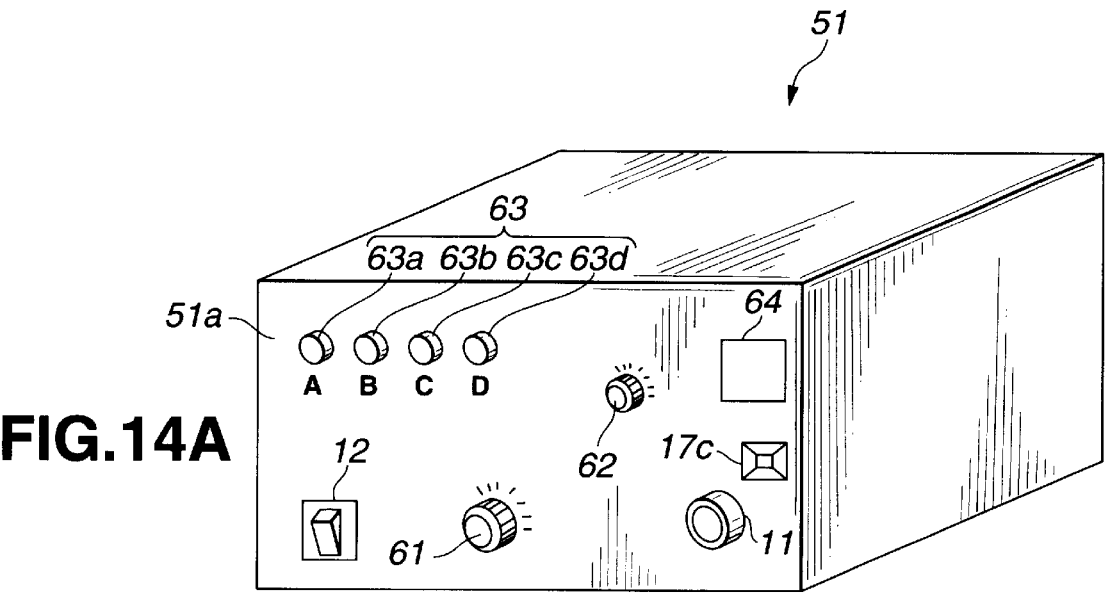
FIG. 14A is a perspective view showing the appearance of a main unit that is included in the heating treatment system shown in FIG. 13 and that is seen from the front panel thereof.
Figure 14B:
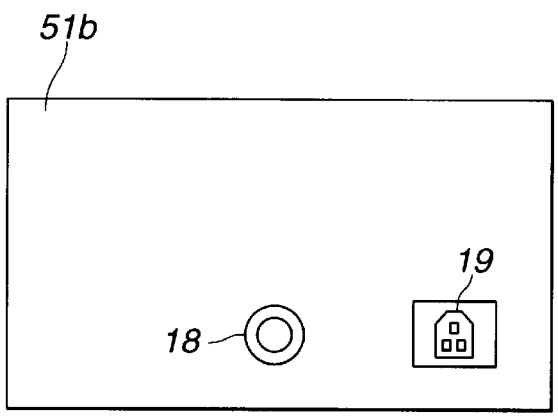
FIG. 14B shows the back panel of the main unit shown in FIG. 14A.

As shown in FIG. 14A and FIG. 14B, the main unit 51 has a front panel 51a and a back panel 51b.

Referring to FIG. 14A, the front panel 51a has a connector receptacle 11, a power switch 12, a buzzer 17c, a temperature adjustment knob 61, a control mode selection knob 62, state-of-element indicator LEDs 63 (63a to 63d), and an output state indicator LED 64. The temperature adjustment knob 61 is used to adjust a temperature value set for the heating elements 21. The control mode selection knob 62 is used to select a control mode in which the heating elements 21 are controlled. The state-of-element indicator LEDs 63 indicate the states of the heating elements 21. The output state indicator LED 64 indicates the situation of power feed to the heating elements 21.

The control mode selection knob 62 enables a user to select any of three control modes; that is, an output stop mode, an output restriction mode, and an output non-restriction mode.

When the heating elements 21 are normal, the state-of-element indicator LEDs 63 are lit in green. When any heating element is abnormal or unconnected, the associated state-of-element indicator LED 63 is put out. The temperature adjustment knob 61 enables adjustment of a temperature value within a range from, for example, 160° C. to 220° C. The description of the present embodiment will proceed on the assumption that the temperature adjustment knob 61 is used to set a temperature value to 200° C.

Referring to FIG. 14B, the back panel 51b has, similarly to the one included in the first embodiment, a footswitch connector receptacle 18 and a power inlet 19.

As shown in FIG. 15, the coagulating/incising forceps having up to four heating elements 21 (21a to 21d) can be connected to the main unit 51. The main unit 51 includes state-of-element detecting units 71 (71a to 71d), temperature-of-element measuring units 72 (72a to 72d), temperature-of-element control units 73 (73a to 73d), and output units 74 (74a to 74d) which are associated with four channels that are allocated to the heating elements 21 (21a to 21d). If the number of heating elements 21 incorporated in the coagulating/incising forceps 2 is three or less, channel A and subsequent channels are orderly allocated to the heating elements 21.

The state-of-element detecting units 71 (71a to 71d) each judge whether a resistance value exhibited by an associated heating element falls within a range of normal values, and thus judge whether the heating element is normal. A signal representing the result of judgment is sent to a control unit 75.

The temperature-of-element measuring units 72 (72a to 72d) each measures the temperature of an associated heating element by using the fact that the resistance values exhibited by the heating elements 21 vary depending on temperature. Specifically, the temperature-of-element measuring unit 72 that serves as a resistance detecting facility measures a current or voltage value that varies with a change in the resistance value exhibited by the heating element 21, and thus detects the resistance value exhibited by the heating element 21. Based on the detected resistance value, the temperature of the heating element 21 is calculated.

The temperature-of-element control units 73 (73a to 73d) each compare a value measured by an associated one of the temperature-of-element measuring units 72 (72a to 72d) with a set value received from a temperature setting unit 76. The temperature-of-element control unit 73 controls a voltage to be applied to an associated heating element so that the heating element 21 will be heated up to the set temperature value.

The temperature setting unit 76 determines a temperature value, which must be retained during electrical conduction to the heating elements incorporated in the coagulating/incising forceps, according to a value designated using the temperature adjustment knob 61 included in an operator panel 36. The temperature setting unit 76 transmits the determined temperature value to the temperature-of-element control units 73 (73a to 73d). Incidentally, the temperature setting unit 76 determines the same temperature value for all the heating elements.

The output units 74 feed power in response to instructions sent from the temperature-of-element control units 73 (73a to 73d) with the permission of the control unit 75.

A control mode switching unit 77 switches control modes so as to establish a control mode selected using the control mode selection knob 62 on the operator panel 36. If necessary, the control mode switching unit 77 transmits a current control mode to the control unit 75.

The control unit 75 checks signals sent from the state-of-element detecting units 71 (71a to 71d), and enables power feed to normal heating elements but disables power feed to an abnormal or unconnected heating element. The control unit 75 checks the temperatures of the heating elements so as to judge the state of a living tissue clamped by the coagulating/incising forceps 2. If any heating element need not be heated, as long as the output stop mode is selected as a control mode, power feed to the heating element is disabled. When the output restriction mode is selected, power feed to the heating element is restricted in order to limit the temperature of the heating element to up to 100° C.

What is referred to as the operator panel 36 is a generic term for various switches including the temperature adjustment knob 61 exposed on the front panel 51a of the main unit 51. Moreover, various indicator LEDs exposed on the front panel 51a of the main unit 51 are generically termed an indicator panel 38.

Referring to FIG. 17 to FIG. 22, operation to be exerted by the thus configured heating treatment system will be described using the flowchart of FIG. 16.

The power switch 12 is turned on, whereby the whole heating treatment system 50 is activated.

When the coagulating/incising forceps 2 is connected to the main unit 51, the state-of-element detecting units 71 (71a to 71d) each judge whether the resistance value exhibited by an associated heating element 21 (any of 21a to 21d) to which the channels are allocated falls within a range of normal values.

If the heating element 21 is unconnected or disconnected, the resistance value exhibited by the heating element exceeds the normal range. If the heating element 21 is short-circuited, the resistance value exhibited by the heating element falls below the normal range. In consideration of this fact, the state-of-element detecting unit 71 (any of 71a to 71d) judges whether an associated heating element 21 (any of 21a to 21d) is normal. If the state-of-element detecting unit 71 (any of 71a to 71d) judges that the heating element 21 is normal, the state-of-element detecting unit 71 transmits a normal element-connected signal to the control unit 75. The control unit 75 enables electrical conduction to the normal heating element 21. In contrast, if the state-of-element detecting unit 71 (any of 71a to 71d) judges that an associated heating element 21 is abnormal, the state-of-element detecting unit 71 transmits an abnormal element-unconnected signal to the control unit 75. The control unit 75 disables electrical conduction to the abnormal heating element 21.

At the same time, the control unit 75 lights in green any of the state-of-element indicator LEDs 63 (63a to 63d) associated with a normal heating element but puts out any thereof associated with an abnormal or unconnected heating element. The state-of-element indicator LEDs 63 are included in the indicator panel 38.

A description will proceed on the assumption that the coagulating/incising forceps 2 having three heating elements 21 incorporated therein is employed.

Assume that all the three heating elements 21a to 21c incorporated in the coagulating/incising forceps 2 are normal. In this case, the state-of-element detecting units 71a to 71c judge that the heating elements 21a to 21c to which channels a, b, and c are allocated are normal. The state-of-element detecting unit 71d judges that a heating element 21d to which a channel d is allocated is unconnected or disconnected.

The control unit 75 receives element-connected or unconnected signals from the state-of-element detecting units 71 (71a to 71d). Based on the signals, the control unit 75 enables electrical conduction along the channels a, b, and c but disables electrical conduction along the channel d. At the same time, the control unit 75 lights the state-of-element indicator LEDs 63a to 63c but puts out the state-of-element indicator LED 63d.

When the output switch 6c of the footswitch 6 is stepped on, the footswitch input unit 37 transmits an output start signal to the control unit 75 through the footswitch connector receptacle 18.

In response to the output start signal, the control unit 75 transmits a control signal to the output units 74a to 74d so that the output units 74 will conduct electricity to the heating elements 21a to 21c that are judged to be normal. The output units 74a to 74c then start electrical conduction to the normal heating elements 21a to 21c (step S21). Consequently, the heating elements 21a to 21c are heated. At the same time, the control unit 75 lights the output state indicator LED 64 and sounds the buzzer 17c continuously (step S22).

At this time, three use situations are conceivable concerning how the treatment unit 9 of the coagulating/incising forceps 2 clamps a living tissue.

Specifically, in one of the three use situations, part of the treatment unit 9 of the coagulating/incising forceps 2 is, as shown in FIG. 17, used to clamp a living tissue 80. In other use situation, the treatment unit 9 of the coagulating/incising forceps 2 is entirely, as shown in FIG. 18, used to clamp the living tissue 80. In the other use situation, the treatment unit 9 of the coagulating/incising forceps 2 does not clamp the living tissue 80. To begin with, the use situation shown in FIG. 17 will be described below.

FIG. 20 graphically indicates changes in the temperatures of the heating elements 21a to 21c occurring during electricity conduction to the heating elements 21a to 21c with the living tissue 80 clamped using part of the treatment member 9 of the coagulating/incising forceps 2.

When electricity is conducted to the heating elements 21a to 21c, the heating elements 21a to 21c are heated. Heat dissipated from the heating element 21a passes through the heat transfer plate 22 and reaches the living tissue 80. Consequently, the living tissue 80 is heated and progressively coagulated or incised.

The living tissue 80 contains much moisture. Immediately after heating is started, heat transferred from the heating element 21a to the living tissue 80 is used to evaporate the moisture. Therefore, the temperature of part of the heat transfer plate 22 in contact with the living tissue 80 is as low as approximately 100° C. Consequently, immediately after heating is started, the temperature of the heating element 21a remains low because the heating element 21a is robbed of almost all dissipated heat by the heat transfer plate 22. Moreover, the temperature of the heating element 21a rises slowly.

In contrast, unlike heat dissipated from the heating element 21a, heat dissipated from the heating elements 21b and 21c is used to heat the heating elements 21b and 21c themselves because of the absence of the living tissue 80. Consequently, the temperatures of the heating elements 21b and 21c rapidly rise up to the set temperature values.

However, all that must be heated is the portion of the treatment unit that clamps the living tissue 80. Heating the other portion thereof leads to wasting of electric energy and an increase in the time required to cool the heat transfer plate 22 after completion of power feed.

In order to solve this problem, according to the present embodiment, the control unit 75 extends control as described below.

When the output switch 6c of the footswitch 6 is stepped on, the control unit 75 first checks whichever of the output stop mode, output restriction mode, and output non-restriction mode is selected as a control mode using the control mode selection knob 62 (step S23). When the output non-restriction mode is selected as the control mode, the control unit 75 does not perform subsequent processing steps S24 to S35. Power feed is continued until the output switch 6c is released (as long as the output switch 6c is held down), and controlling power feed is terminated.

When the control mode is not the output non-restriction mode, that is, when the control mode is the output stop mode or the output restriction mode, the control unit 75 judges whether the output switch 6c is still held down (step S24). If the output switch 6c is still held down, the control unit 75 uses a built-in timer, which is not shown, to measure the time that has elapsed since the start of power feed. When a predetermined time T (for example, 0.5 sec) has elapsed since the start of power feed (steps S25 and S26), the control unit 75 receives information of the temperatures ta, tb, and tc of the heating elements 21a to 21c from the temperature-of-element measuring units 72a to 72c (step S27).

Thereafter, the control unit 75 recognizes that the temperature of the heating element 21a is the lowest among those of the heating elements 21a to 21c (step S28). The control unit 75 recognizes that the heating elements 21b and 21c have a difference in temperature of 60° C. or more from the heating element 21a whose temperature is the lowest (step S29).

When the control mode is the output stop mode, the control unit 75 disables heating of the identified heating elements 21b and 21c. When the control mode is the output restriction mode, the control unit 75 restricts heating to limit the temperatures of the heating elements 21b and 21c to, for example, 100° C. (step S30). At the same time, the control unit 75 changes the lighting of the output state indicator LED 64 to flickering and changes the continuous sounding of the buzzer 17c to intermittent sounding (step S31). Processing is then terminated.

As seen from FIG. 20, the temperature ta of the heating element 21a rises slowly, while the temperatures tb and tc of the heating elements 21b and 21c rise rapidly. At a certain time instant T, a difference between the temperature ta and the temperatures tb and tc reaches 60° C. or more.

The control unit 75 therefore disables or restricts heating of the heating elements 21b and 21c. Consequently, the temperatures tb and tc of the heating elements 21b and 21c gradually decrease as indicated with a solid line or a dashed line in FIG. 20.

Consequently, when part of the treatment unit 9 of the coagulating/incising forceps 2 is used to clamp the living tissue 80 as shown in FIG. 17, it is possible to heat only the heating element that lies inside the portion of the treatment unit 9 clamping the living tissue 80.

Next, a description will be made of the use situation in which, as shown in FIG. 18 or FIG. 19, the treatment unit 9 of the coagulating/incising forceps 2 is entirely used to clamp the living tissue 80 or the treatment unit 9 does not clamp the living tissue 80. FIG. 21 is a graph indicating changes in the temperature of the heating elements 21a to 21c occurring in the use situation shown in FIG. 18. FIG. 22 is a graph indicating changes in the temperatures of the heating elements 21a to 21c occurring in the use situation shown in FIG. 19.

In the use situation in which the treatment member 9 of the coagulating/incising forceps 2 is entirely used to clamp the living tissue 80 as shown in FIG. 18, when electricity is conducted to the heating elements 21a to 21c, the heating elements 21a to 21c are heated. The temperatures of the heating elements 21a to 21c rise slowly as indicated with FIG. 21.

In the use situation in which the treatment unit 9 of the coagulating/incising forceps 2 does not clamp the living tissue 80 as shown in FIG. 19, when electricity is conducted to the heating elements 21a to 21c, the heating elements 21a to 21c are heated. The temperatures of the heating elements 21a to 21c rise rapidly as indicated with FIG. 22.

The control unit 75 controls power feed to the heating elements 21a to 21c according to the sequence described in the flowchart of FIG. 16. A large difference in temperature does not occur between one of the heating elements 21a to 21c and the other heating elements. The judgment is therefore made in the negative at step S29. The control unit 75 then averages the temperatures of the heating elements 21a to 21c to work out an average temperature Tave (step S32). The average temperature Tave is then compared with a pre-set temperature value (for example, 110° C.) (step S33).

If the average temperature Tave is equal to or higher than 110° C., the control unit 75 judges that although the treatment unit 9 of the coagulating/incising forceps 2 does not clamp the living tissue 80, power is fed. When the control mode is the output stop mode, the control unit 75 disables heating of all the heating elements 21a to 21c. When the control mode is the output restriction mode, the control unit 75 restricts heating of all the heating elements 21a to 21c to limit the temperature thereof to, for example, 100° C. (step S34). At the same time, the control unit 75 changes the lighting of the output state indicator LED 64 to flickering, and changes the continuous sounding of the buzzer 17c to intermittent sounding (step S35). Processing is then terminated. Consequently, when the control mode is the output stop mode, the temperatures tb and tc of the heating elements 21b and 21c decrease to a room temperature as indicated with a solid line in FIG. 22. When the control mode is the output restriction mode, the temperatures tb and tc gradually decrease to about 100° C. as indicated with a dashed line in FIG. 22.

When the average temperature Tave is equal to or lower than 110° C., the control unit 75 judges that the coagulating/incising forceps 2 is entirely used to clamp the living tissue 80 as shown in FIG. 18. The control unit 75 neither disables nor restricts power feed. Treating the living tissue 80 is continued until it is completed and the treatment unit 9 of the coagulating/incising forceps 2 no longer clamps the living tissue 80. At this time, the rise in the temperatures of the heating elements 21a to 21c remains as slow as indicated in FIG. 21.

As mentioned above, during a predetermined time T from the start of power feed, any heating element may have a difference in temperature from a heating element whose temperature is the lowest. Otherwise, a large difference in temperature may not be created between one heating element and the other heating elements, and an average of the temperatures of all the heating elements may reach a certain value or more. In this case, power feed to all the heating elements is stopped or restricted. Thus, power consumption of the coagulating/incising forceps 2 is suppressed or cooling the heat transfer plate 22 of the coagulating/incising forceps 2 after completion of power feed is facilitated.

Consequently, the heating treatment system 50 in accordance with the third embodiment can avoid wasting of electric energy or shorten the time required to cool the heat transfer plate 22 after completion of power feed.

(Fourth Embodiment)

Figure 24:
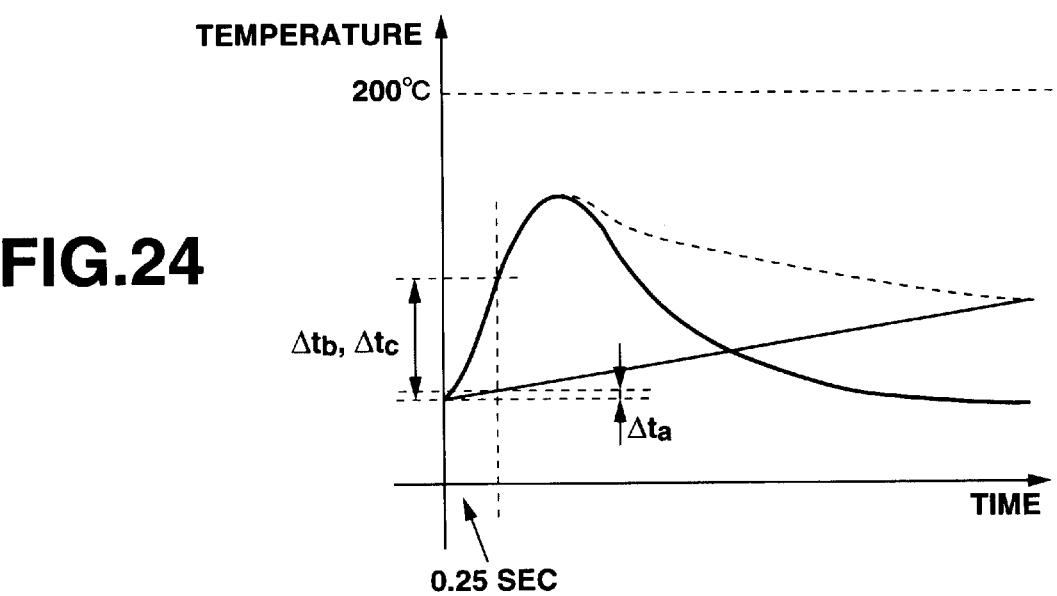
FIG. 24 is a graph indicating changes in the temperatures of heating elements occurring in the use situation shown in FIG. 17 due to the operation described in the flowchart of FIG. 23.
Figure 23:
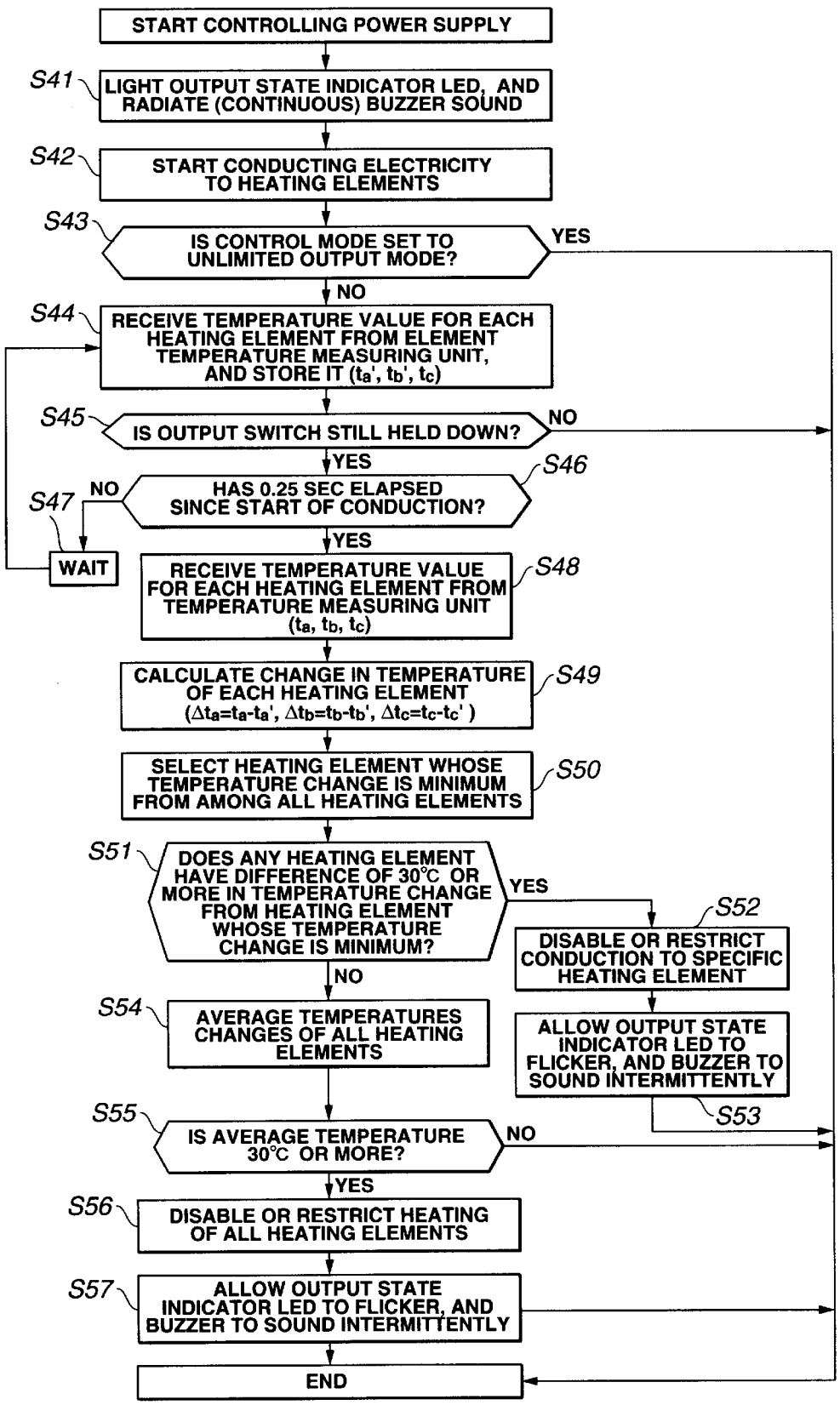
FIG. 23 is a flowchart for explaining operation by a heating treatment system in accordance with a fourth embodiment of the present invention.
Figure 25:
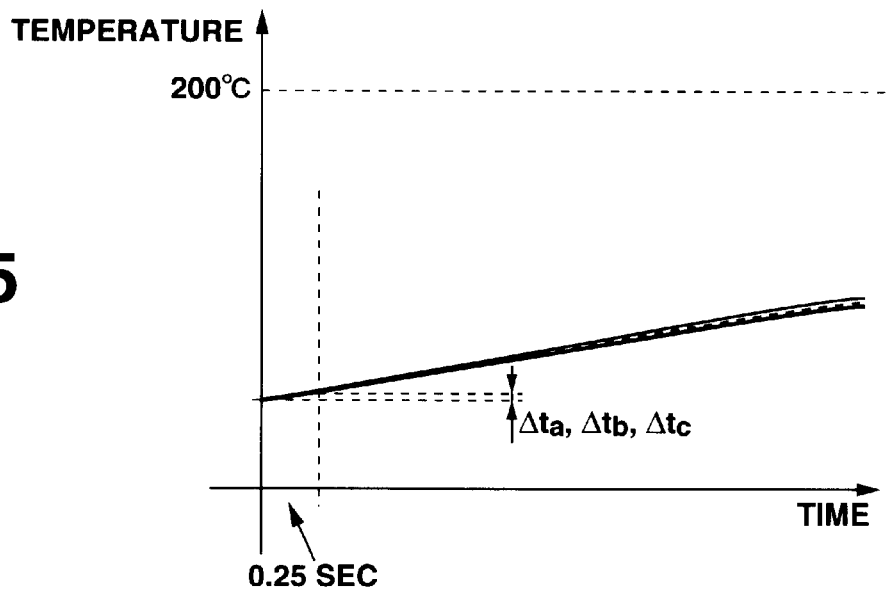
FIG. 25 is a graph indicating changes in the temperatures of the heating elements occurring in the use situation shown in FIG. 18 due to the operation described in the flowchart of FIG. 23.
Figure 26:
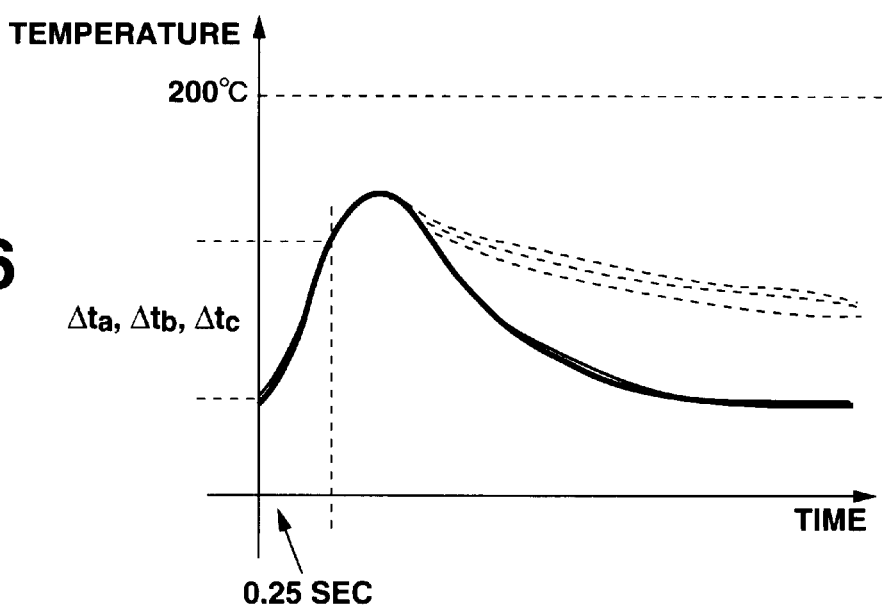
FIG. 26 is a graph indicating changes in the temperatures of the heating elements occurring in the use situation shown in FIG. 19 due to the operation described in the flowchart of FIG. 23.

FIG. 23 to FIG. 26 are concerned with a fourth embodiment of the present invention. FIG. 23 is a flowchart describing operation to be performed by a heating treatment system in accordance with the fourth embodiment of the present invention. FIG. 24 is a graph indicating changes in the temperatures of heating elements occurring in the use situation shown in FIG. 17 due to the operation described in the flowchart of FIG. 23. FIG. 25 is a graph indicating changes in the temperatures of the heating elements occurring in the use situation shown in FIG. 18 due to the operation described in the flowchart of FIG. 23. FIG. 26 is a graph indicating changes in the temperatures of the heating elements occurring in the use situation shown in FIG. 19 due to the operation described in the flowchart of FIG. 23.

According to the third embodiment, a difference in temperature between one heating element 21 and the other heating elements 21 is detected in order to judge the use situation of the treatment unit 9 signifying how the treatment unit 9 is used to clamp a living tissue. Thus, power feed to the heating elements 21 is controlled. According to the fourth embodiment, changes in the temperatures of the heating elements 21 or temperature change rates at which the temperatures of the heating elements change are detected in order to judge the use situation of the treatment unit 9 signifying how the treatment unit 9 is used to clamp a living tissue. Thus, power feed to the heating elements 21 is controlled. The other features are identical to those of the third embodiment, and the description of the features is omitted. The same reference numerals are assigned to components identical to those of the third embodiment.

A heating treatment system in accordance with the fourth embodiment is controlled by the control unit 75 according to a sequence described in the flowchart of FIG. 23. The sequence according to which the control unit 75 controls power feed will be described below.

The power switch 12 is turned on, whereby the whole heating treatment system is activated.

When the coagulating/incising forceps 2 is connected to the main unit 51, the state-of-element detecting units 71 (71a to 71d) judge whether the resistance values exhibited by the heating elements 21 (21a to 21d) to which channels are allocated fall within a range of normal values. The state-of-element detecting units 71 transmit the results of judgment to the control unit 75.

Based on the results of judgment received from the state-of-element detecting units 71 (71a to 71d), the control unit 75 enables electrical conduction to normal heating elements along allocated channels or disables electrical conduction to an abnormal heating element along an allocated channel. At the same time, the control unit 75 controls the indicator panel 38 to light in green the state-of-element indicator LEDs 63 (any of 63a to 63d) associated with the channels allocated to the normal heating elements. The control unit 75 puts out the state-of-element indicator LED 63 associated with the channel allocated to the abnormal or unconnected heating element Now, a description will be made of a case where the coagulating/incising forceps 2 in which, like the coagulating/incising forceps employed in the third embodiment, three heating elements 21 are incorporated are connected to the main unit.

Assume that the three heating elements 21a to 21c incorporated in the coagulating/incising forceps 2 are all normal. At this time, the state-of-element detecting units 71a to 71c judge that the heating elements 21a to 21c to which channels a, b, and c are allocated are normal, and the state-of-element detecting unit 71d judges that the heating element 21d is unconnected or disconnected.

The control unit 75 receives element-connected or unconnected signals from the state-of-element detecting units 71 (71a to 71d). Based on the signals, the control unit 75 enables electrical conduction along the channels a, b, and c but disables electrical conduction along the channel d. At the same time, the control unit 75 lights the state-of-element indicator LEDs 63a to 63c and puts out the state-of-element indicator LED 63d.

When the output switch 6c of the footswitch 6 is stepped on, the footswitch input unit 37 transmits an output start signal to the control unit 75 through the footswitch connector receptacle 18.

In response to the output start signal, the control unit 75 transmits a control signal to the output units 74a to 74c so as to instruct the control units 74 to conduct electricity to the heating elements 21a to 21c that are judged to be normal. The output units 74a to 74c start conducting electricity to the normal heating elements 21a to 21c (step S41). The heating elements 21a to 21c are then heated. At the same time, the control unit 75 lights the output state indicator LED 64 and sounds the buzzer 17c continuously (step S42).

At this time, as described in relation to the third embodiment, the three use situations shown in FIG. 17 to FIG. 19 are conceivable concerning how the treatment unit 9 of the coagulating/incising forceps 2 is used to clamp a living tissue.

FIG. 24, FIG. 25, and FIG. 26 are graphs indicating changes in the temperatures of the heating elements 21a to 21c occurring when heating is controlled based on the control sequence employed in the present embodiment with the heating elements put in the use situations shown in FIG. 17 to FIG. 19. Incidentally, solid lines in FIG. 24 and FIG. 26 alike indicate changes in the temperatures of the heating elements occurring when heating is disabled. Dashed lines therein indicate changes in the temperatures of the heating elements occurring when heating is restricted.

When the output switch 6c of the footswitch 6 is stepped on, the control unit 75 first checks whichever of the control modes, that is, the output stop mode, output restriction mode, and output non-restriction mode is selected using the control mode selection knob 62 (step S43). If the control mode is the output non-restriction mode, the control unit 75 skips the subsequent processing steps S44 to S57. Power feed is continued until the output switch 6c is released (the output switch 6c is still held down). Controlling power feed is terminated.

If the control mode is not the output non-restriction mode, that is, if the control mode is the output stop mode or output restriction mode, the control unit 75 receives information of the temperature values ta', tb', and tc from the temperature-of-element measuring units 72 (72a to 72d). The temperature values correspond respectively to the temperature of the heating elements 21a to 21c exhibited at the start of power feed. The control unit 75 stores the information in a memory (step S44).

When the output switch 6c is still held down (step S45), the control unit 75 uses the built-in timer, which is not shown, to measure the time that has elapsed since the start of power feed. After a predetermined time T (for example, 0.25 sec) has elapsed since the start of power feed (step S46 and step S47), the control unit 75 receives information of temperature values ta, tb, and tc from the temperature-of-element measuring units 72 (72a to 72c) (step S48). The temperature values correspond respectively to the temperature of the heating elements 21a to 21c exhibited in the predetermined time τ.

The control unit 75 subtracts the temperature values ta', tb', and tc' detected at the start of power feed from the temperature values ta, tb, and tc detected in the predetermined time τ. The control unit 75 thus calculates changes in the temperatures of the heating elements 21a to 21c Δta (=ta−ta'), Δtb (=tb−tb'), and Δtc (=tc−tc') (step S49).

The control unit 75 recognizes that the heating element 21a exhibits the smallest temperature change among the calculated temperature changes of the heating elements 21a to 21c Δta, Δtb, and Δtc (step S50). The control unit 75 then recognizes that the heating elements 21b and 21c have a difference in temperature change of, for example, 30° C. or more from the heating element 21a that exhibits the smallest temperature change (step S51).

When the control mode is the output stop mode, the control unit 75 disables heating of the identified heating elements 21b and 21c. When the control mode is the output restriction mode, the control unit 75 restricts heating of the heating elements 21b and 21c so as to limit the temperatures thereof to, for example, 100° C. (step S52). At the same time, the control unit 75 changes the lighting of the output state indicator LED 64 to flickering and changes the continuous sounding of the buzzer 17c to intermittent sounding (step S53). Processing is then terminated.

Incidentally, as seen from FIG. 24, the temperature ta of the heating element 21a rises slowly but the temperatures tb and tc of the heating elements 21b and 21c rise rapidly. At a certain time instant τ, the difference between ta and tb and tc reaches 30° C. or more.

The control unit 75 disables heating of the heating elements 21b and 21c. Consequently, when the control mode is the output stop mode, the temperatures tb and tc of the heating elements 21b and 21c decrease to a room temperature as indicated with a solid line in FIG. 24. When the control mode is the output restriction mode, the temperatures tb and tc thereof gradually decrease to about 100° C. as indicated with a dashed line in FIG. 24.

Consequently, in the use situation shown in FIG. 17 in which part of the treatment unit 9 of the coagulating/incising forceps 2 is used to clamp the living tissue 80, it is possible to heat only the heating element lying inside the portion of the treatment unit 9 clamping the living tissue 80.

No heating element may meet the condition, that is, no heating element may have a difference in temperature change of, for example, 30° C. or more from the heating element 21a that exhibits the smallest temperature change. In this case, the control unit 75 calculates an average value ΔTave of the temperature changes exhibited by all the heating elements 21a to 21c (step S54). The control unit 75 then compares the average value ΔTave with a predetermined temperature change (for example, 30° C.) (step S55).

If the average value ΔTave of the temperature changes is equal to or larger than 30° C., the control unit 75 judges that although the treatment unit 9 of the coagulating/incising forceps 2 does not clamp the living tissue 80 as shown in FIG. 19, power is fed.

When the control mode is the output stop mode, the control unit 75 disables heating of all the heating elements 21a to 21c. Moreover, when the control mode is the output restriction mode, the control unit 75 restricts heating of all the heating elements 21a to 21c so as to limit the temperatures of the heating elements 21a to 21c to, for example 100° C. (step S56). At the same time, the control unit 75 changes the lighting of the output state indicator LED 64 to flickering and changes the continuous sounding of the buzzer 17c to intermittent sounding (step S35). Processing is then terminated. Consequently, when the control mode is the output stop mode, the temperatures tb and tc of the heating elements 21b and 21c decrease to a room temperature as indicated with a solid line in FIG. 26. When the control mode is the output restriction mode, the temperatures tb and tc gradually decrease to about 100° C. as indicated with a dashed line in FIG. 26.

If the average value ΔTave of the temperature changes is equal to or smaller than 30° C., the control unit 75 judges that the treatment unit 9 of the coagulating/incising forceps 2 is entirely used to clamp the living tissue 80 as shown in FIG. 18, and that coagulation or incision is under way. The control unit 75 therefore neither disables nor restricts power feed. The treatment of the living tissue 80 is continued until it is completed and the treatment unit 9 of the coagulating/incising forceps 2 no longer clamps the living tissue 80. At this time, the temperatures of the heating elements 21a to 21c rise slowly as shown in FIG. 25. Controlling power feed is then terminated.

As mentioned above, according to the fourth embodiment, similarly to the third embodiment, it is inferred from a difference in temperature rise or a temperature change rate that a difference in temperature will occur. Before the difference in temperature between one heating element and the other heating elements reaches the value employed in relation to the third embodiment, power feed to heating elements can be stopped or restricted. The fourth embodiment can therefore provide the same advantages as those of the third embodiment or even improved advantages.

The fourth embodiment can provide, in addition to the same advantages as the third embodiment, the advantage of further power saving and further shortening of a cooling time.

(Fifth Embodiment)

Figure 27:
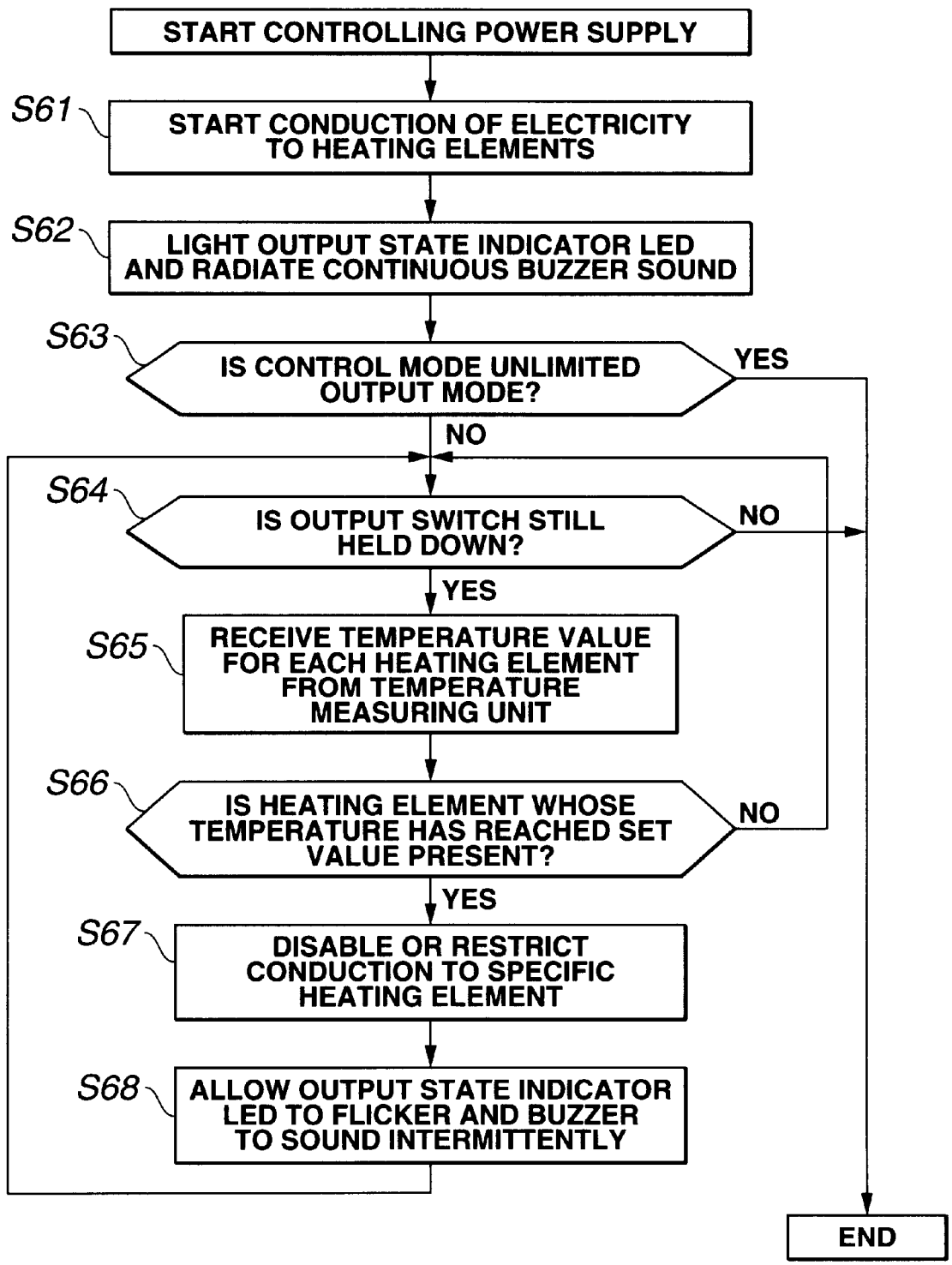
FIG. 27 is a flowchart for explaining operation to be performed by a heating treatment system in accordance with a fifth embodiment of the present invention.
Figure 28:
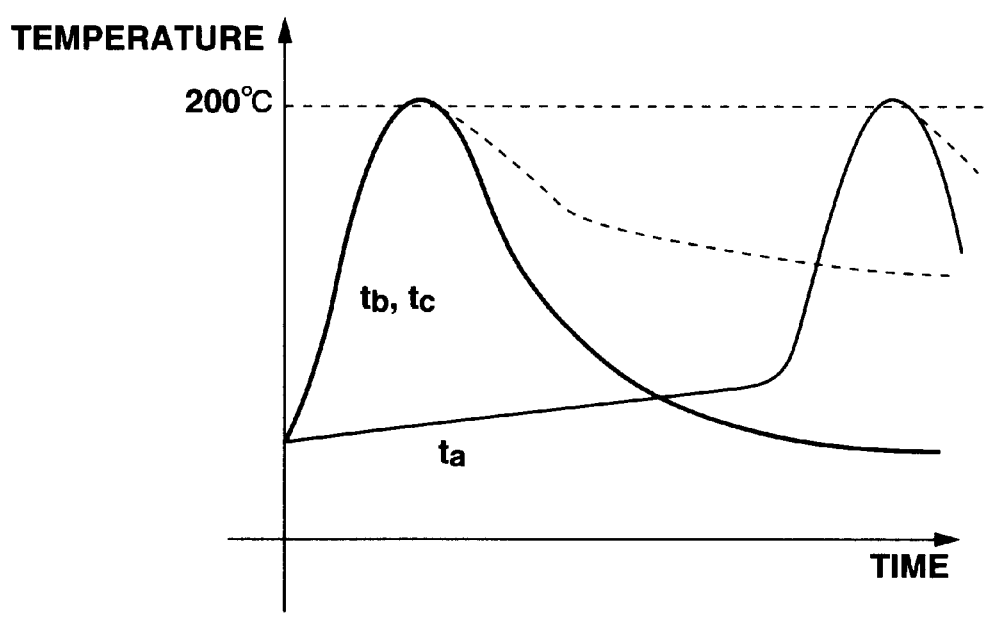
FIG. 28 is a graph indicating changes in the temperatures of heating elements occurring in the use situation shown in FIG. 17 due to the operation described in the flowchart of FIG. 27.

FIG. 27 and FIG. 28 are concerned with the fifth embodiment of the present invention. FIG. 27 is a flowchart describing operation to be performed by a heating treatment system in accordance with the fifth embodiment of the present invention. FIG. 28 is a graph indicating changes in the temperatures of heating elements occurring in the use situation shown in FIG. 17 due to the operation performed as described in the flowchart of FIG. 27.

According to the fourth embodiment, changes in the temperatures of the heating elements 21 are detected in order to judge a use situation signifying how the treatment unit 9 is used to clamp a living tissue. Power feed to the heating elements 21 is thus controlled. According to the fifth embodiment, a heating element whose temperature has reached a set value is detected in order to judge the use situation of the treatment unit 9 signifying how the treatment unit 9 is used to clamp a living tissue. Power feed to the heating elements 21 is thus controlled. The other features are identical to those of the third embodiment, and the description of the features is omitted. The same reference numerals are assigned to components identical to those of the third embodiment.

A sequence according to which the control unit 75 controls power feed will be described in conjunction with the flowchart of FIG. 27.

The power switch 12 is turned on, whereby the heating treatment system is activated.

When the coagulating/incising forceps 2 is connected to the main unit 51, the state-of-element detecting units 71 ($71a$ to 71d) judge, as mentioned in relation to the third embodiment, whether the resistance values exhibited by the heating elements 21 (21a to 21d), to which channels are allocated, fall within a range of normal values. The state-of-element detecting units 71 transmit the results of judgment to the control unit 75.

Based on the results of judgment received from the state-of-element detecting units 71, the control unit 75 enables electrical conduction to normal heating elements along allocated channels or disables electrical conduction to an abnormal heating element along an allocated channel. At the same time, the control unit 75 controls the indicator panel 38 so as to light in green the state-of-element indicator LEDs 63 (any of 63a to 63d) associated with the channels allocated to the normal heating elements. The control unit 75 puts out the state-of-element indicator LED 63 associated with the channel allocated to the abnormal or unconnected heating element.

Now, a description will be made of a case where three heating elements 21 are incorporated in the coagulating/incising forceps 2 as it is in the third embodiment.

Assume that the three heating elements 21a to 21c incorporated in the coagulating/incising forceps 2 are all normal.

At this time, the state-of-element detecting units 71a to 71c judge that the heating elements 21a to 21c to which channels a, b, and c are allocated are normal. The state-of-element detecting unit 71d judges that the heating element 21d to which a channel d is allocated is unconnected or disconnected.

The control unit 75 receives element-connected or unconnected signals from the state-of-element detecting units 71 (71a to 71d). Based on the received signals, the control unit 75 enables electrical conduction along the channels a, b, and c and disables electrical conduction along the channel d. At the same time, the control unit 75 lights the state-of-element indicator LEDs 63a to 63c and puts out the state-of-element indicator LED 63d.

When the output switch 6c of the footswitch 6 is stepped on, the footswitch input unit 37 transmits an output start signal to the control unit 75 through the footswitch connector receptacle 18.

In response to the output start signal, the control unit 75 transmits a control signal to the output units 74a to 74c so as to instruct the output units to conduct electricity to the heating elements 21a to 21c that are judged to be normal. The output units 74a to 74c start electrical conduction to the normal heating elements 21a to 21c (step S61). Consequently, the heating elements 21a to 21c are heated. At the same time, the control unit 75 lights the output state indicator LED 64 and sounds the buzzer 17c continuously (step S62).

FIG. 28 is a graph indicating changes in the temperatures of the heating elements 21a to 21c occurring when heating is controlled according to the control sequence employed in the present invention with the heating elements put in the use situation shown in FIG. 17. Solid lines in FIG. 28 indicate the changes in the temperatures of the heating elements occurring when heating is disabled. Dashed lines therein indicate the changes in the temperatures of the heating elements occurring when heating is restricted.

When the output switch 6c of the footswitch 6 is stepped on, the control unit 75 first checks whichever of the control modes, that is, the output stop mode, output restriction mode, and output non-restriction mode is selected using the control mode selection knob 62 (step S63). When the control mode is the output restriction mode, the control unit 75 skips the subsequent processing steps S64 to S68. Power feed is continued until the output switch 6c is released (the output switch 6c is still held down). Controlling power feed is terminated.

When the control mode is not the output non-restriction mode, that is, the control mode is the output stop mode or the output restriction mode, while the output switch 6c is held down, the control unit 75 monitors the temperatures of the heating elements 21a to 21c (step S64 to step S66).

First, the control unit 75 receives the temperature values exhibited by the heating elements 21a to 21c from the temperature-of-element measuring units 72 (72a to 72c) (step S65).

The control unit 75 then compares the temperatures of the heating elements 21a to 21c with the set temperature values (step S66).

Herein, if the temperature of any heating element has reached the set temperature value, the control unit 75 judges that the heating element lies inside the portion of the treatment unit 9 that does not clamp the living tissue 80. Otherwise, the control unit 75 judges that the heating-element lies inside the portion of the treatment unit 9 that was used to clamp the living tissue 80 but is now unused to clamp it because the living tissue 80 has been incised and separated from the heat transfer plate 22. When the control mode is the output stop mode, the control unit 75 disables heating of the heating element. Moreover, when the control mode is the output restriction mode, the control unit 75 restricts heating of the heating element so as to limit the temperature of the heating element to, for example, 100° C. (step S67). At the same time, the control unit 75 changes the lighting of the output state indicator LED 64 to flickering and changes the continuous sounding of the buzzer 17*c* to intermittent sounding (step S68). Processing is then terminated.

In contrast, if the temperature of any heating element has not reached the set temperature value, the control unit 75 judges that coagulation or incision is under way. The control unit 75 neither disables nor restricts power feed to the heating element. The processing steps S64 to S66 are repeated while the output switch 6*c* is held down.

In the use situation shown in FIG. 17, the heating elements 21*b* and 21*c* lie inside the portion of the treatment unit 9 that does not clamp the living tissue 80. The temperatures of the heating elements 21*b* and 21*c* rise to the set temperature value immediately after the start of power feed by the output units 74*b* and 74*c*. The control unit 75 therefore disables or restricts electrical conduction to the heating elements 21*b* and 21*c*. Consequently, when the control mode is the output stop mode, the temperatures tb and tc of the heating elements 21*b* and 21*c* decrease as indicated with a solid line in FIG. 28. When the control mode is the output restriction mode, the temperatures tb and tc of the heating elements 21*b* and 21*c* gradually decrease to about 100° C. as indicated with a dashed line in FIG. 28.

The heating element 21*a* lies inside the portion of the treatment unit that clamps the living tissue 80. The temperature of the heating element 21*a* is therefore low immediately after the start of power feed from the output unit 74*a*. Immediately after coagulation or incision is completed and the living tissue 80 is separated from the heat transfer plate 22, the temperature of the heating element 21*a* rises sharply and reaches the set temperature value. When the temperature of the heating element 21*a* reaches the set temperature value, the control unit 75 disables or restricts electrical conduction to the heating element 21*a*. Consequently, when the control mode is the output stop mode, the temperature ta of the heating element 21*a* decreases to a room temperature as indicated with a solid line in FIG. 28. When the control mode is the output restriction mode, the temperature ta of the heating element 21*a* gradually decreases to about 100° C. as indicated with a dashed line in FIG. 28.

As mentioned above, when part of the heat transfer plate 22 is used to clamp the living tissue 80, power feed to heating elements that lie inside the portion of the heat transfer plate 22 which does not clamp the living tissue 80 can be stopped or restricted. Moreover, power feed to a heating element that lies inside the portion of the heat transfer plate 22 which was used to clamp the living tissue 80 but is now unused because of completion of coagulation or incision can be stopped or restricted. Consequently, wasting of electrical energy by the coagulating/incising forceps 2 can be avoided, and the time required to cool the heat transfer plate 22 after completion of power feed can be shortened.

Namely, the temperature of a heating element that lies inside the portion of the heat transfer plate unused to clamp the living tissue 80 rises up to a set value. Moreover, the temperature of a heating element that lies inside the portion of the heat transfer plate which was used to clamp the living tissue 80 but is now unused because of completion of coagulation or incision rises up to a set temperature value. Making the most of these facts, according to the present embodiment, power feed to such a heating element is stopped or restricted in order to suppress power consumption by the coagulating/incising forceps 2. Moreover, cooling of the heat transfer plate 22 incorporated in the coagulating/incising forceps after completion of power feed can be facilitated.

Consequently, the fifth embodiment provides, in addition to the same advantages as those of the third and fourth embodiments, the advantage of further power saving. Moreover, the time required for cooling after completion of power feed can be shortened.

As described so far, according to the present invention, there is provided a heating treatment system capable of treating a lesion on a stable basis by producing an appropriate distribution of temperature values in a treatment unit of any shape.

In general, a therapeutic instrument is used to incise or coagulate a living tissue or arrest bleeding during a surgical or an internal operation. The therapeutic instrument has a therapeutic energy applying means, which generates therapeutic energy with which a living tissue is treated, incorporated therein. The therapeutic energy generated by the therapeutic energy applying means is applied to the living tissue in order to incise or coagulate the living tissue or arrest bleeding from the living tissue.

The therapeutic instrument is freely detachably attached to a therapeutic instrument control apparatus. Driving energy fed from the therapeutic instrument control apparatus is used to drive or control the therapeutic energy applying means. The therapeutic instrument and therapeutic instrument control apparatus constitute a medical treatment system.

Various proposals have been made of the medical treatment system in the past.

For example, a medical treatment system described in Japanese Patent No. 2578250 is an ultrasonic treatment system consisting mainly of a handpiece and a therapeutic instrument control apparatus. The handpiece serves as a therapeutic instrument and has ultrasonic transducers, which generate ultrasonic waves, incorporated therein. The handpiece can be connected to the therapeutic instrument control apparatus so that the handpiece can be disconnected freely. The therapeutic instrument control apparatus drives or controls the ultrasonic transducers incorporated in the handpiece.

Moreover, a medical treatment system described in Japanese Unexamined Patent Application Publication No. 2000-250 is an electric cautery system consisting mainly of an electric cautery and a therapeutic instrument control apparatus. The electric cautery serves as a therapeutic instrument and has electrodes through which high-frequency current flows out. The electric cautery can be connected to the therapeutic instrument control apparatus so that the electric cautery can be disconnected freely. The therapeutic instrument control apparatus drives or controls the electrodes of the electric cautery.

In the medical treatment systems described in the Japanese Patent No. 2578250 and Japanese Unexamined Patent Application Publication No. 2000-250, an output means that transmits an identification signal with which the type of handpiece or the type of the electrodes of the electric cautery is identified is incorporated in the handpiece or electric cautery. In the therapeutic instrument control apparatus to which the handpiece or electric cautery is connected, a detecting means detects the type of handpiece or the type of electrodes of the electric cautery, and power feed is controlled based on the result of the detection.

However, the medical treatment systems described in the Japanese Patent No. 2578250 and Japanese Unexamined Patent Application Publication No. 2000-250 have a drawback that it is impossible to recognize an error in the identification signal transmitted from the output means incorporated in the handpiece or electric cautery or an error made by the detecting means incorporated in the therapeutic instrument control apparatus.

The present invention attempts to break through the foregoing situation. In order to provide a medical treatment system, a therapeutic instrument, and a therapeutic instrument control apparatus capable of accurately judging the type of therapeutic instrument and feeding power, the present invention provides embodiments described below.

The embodiments realize a medical treatment system capable of accurately identifying the type of therapeutic instrument and feeding power, a therapeutic instrument, and a therapeutic instrument control apparatus.

(Sixth Embodiment)

Figure 29:
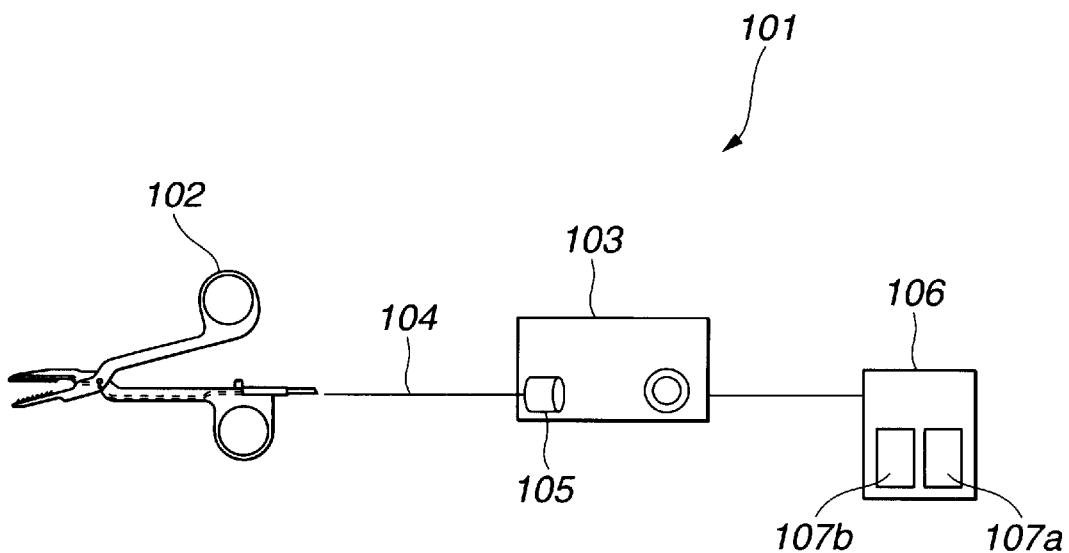
FIG. 29 shows the overall configuration of a medical treatment system in accordance with a sixth embodiment of the present invention.
Figure 30A:
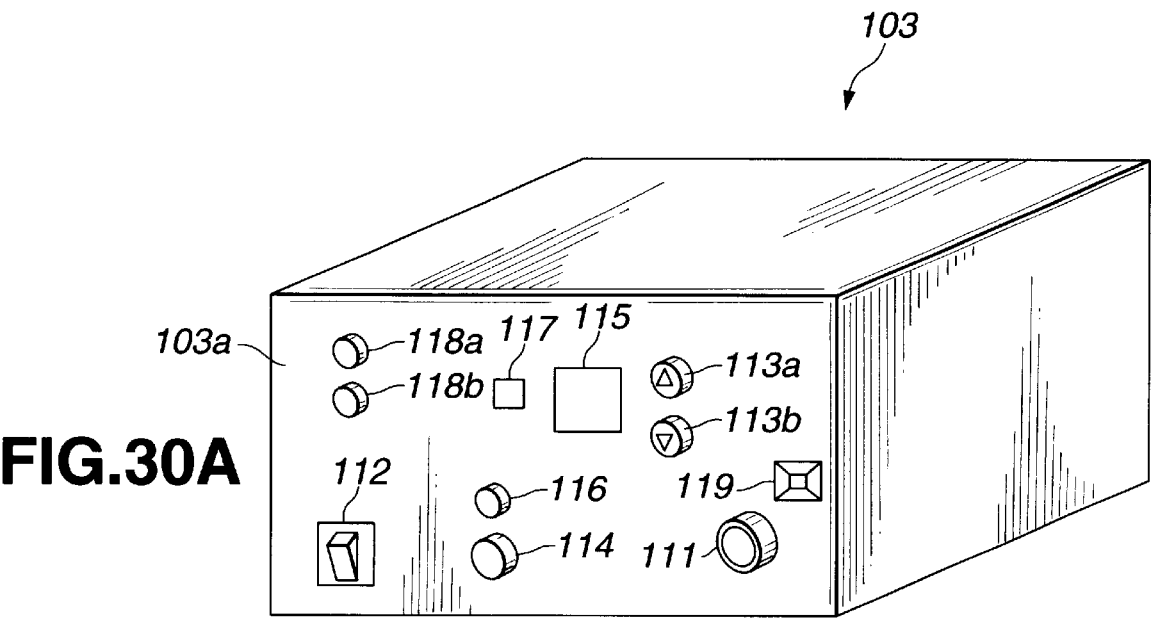
FIG. 30A is a perspective view showing the appearance of a therapeutic instrument control apparatus that is included in the medical treatment system shown in FIG. 29 and that is seen from the front panel thereof.
Figure 30B:
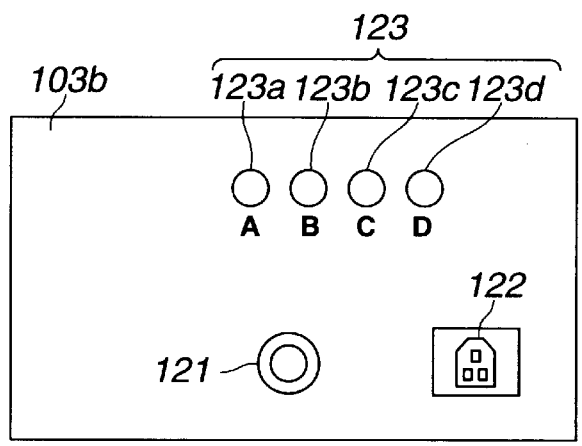
FIG. 30B is a rear view showing the back of the therapeutic instrument control apparatus shown in FIG. 30A.
Figure 31:
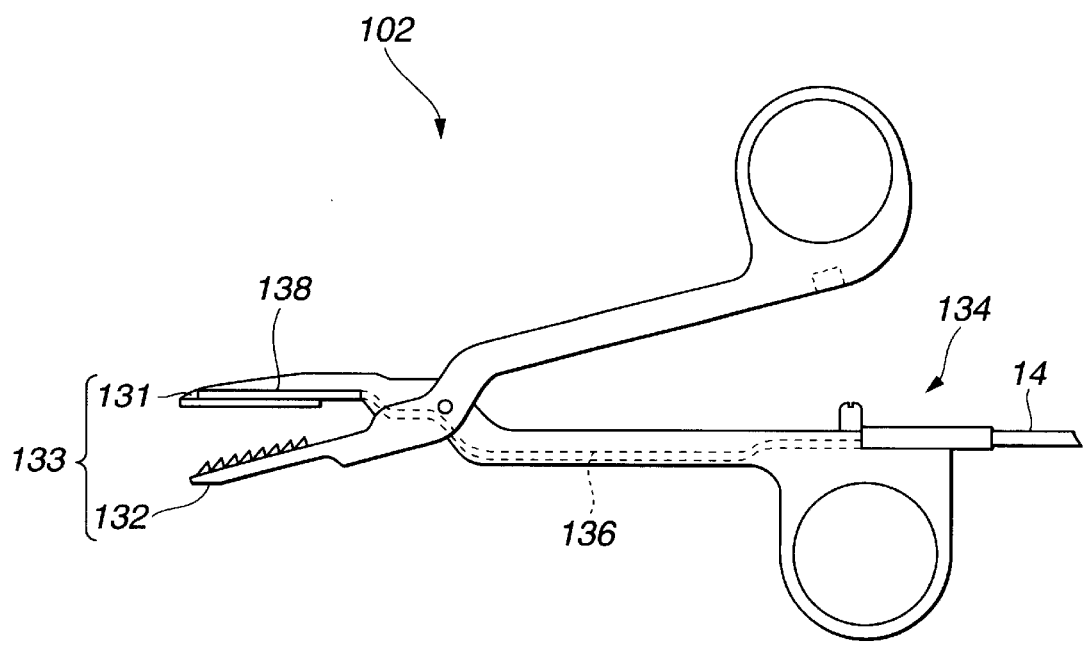
FIG. 31 is an explanatory diagram showing a therapeutic instrument included in the medical treatment system shown in FIG. 29.
Figure 32:
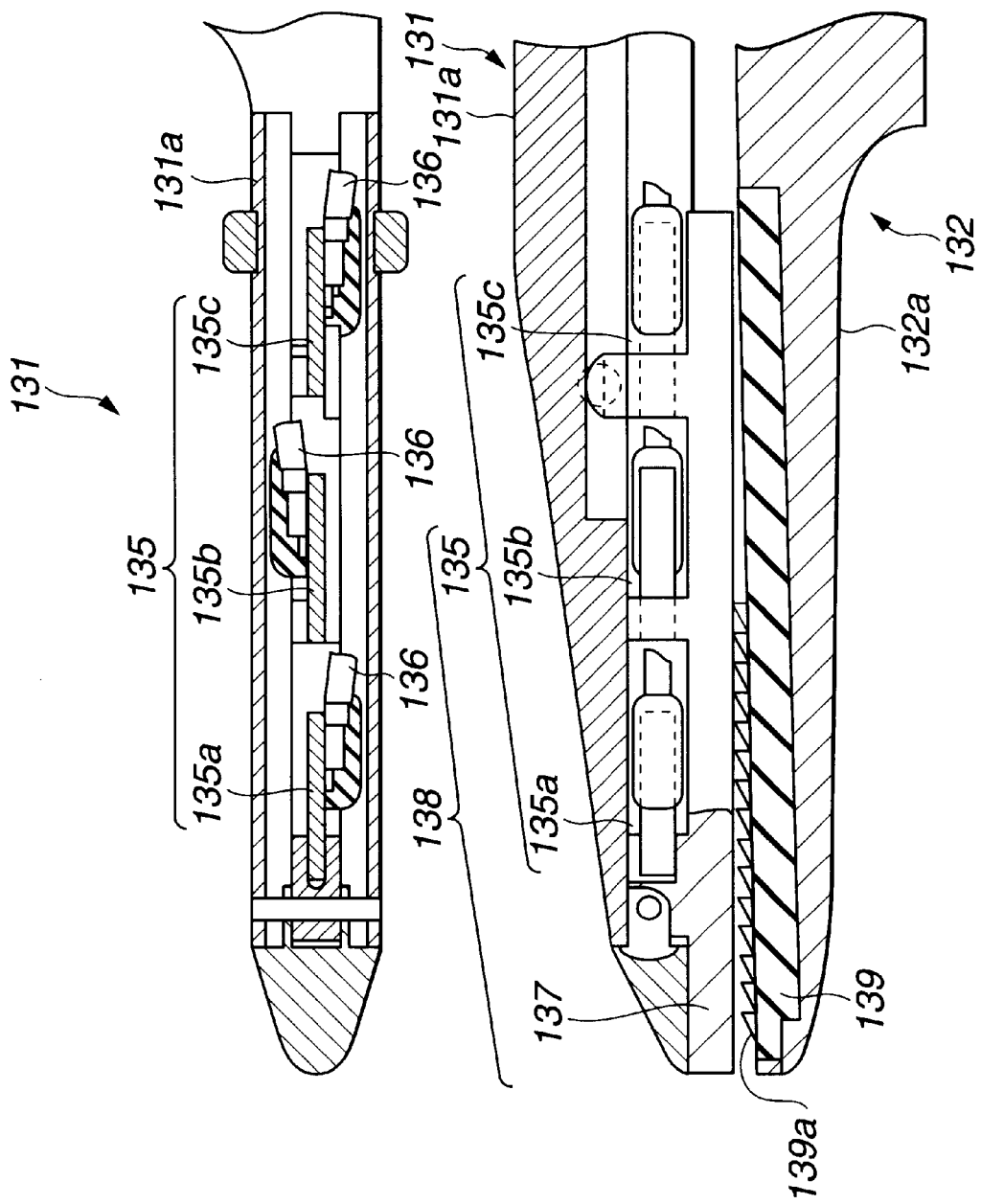
FIG. 32A is a top sectional view showing a treatment unit of the therapeutic instrument shown in FIG. 31 which is seen from the top thereof.
FIG. 32B is a side sectional view showing the treatment unit shown in FIG. 32A and seen from the lateral side thereof.
Figure 33:
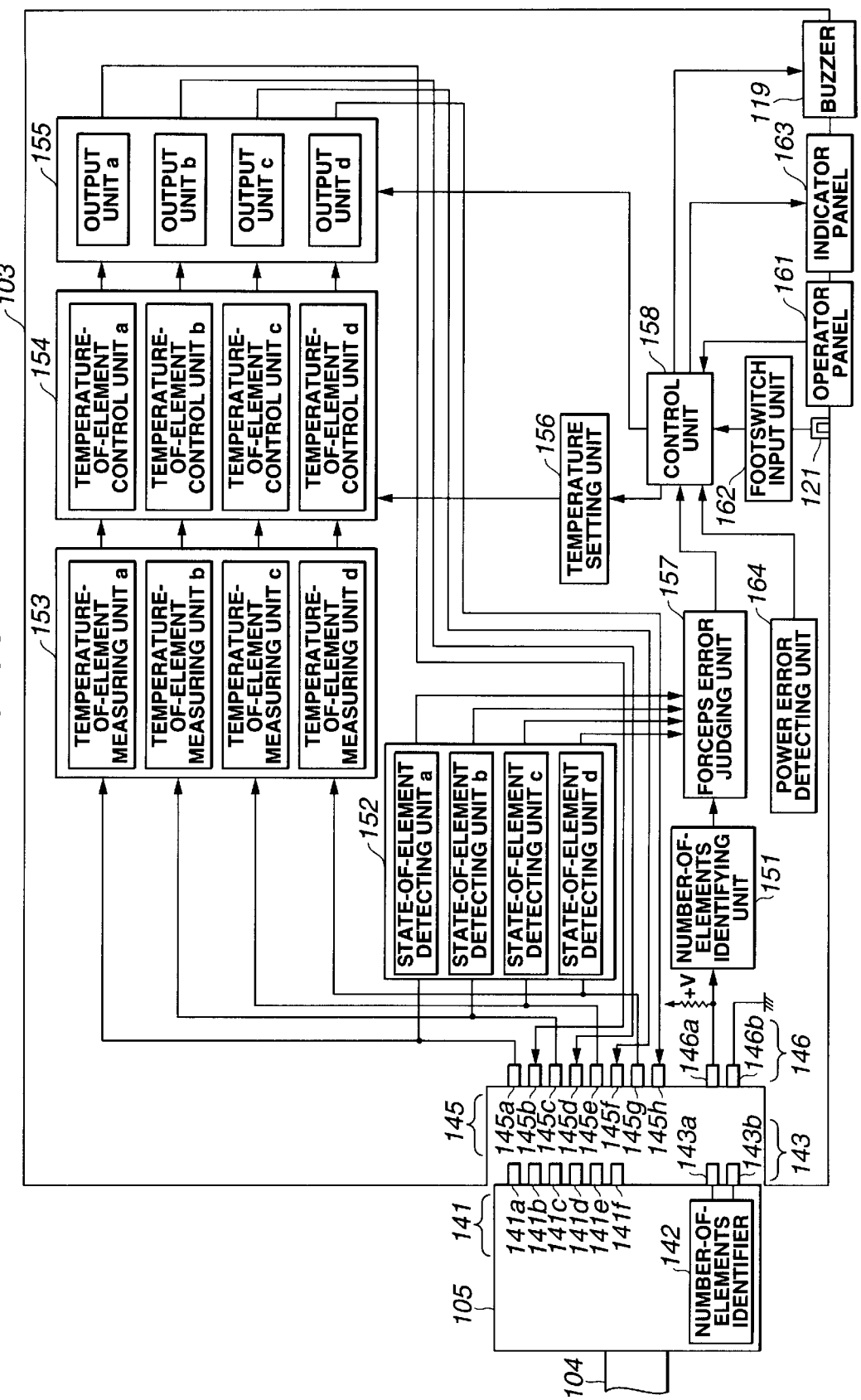
FIG. 33 is a circuit block diagram for explaining a medical treatment system in accordance with a sixth embodiment of the present invention.

FIG. 29 to FIG. 33 are concerned with a sixth embodiment of the present invention. FIG. 29 shows the overall configuration of a medical treatment system in accordance with the sixth embodiment of the present invention. FIG. 30A and FIG. 30B show the appearance of a therapeutic instrument control apparatus included in the medical treatment system shown in FIG. 29. FIG. 30A is a perspective view showing the therapeutic instrument control apparatus seen from the front panel thereof. FIG. 30B shows the appearance of the back panel of the therapeutic instrument control apparatus. FIG. 31 is an explanatory diagram showing a therapeutic instrument included in the medical treatment system shown in FIG. 29. FIG. 32A and FIG. 32B are explanatory sectional views showing the treatment unit of the therapeutic instrument shown in FIG. 31. FIG. 32A is a top sectional view showing the treatment unit of the therapeutic instrument seen from the upper side thereof. FIG. 32B is a side sectional view showing he treatment unit of the therapeutic instrument seen from the lateral side thereof. FIG. 33 is a circuit block diagram for explaining the medical treatment system in accordance with the sixth embodiment of the present invention.

A medical treatment system 1 in accordance with the present embodiment consists mainly of, as shown in FIG. 29, coagulating/incising forceps 102 and a therapeutic instrument control apparatus 103. The coagulating/incising forceps 102 serves as a therapeutic instrument and have a plurality of heating elements, which will be described later, incorporated therein. The coagulating/incising forceps 102 can be connected to the therapeutic instrument control apparatus 103 so that the coagulating/incising forceps can be disconnected freely. The therapeutic instrument control apparatus 103 feeds power (electric energy) to the heating elements incorporated in the coagulating/incising forceps 102, and drives and controls the heating elements.

The coagulating/incising forceps 102 has a connector 105 attached to the rear end of a connection cable 104 that extends from the coagulating/incising forceps 102. The connector 105 is coupled to the therapeutic instrument control apparatus 103 so that it can be uncoupled freely. The number of heating elements incorporated in the coagulating/incising forceps 102 varies depending on the type of forceps suitable for a purpose of treatment. An identifier that indicates the number of heating elements as described later is incorporated in the connector 105.

A footswitch 106 can be connected to the therapeutic instrument control apparatus 103. The footswitch 106 serves as an input means for use in inputting an instruction that is transmitted to a heating means incorporated in the coagulating/incising forceps 102. The footswitch 106 has two switches, that is, a maximum temperature level output switch 107a and a designated temperature level output switch 107b. According to the present embodiment, since the footswitch 106 has the two switches of the maximum temperature level output switch 107a and designated temperature level output switch 107b, power can be fed immediately without the necessity of changing two temperature values optimized for purposes of treatment.

As shown in FIG. 30A and FIG. 30B, the therapeutic instrument control apparatus 103 has a front panel 103a and a back panel 103b.

Referring to FIG. 30A, the front panel 103a has a connector receptacle 111 to which the connector 105, attached to the cable extending from the coagulating/incising forceps 102, can be connected so that it can be freely disconnected from the receptacle 111. The front panel 103 has a power switch 112, a temperature level up switch 113a, a temperature level down switch 113b, and a standby switch 114. The power switch 112 is used to turn on or off the power supply. The temperature level up switch 113a and temperature level down switch 113b are used to designate a temperature level that determine the temperature values of heating elements incorporated in the coagulating/incising forceps 102. The standby switch 114 is used to make a transition from a standby state to an output enabled state. Moreover, the front panel 103a has a temperature level indicator LED 115, a standby indicator LED 116, an output indicator LED 117, a forceps error indicator LED 118a, and a power error indicator LED 118b. The temperature level indicator LED 115 indicates a temperature level designated using the temperature level up switch 113a and temperature level down switch 113b. The standby indicator LED 116 is lit when power feed is disabled, thus indicating establishment of a standby state. The output indicator LED 117 indicates that electricity is being conducted to the heating elements incorporated in the coagulating/incising forceps 102. The forceps error indicator LED 118a is lit when the coagulating/incising forceps 102 is abnormal. The power error indicator LED 118b is lit when any internal circuit is abnormal. Furthermore, the front panel 103a has a buzzer 119 that radiates a warning sound.

Referring to FIG. 30B, the back panel 103b has a footswitch connector receptacle 121 and a power supply inlet 122. Moreover, the back panel 103b has state-of-element indicator LEDs 123 (123a to 123d) that indicate the states of the heating elements incorporated in the coagulating/incising forceps 102. The state-of-element indicator LED 123 is lit in green when an associated heating element incorporated in the coagulating/incising forceps 102 is normal, and lit in red when the associated heating element is abnormal. When the associated heating element is unconnected, the state-of-element indicator LED 123 is unlit. The coagulating/incising forceps 102 having up to four heating elements incorporated therein can be connected to the therapeutic instrument control apparatus 103 employed in the present embodiment.

As shown in FIG. 31, the coagulating/incising forceps 102 consists mainly of a clamping unit 133 and a handle pair 134. The clamping unit 133 includes a stationary blade 131 and a movable blade 132 capable of approaching to or receding from the stationary blade 131, and clamps a living tissue. The handle pair 134 is opened or closed in order to clamp a living tissue using the clamping pair 133. The connection cable 104 extends from the proximal end of the handle pair 134.

The stationary blade 131 has, as shown in FIG. 32A, for examples three heating elements 135 (135a to 135c) incorporated therein. The heating element 135 is a thin-film resistor formed on, for example, a ceramic plate. One end of a coaxial lead 136 over which electricity is conducted is coupled to the heating element 135, and the other end of the coaxial lead 136 is spliced to the end of the connection cable 104. The coaxial lead 136 is coupled to a connector pin of the connector 105 that will be described later.

The heating elements 135 are, as shown in FIG. 32B, thermally coupled to a heating plate 137, whereby a heating treatment member 138 is constructed. Heat dissipated from the heating elements 135 is transferred to the heating plate 137.

The movable blade 132 is composed of an elastic member 139 having a sawtooth 139a and a main body 132. The sawtooth 139a cooperates with the heating plate 137 of the stationary blade 131 in clamping a living tissue. When the handle pair 134 is closed, the movable blade 132 approaches to the stationary blade 131. Consequently, the heating plate 137 of the stationary blade 131 and the sawtooth 139a of the movable blade 132 elastically clamp a living tissue. The living tissue sandwiched between the heating plate 137 and elastic member 139 is coagulated or incised with heat transferred from the heating plate 137.

Referring to FIG. 33, the connector 105 has connector pins 141 (141a to 141f) to which the other ends of the coaxial leads 136 are coupled. The connector pins 141 are fitted in the connector receptacle 111 formed in the therapeutic instrument control apparatus 103. Moreover, the connector 105 includes a number-of-elements identifier 142 that indicates the number of heating elements 135. What is referred to as the number-of-elements identifier is an electrically resistive element that exhibits a predetermined resistance value proportional to the number of heating elements. The number-of-elements identifier 142 can be coupled to the connector receptacle 11 of the therapeutic instrument control apparatus 103 through connector pins 143 (143a and 143b).

According to the present embodiment, when the connector 105 is joined to the connector receptacle 111 of the therapeutic instrument control apparatus 103, the number-of-elements identifier 142 is identified through the connector pins 143. Moreover, the connector pins 141 are checked to see if the heating elements 135 are connected. The number of heating elements 135 is compared with the number of heating elements 135 connected to the connector pins 141, whereby it is judged whether the heating elements 135 can work normally. Based on the judgment, output units that will be described later are controlled.

Next, the internal components of the therapeutic instrument control apparatus 103 will be described below.

The therapeutic instrument control apparatus 103 is designed to accept the coagulating/incising forceps 102 having, for example, up to four heating elements 135.

The therapeutic instrument control apparatus 103 has the connector receptacle 111 in which pins 145 (145a to 145h) and pins 146 (146a and 146b) are included. The pins 145 are joined to the connector pins 141 included in the connector 105, while the pins 146 are joined to the connector pins 143 included in the connector 105. The pin 146a is connected to a reference voltage line V and to a number-of-elements identifying unit 151 that identifies the number of heating elements 135. The pin 146b is grounded. When the connector pins 143 of the connector 105 are joined to the pins 146, a current proportional to a resistance exhibited by the number-of-elements identifier 142 is induced by the reference voltage line V and flows into a ground. This brings about a voltage drop. The number-of-elements identifying unit 151 detects the voltage drop, and calculates the resistance value exhibited by the number-of-elements identifier 142 from the detected voltage drop. The number-of-elements identifying unit 151 identifies the number of heating elements according to a predetermined method of working out the number of heating elements from the calculated resistance value.

According to the method of working out the number of heating elements, when the resistance value exhibited by the number-of-elements identifier 142 is equal to or larger than 1 k$\Omega$ and less than 10 k$\Omega$, the number of heating elements is regarded to be 1. When the resistance value is equal to or larger than 10 k$\Omega$ and less than 20 k$\Omega$, the number of heating elements is regarded to be 2. When the resistance value is equal to or larger than 20 k$\Omega$ and less than 30 k$\Omega$, the number of heating elements is regarded to be 3. When the resistance value is equal to or larger than 30 k$\Omega$ and less than 40 k$\Omega$, the number of heating elements is regarded to be 4. When the resistance value is equal to or larger than 40 k$\Omega$, it is regarded that the forceps are unconnected.

The therapeutic instrument control apparatus 103 includes the number-of-elements identifying unit 151, state-of-element detecting units 152 (152a to 152d), temperature-of-element measuring units 153 (153a' to 153d), temperature-of-element control units 154 (154a to 154d), output units 155 (155a to 155d), a temperature setting unit 156, a forceps error judging unit 157, and a control unit 158. The state-of-element detecting units 512 detect whether the states of the heating elements 135 are normal. The temperature-of-element measuring units 153 measure the temperatures of the heating elements 135. The temperature-of-element control units 154 each compare a value measured by the temperature-of-element measuring unit 153 with an input set value, and thus control power feed to an associated heating element 135 independently of one another. The output units 155 (155a to 155d) feed power (electric energy) in response to control signals sent from the temperature-of-element control units 154. The temperature setting unit 156 transmits a designated temperature level to the temperature-of-element control units 154. The forceps error judging unit 157 compares the number of heating elements 135 detected by the state-of-element detecting units 152 with the number of heating elements 135 identified by the number-of-elements identifying unit 151, and recognizes occurrence of an error. Based on the result of recognition provided by the forceps error judging unit 157, the control unit 158 controls the temperature setting unit 156 and output units 155. When the number of heating elements 135 incorporated in the coagulating/incising forceps 2 is three or less, channels are allocated to the heating elements in order.

The temperature-of-element measuring unit 153 measures the temperature of an associated heating element 135 by using the fact that the resistance value exhibited by the heating element 135 varies depending on temperature. Specifically, the temperature-of-element measuring unit 153 serves as a resistance value detecting facility and measures a current or voltage, which flows into or is applied to the heating element 135, because the current or voltage varies depending on the resistance value exhibited by the heating element 135. The temperature-of-element measuring unit 153 thus detects the resistance value exhibited by the heating element 135, and calculates the temperature of the heating element 135 from the detected resistance value.

The state-of-element detecting unit 152 serves as a resistance value detecting facility similarly to the temperature-of-element measuring unit 153. The state-of-element detecting unit 152 detects the resistance value exhibited by an associated heating element 135 by measuring a current or voltage that flows into or is applied to the heating element. The state-of-element detecting unit 152 then judges whether the detected resistance value falls within a predetermined range of normal values. For example, when the measured resistance value falls within a range from 10 Ω to 100 Ω, the state-of-element detecting unit 152 judges that the heating element is normal. When the measured resistance value falls outside the range from 10 Ω to 100 Ω, the state-of-element detecting unit 152 judges that the heating element is abnormal. The state-of-element detecting unit 152 transmits the result of the detection to the forceps error judging unit 157.

The control unit 158 sets a maximum temperature level or a designated temperature level, which is designated using an operator panel 161 or transmitted from the footswitch 106 via the footswitch input unit 162, for the temperature setting unit 156. What is referred to as the operator panel 161 is a generic term for various switches including the temperature level up switch 113a exposed on the front panel 103a of the therapeutic instrument control apparatus 103. Moreover, various indicator LEDs exposed on the front panel 103a and back panel 103b of the therapeutic instrument control apparatus 103 are generically termed an indicator panel 163. Moreover, the control unit 158 is connected to a power error detecting unit 164. The power error detecting unit 164 detects an abnormal circuit, an error signal is sent from the power error detecting unit 164 to the control unit 158. The control unit 158 then lights the forceps error indicator LED 118a and sounds the buzzer 119.

Referring to FIG. 33, operations to be exerted by the medical treatment system 101 having the foregoing components will be described in conjunction with Table 4 to Table 6.

First, the power switch 112 is turned on, whereby the medical treatment system 101 is activated.

The temperature level up switch 113a and temperature level down switch 113b are used to designate a temperature level. The designated temperature level may be any of five levels of level 1 to level 5. Levels 1 to 5 are predetermined at intervals of 10° C. within a range from 160° C. to 200° C.

When the connector 105 attached to the cable extending from the coagulating/incising forceps 102 is not joined to the connector receptacle 11 of the therapeutic instrument control apparatus 103, the reference voltage V does not drop. It is therefore detected that the connector 105 is not joined. In this case, the control unit 158 lights the forceps error indicator LED 118a exposed on the front panel 103a, and puts out all the state-of-element indicator LEDs 123a to 123d. At this time, the control unit 148 does not sound the buzzer 119.

When the connector 105 attached to the cable extending from the coagulating/incising forceps 102 is joined to the connector receptacle 111 of the therapeutic instrument control apparatus 103, the reference voltage V drops in proportion to the resistance exhibited by the number-of-elements identifier 142. Based on the voltage drop, the number-of-elements identifying unit 151 calculates the resistance value exhibited by the number-of-elements identifier 142 and consequently identifies the number of heating elements incorporated in the coagulating/incising forceps 102.

The state-of-element detecting unit 152 detects whether the resistance value exhibited by an associated heating element 135 falls within the range of normal values. At this time, the resistance value measured on a channel that is allocated to no heating element 135 or that is allocated to a disconnected heating element exceeds the normal range. The resistance value measured on a channel that is allocated to a short-circuited heating element falls below the normal range.

A description will be made on the assumption that three heating elements 35 are incorporated in the coagulating/incising forceps 102 as mentioned in conjunction with FIG. 31.

When the heating elements 135 exhibit resistance values that fall within the normal range, the heating elements 135 are normal. In this case, the number-of-elements identifying unit 151, state-of-element detecting units 152, forceps error judging unit 157, and control unit 158 operates as listed in Table 4.

TABLE 4

| Element | Number-of-elements identifying unit | State-of-element detecting unit | Forceps error judging unit | Control unit |
|---|---|---|---|---|
| A | Present | Normal resistance | Normal, Power supplied | Enabling power supply |
| B | Present | Normal resistance | Normal, Power supplied | |
| C | Present | Normal resistance | Normal, Power supplied | |
| D | Absent | Disconnected or unconnected | Normal, Power not supplied | |

The number-of-elements identifier 142 that indicates the number of heating elements of 3 is, as mentioned above, incorporated in the connector 105. As listed in Table 1, the number-of-elements identifying unit 151 recognizes the presence of the heating elements A, B, and C, recognizes the absence of the heading element D, and thus recognizes that the number of heating elements is 3.

Among the state-of-element detecting units 152, the state-of-element detecting units 152a to 152c recognize that the resistance values exhibited by the associated heating elements are normal, but the state-of-element detecting unit 152d recognizes that the associated heating element D is disconnected or unconnected. On this stage, the number-of-elements identifying unit 151 recognizes that the heating element D is absent. The state-of-element detecting unit 152d recognizes that the heating element D is disconnected or unconnected. Both the results of detection provided by the number-of-elements identifying unit 151 and state-of-element detecting unit 152d agree with each other. Consequently, the forceps error judging unit 157 judges that the coagulating/incising forceps 102 is normal, and transmits an elements-connected signal, which indicates connection of all the heating elements along the allocated channels, to the control unit 158.

In response to the elements-connected signal that indicates connection of the heating elements along the allocated channels, the control unit 158 puts out the forceps error indicator LED 18a. Moreover, the control unit 158 lights the state-of-element indicator LEDs 123a to 123c out of all the state-of-element indicator LEDs 123, and puts out the state-of-element indicator LED 123d.

At this time, if the standby switch 114 is pressed, the control unit 158 discontinues the standby state and puts out the standby indicator LED 116. The control unit 158 thus establishes an output enabled state. Moreover, if the standby switch 114 is pressed again, the control unit 158 makes a transition to the standby state and lights the standby indicator LED 116. The control unit 158 thus discontinues the output enabled state.

Electrical conduction to the heating elements 135 incorporated in the coagulating/incising forceps 102 is started when the footswitch 106 is stepped on. When the maximum temperature level output switch 107a of the footswitch 106 is stepped on, the control unit 158 selects the maximum temperature level of level 5 irrespective of which temperature level has been selected. The control unit 158 brings only the output units 155a to 155c associated with the heating elements A to C to an output state. Incidentally, the output unit 155d associated with the heating element D that is absent feeds no power.

If the designated temperature level output switch 107b is stepped on, the control unit 158 selects a designated temperature level and brings only the output units 155a to 155c associated with the heating elements A to C to the output state. Incidentally, the output unit 155d associated with the heating element D that is absent feeds no power.

While the output units 155a to 155c are feeding power, the temperature-of-element control units 154 adjust the power so that the temperatures of the associated heating elements will be equal to the temperature values associated with the designated temperature level.

The control unit 158 notifies that power is fed based on a temperature level instructed using either of the two switches of the footswitch 106, that is, either of the maximum temperature level output switch 107a and designated temperature level output switch 107b. Specifically, when power is fed based on the temperature level instructed using the maximum temperature level output switch 107a, the buzzer 119 is sounded continuously and the output indicator LED 117 is lit. In contrast, when power is fed based on the temperature level instructed using the designated temperature level output switch 107b, the buzzer 119 is sounded intermittently and the output indicator LED 117 is flickered. At this time, the buzzer 119 may modulate the frequency of sound.

Moreover, the power error detecting unit 164 monitors the heating elements incorporated in the therapeutic instrument control apparatus 103 to see if any heating element is heated abnormally. If it is sensed that any heating element is heated abnormally, a signal is sent to the control unit 158. The control unit 158 instructs the output units 155a to 155c to stop power feed immediately. At this time, the control unit 158 lights the power error indicator LED 118b and sounds the buzzer 119, thus notifying occurrence of an abnormality. In this case, the control unit 158 autonomously makes a transition to the standby state and lights the standby indicator LED 116.

When an abnormality is resolved, the control unit 158 puts out the power error indicator LED 118b and silences the buzzer 119. When the standby switch 114 is pressed, the standby state is discontinued again. The control unit 158 puts out the standby indicator LED 116.

Next, how to judge that the coagulating/incising forceps 102 has become abnormal will be described in conjunction with Table 5 and Table 6. To begin with, a description will be made in conjunction with Table 5.

TABLE 5

| Element | Number-of-elements identifying unit | State-of-element detecting unit | Forceps error judging unit | Control unit |
| --- | --- | --- | --- | --- |
| A | Present | Normal resistance | Normal, Power supplied | Disabling power supply |
| B | Present | Short-circuit | Abnormal | |
| C | Present | Disconnected or unconnected | Abnormal | |
| D | Absent | Disconnected or unconnected | Normal, Power not supplied | |

As listed in Table 5, the number-of-elements identifying unit 151 recognizes the presence of three heating elements, that is, the heating elements A, B, and C. However, the state-of-element detecting unit 152a alone recognizes that the resistance value exhibited by the associated heating element is normal, but the state-of-element detecting units 152b to 152d recognize that the resistance values exhibited by the associated heating elements are abnormal. Thus, the meanings of the signal sent from the number-of-elements identifying unit 151 are inconsistent with the meanings of the signals sent from the state-of-element detecting units 152. In this case, the heating element B or C is thought to be broken. The forceps error judging unit 157 judges that an abnormality is present and transmits an error signal to the control unit 158. If even one heating element is detected to be abnormal, the control unit 158 immediately stops power feed to all the heating elements. At the same time, the control unit 158 lights the forceps error indicator LED 118a and sounds the buzzer 119, thus notifying occurrence of an abnormality. The control unit 158 lights the state-of-element indicator LED 123a in green, and lights the state-of-element indicator LEDs 123b and 123c in red. The control unit 158 puts out the state-of-element indicator LED 123d.

Next, a description will be made in conjunction with Table 6.

TABLE 6

| Element | Number-of-elemens identifying unit | State-of-element detecting unit | Forceps error judging unit | Control unit |
| --- | --- | --- | --- | --- |
| A | Present | Normal resistance | Normal, Power supplied | Disabling power supply |
| B | Present | Normal resistance | Normal, Power supplied | |
| C | Absent | Normal resistance | Abnormal | |
| D | Absent | Disconnected or unconnected | Normal, Power not supplied | |

As listed in Table 6, the number-of-elements identifying unit 151 recognizes the presence of two heating elements, that is, the heating elements A and B. However, although the state-of-element detecting units 152a to 152c recognize that the resistance values exhibited by the associated heating elements are normal, the state-of-element detecting unit 152d judges that the associated heating element is disconnected or unconnected. Thus, the meanings of the signal sent from the number-of-elements identifying unit 151 are inconsistent with the meanings of the signals sent from the state-of-element detecting units 152a to 152d. This is presumably attributable to the fact that the number-of-elements identifier 142 has been incorrectly set up, the number-ofelements identifying unit 151 has made an incorrect judgment, or the state-of-element detecting unit 152c has made an incorrect judgment. The forceps error judging unit 157 judges that an abnormality has occurred and transmits an error signal to the control unit 158. As mentioned above, if even one heating element is detected to be abnormal, the control unit 158 immediately stops power feed to all the heating elements. At the same time, the control unit 158 lights the forceps error indicator LED 118a and sounds the buzzer 119, thus notifying occurrence of the abnormality. At this time, the control unit 158 lights the state-of-element indicator LEDs 123a and 123b in green, and lights the state-of-element indicator LED 123c in red. The control unit 158 puts out the state-of-element indicator LED 123d.

Consequently, the medical treatment system 101 in accordance with the present embodiment can detect an abnormality attributable not only to the fact that any heating element 135 is broken but also to the fact that the number-of-elements identifier 142 has been incorrectly set up, the number-of-elements identifying unit 151 has made an incorrect judgment, or the state-of-element detecting unit 152 has made an incorrect judgement. Moreover, when the ability of any of the heating elements 135 incorporated in the coagulating/incising forceps 102 to dissipate heat changes, if even one heating element is detected to be abnormal, the medical treatment system 101 in accordance with the present embodiment disables power feed. This is because it is impossible to predict a change in the capability for coagulation or incision. Thus, the capability for coagulation or incision can be maintained stable.

Consequently, the medical treatment system 101 in accordance with the present embodiment can detect not only the breakage of any heating element 135 but also incorrect recognition made by an abnormal component. Consequently, the medical treatment system 101 can more accurately feed power suitable for the coagulating/incising forceps 102. Moreover, the medical treatment system 101 in accordance with the present embodiment can offer the stable capability for coagulation or incision.

(Seventh Embodiment)

Figure 34:
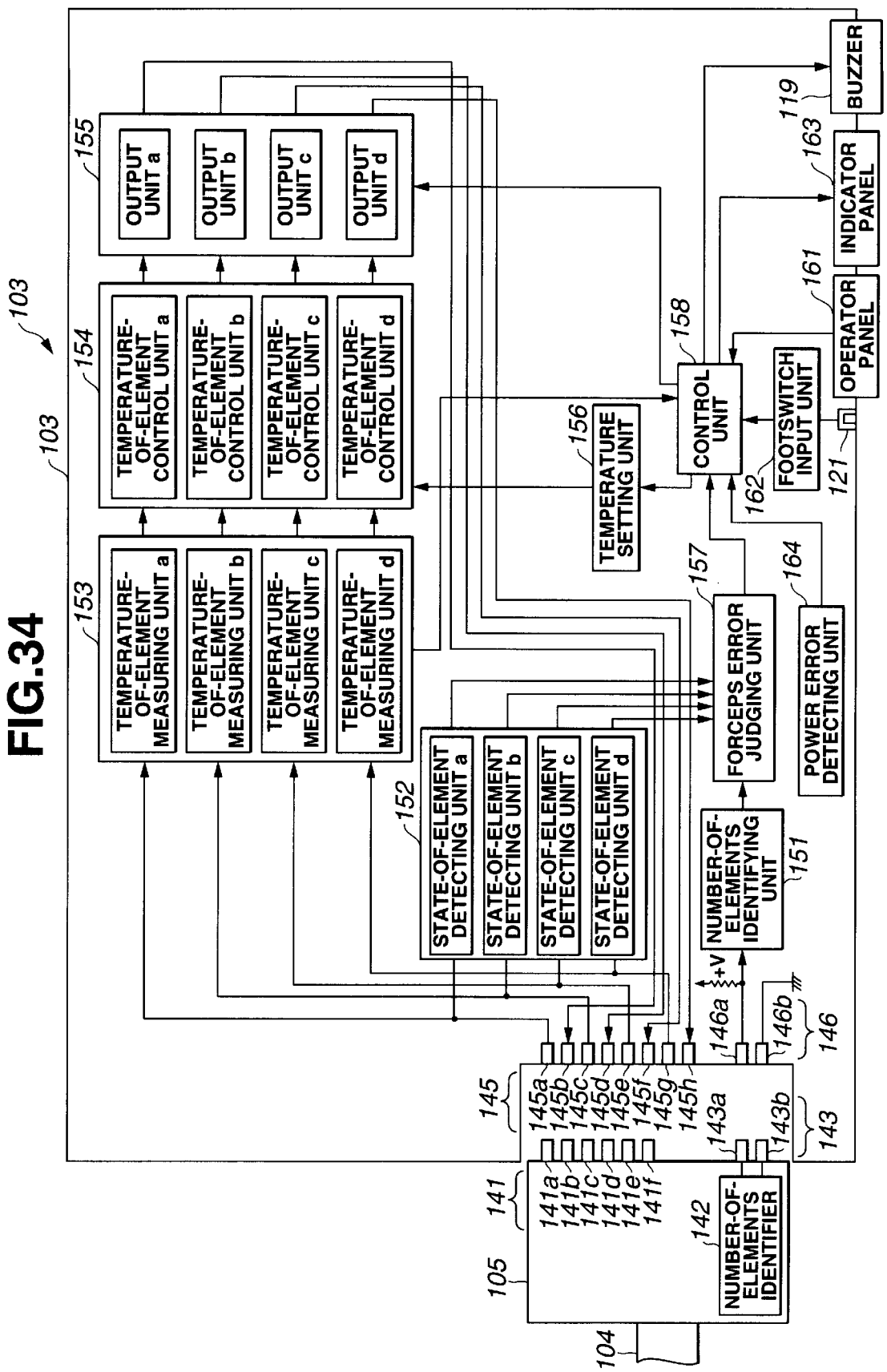
FIG. 34 is a circuit block diagram for explaining a medical treatment system in accordance with a seventh embodiment of the present invention.
Figure 35:
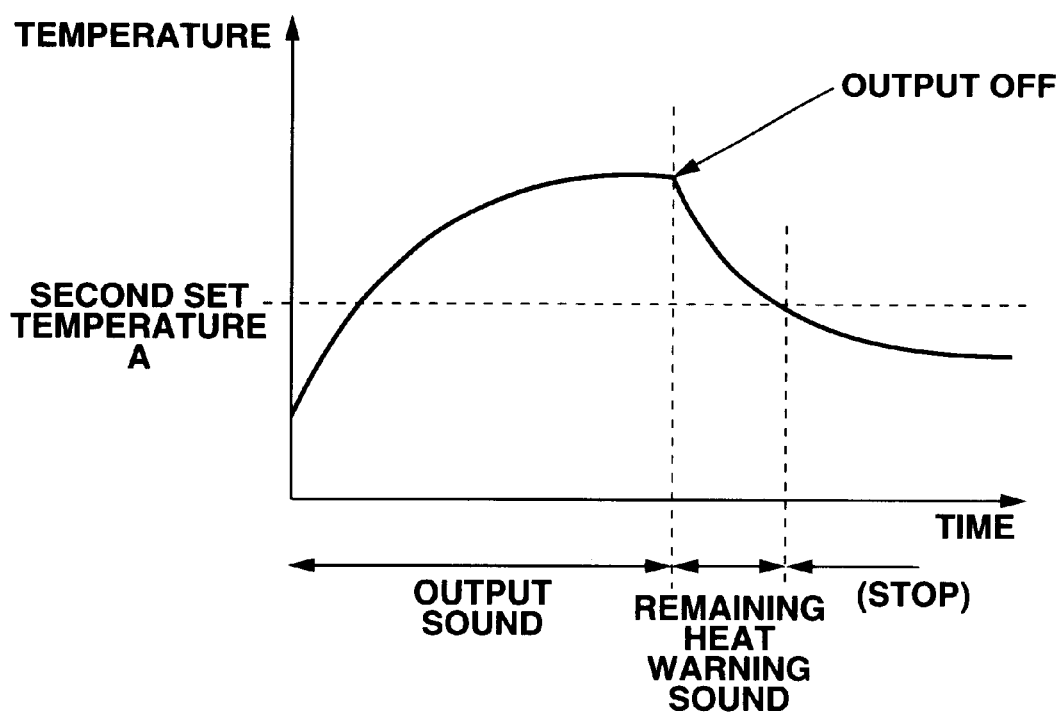
FIG. 35 is a graph for explaining operations to be exerted by the medical treatment system shown in FIG. 34.

FIG. 34 and FIG. 35 are concerned with the seventh embodiment of the present invention. FIG. 34 is a circuit block diagram showing a medical treatment system in accordance with the seventh embodiment of the present invention. FIG. 35 is a graph indicating operations to be exerted by the medical treatment system shown in FIG. 34.

According to the sixth embodiment, when the forceps error judging unit 157 or power error detecting unit 164 judges or detects occurrence of an abnormality, the control unit 158 allows the buzzer 119 to radiate a warning sound. According to the seventh embodiment, the buzzer 119 is designed to radiate a heating warning sound until the temperature of any heating element 135 decreases below a temperature value stored in advance in the control unit 158. The other features are identical to those of the sixth embodiment, and the description of the identical features is omitted. Moreover, the same reference numerals are assigned to components identical to those of the sixth embodiment.

As shown in FIG. 34, a medical treatment system 170 has the temperature-of-element measuring units 153 connected to the control unit 158. The temperature values of the heating elements 135 measured by the temperature-of-element measuring units 153 are received by the control unit 158.

The control unit 158 has a second set temperature level stored in a memory thereof. The second set temperature level is associated with specific values which the temperatures of the heating elements 135 assume before reaching predetermined temperatures after power feed is stopped. The second set temperature level is entered using the operator panel 161.

After power feed is stopped, the control unit 158 controls the buzzer 119 until the temperature values of the heating elements 135 measured by the temperature-of-element measuring units 153 decrease to the values associated with the second set temperature level. Namely, the buzzer 119 is controlled to radiate a heating warning sound.

Operations to be exerted by the medical treatment system 170 having the foregoing components will be described in conjunction with FIG. 35.

FIG. 35 shows the time-sequential change in the temperatures of the heating elements 135 occurring after the therapeutic instrument control apparatus 103 starts feeding power.

After power feed is started, the temperatures of the heating elements 135 start rising and remain constant at set temperature values. After power feed is stopped, the temperatures of the heating elements 135 gradually decrease. After power feed is stopped, the control unit 158 instructs the buzzer 119 to radiate a heating warning sound until the temperature values of the heating elements measured by the temperature-of-element measuring units 153 decrease to the temperature values associated with the predetermined second set temperature level A, for example, 80° C. or less.

Consequently, the medical treatment system 170 in accordance with the seventh embodiment not only provides the same advantages as the sixth embodiment but also notifies that the temperature of the heating treatment member is still high after the completion of treatment.

(Eighth Embodiment)

Figure 36:
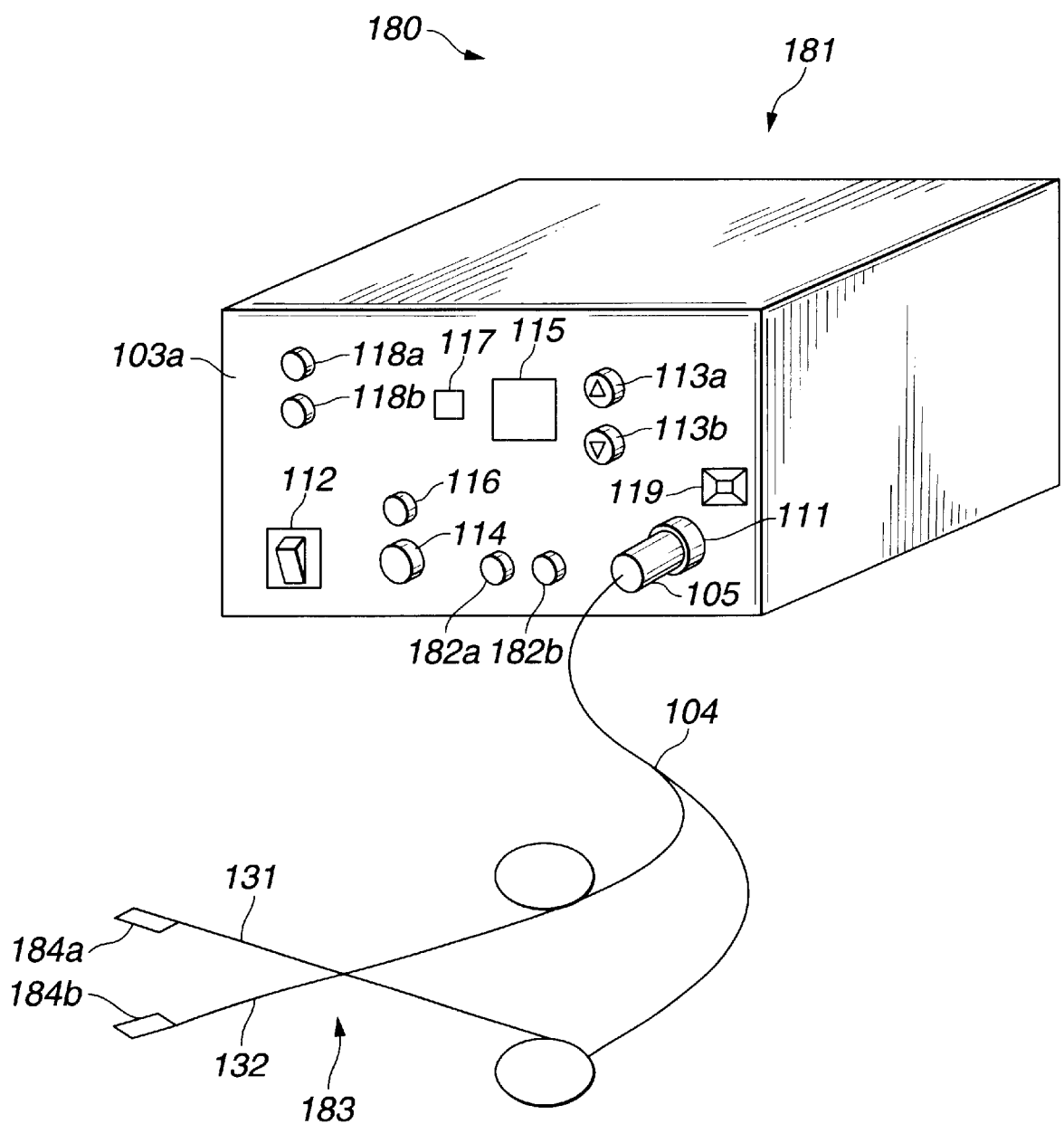
FIG. 36 shows the overall configuration of a medical treatment system in accordance with an eighth embodiment of the present invention.
Figure 37:
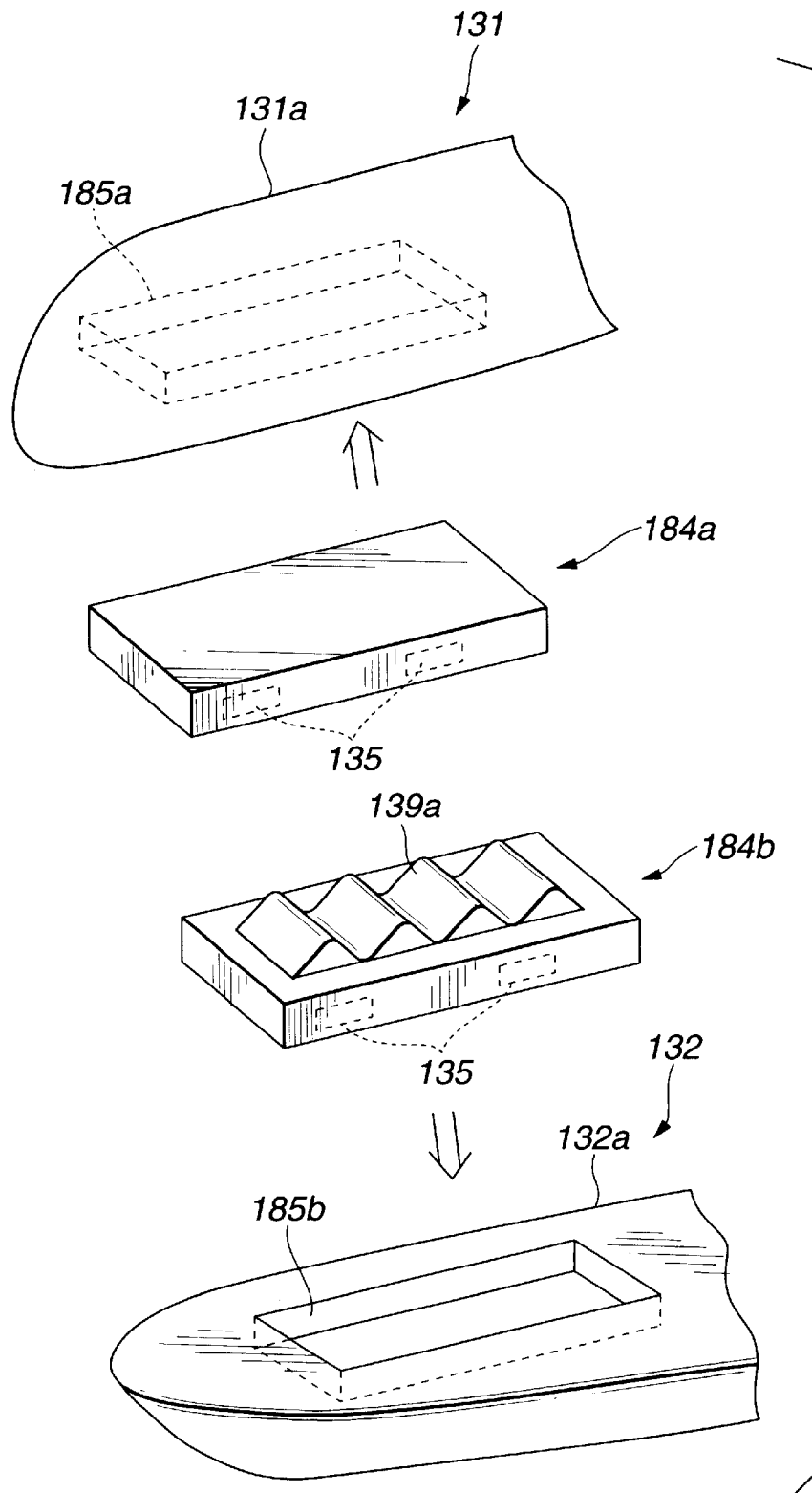
FIG. 37 is an explanatory diagram showing a clamping pair of a therapeutic instrument included in the medical treatment system shown in FIG. 36 and heating treatment members thereof.

FIG. 36 and FIG. 37 are concerned with an eighth embodiment of the present invention. FIG. 36 shows the overall configuration of a medical treatment system in accordance with the eighth embodiment of the present invention. FIG. 37 is an explanatory diagram showing a clamping pair that is a treatment unit and that is included in the medical treatment system shown in FIG. 36 and a heating treatment member included in the clamping pair.

According to the sixth and seventh embodiments, the coagulating/incising forceps 102 in which the heating elements 135 are incorporated is used to construct the medical treatment system. According to the eighth embodiment, coagulating/incising forceps whose heating treatment member having the heating elements 135 incorporated therein is freely attachable and detachable is used to construct the medical treatment system. The other components are identical to those of the sixth embodiment, and the description of the components is omitted. The same reference numerals are assigned to components identical to those of the sixth embodiment.

As shown in FIG. 36, a medical treatment system 180 in accordance with the eighth embodiment has heating treatment member error indicator LEDs 182a and 182b exposed on a front panel 103a of a therapeutic instrument control apparatus 181. Coagulating/incising forceps 183 has heating treatment members 184a and 184b, which are freely detachable, attached to both ends of a claming pair. The heating treatment members 184a and 184b are associated with the heating treatment member error indicator LEDs 182a and 182b exposed on the therapeutic instrument control apparatus 181.

As shown in FIG. 37, the heating treatment member 184a has the heating elements 135 incorporated therein. The heating treatment member 184a is fitted in a storage recess 185a of a stationary blade body 131a so that the heating treatment member can be removed freely. The heating treatment member 184a has connectors, which are not shown and connected to the incorporated heating elements 135, exposed on an outer surface thereof. The connectors are joined to connector receptacles that are not shown and exposed on an inner wall of the storage recess 185a of the stationary blade body 131a. Similarly, the heating treatment member 184b has the heating elements 135 incorporated therein and is fitted in a storage recess 185b of a movable blade body 132a so that the heating treatment member can be removed freely. The heating treatment member 184b has connectors, which are not shown and connected to the incorporated heating elements 135, exposed on an outer surface thereof. The connectors are joined to connector receptacles that are not shown and exposed on an inner wall of the storage recess 185b of the movable blade body 132a. The heating treatment member 184b has a sawtooth 139a formed on the top thereof.

Operations to be exerted by the medical treatment system 180 having the foregoing components will be described below.

To begin with, the heating treatment member 184a is fitted in the storage recess 185a of the stationary blade body 131a, and the heating treatment member 184b is fitted in the storage recess 185b of the movable blade body 132a. At this time, the connectors are joined to the connector receptacles. The connector 105 attached to the end of the cable extending from the coagulating/incising forceps 183 is joined to the connector receptacle 111 exposed on the therapeutic instrument control apparatus 181. Consequently, the heating elements 135 incorporated in the heating treatment members 184a and 184b are connected to the therapeutic instrument control apparatus 181.

The heating elements 135 incorporated in the heating treatment members 184a and 184b are driven and controlled as mentioned in conjunction with FIG. 33.

Assume that the state-of-element detecting units 152 detect that the resistance values exhibited by the heating elements incorporated in the heating treatment member 184a or 184b have exceeded a range of normal values (see FIG. 33). In this case, the forceps error judging unit 157 judges that the heating treatment member 184a or 184b is broken. The forceps error judging unit 157 then transmits an error signal to the control unit 158. In turn, the control unit 158 lights the forceps error indicator LED 118a and sounds the buzzer 119, thus notifying occurrence of an abnormality. At this time, the control unit 158 lights the heating member error indicator LED 182a or 182b associated with the broken heating treatment member so as to notify whichever of the heating treatment members 184a and 184b has been broken. With this indication, a user becomes aware of the heating treatment member that should be replaced with a new one. The user then replaces the broken heating treatment member alone with a new one and reuses the coagulating/incising forceps.

Consequently, the medical treatment system 180 in accordance with the eighth embodiment indicates a heating treatment member that is broken. The broken heating treatment member can therefore be readily replaced with a new one. The medical treatment system 180 can be continuously used.

As described so far, according to the present invention, there are provided a medical treatment system capable of accurately judging the type of therapeutic instrument and feeding power, a therapeutic instrument, and a therapeutic instrument control apparatus.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A heating treatment system or treating a living tissue comprising:
    a therapeutic instrument having a plurality of heating elements, which generate heat based on fed driving power, the therapeutic instrument further having a heat transfer plate that includes a first surface for contact with the living tissue, and a second surface, other than the first surface and coupled to said heating elements, said second surface not coming into contact with the living tissue;
    a temperature level switch used to input an instruction for adjusting the temperature of said heat transfer plate;
    a temperature-of-heating element setting circuit for setting temperature values, to which said plurality of heating elements should be heated, according to the instruction given using said temperature level switch; and
    a plurality of output circuits for feeding driving power to said heating elements according to the plurality of temperature values to which said heating elements should be heated and which are set by said temperature-of-heating element setting circuit.

2. The heating treatment system according to claim 1, wherein said plurality of heating elements are included in one heater block.

3. The heating treatment system according to claim 1, wherein said temperature-of-heating element setting circuit has sets of temperature values, to which said heating elements should be heated, stored in a memory thereof in association with the types of therapeutic instruments.

4. The heating treatment system according to claim 3, wherein the type of therapeutic instrument is identified based on identification information of said therapeutic instrument.

5. The heating treatment system according to claim 1, wherein said temperature-of-heating element setting circuit re-sets the temperature values, to which said heating elements should be heated, after a predetermined time has elapsed since the start of feeding the driving power.

6. The heating treatment system according to claim 5, wherein during the re-setting, the temperature values to which said plurality of heating elements should be heated are re-set to the same value.

7. The heating treatment system according to claim 1, further comprising a control unit for controlling power feed from said output circuits according to a difference in temperature between one of said heating elements and the other heating elements.

8. The heating treatment system according to claim 1, further comprising a control unit for controlling power feed from said output circuits according to changes in the temperatures of said heating elements occurring during a predetermined time.

9. The heating treatment system according to claim 4, further comprising a number-of-heating elements identifying unit for identifying the number of heating elements according to the identified type of therapeutic instrument, a state-of-heating element detecting unit for detecting the states of said heating elements, and a control unit for controlling power feed from said output circuits according to the result of identification provided by said number-of-heating elements identifying unit and the result of detection provided by said state-of-heating element detecting unit.

10. A heating treatment system for treating a living tissue comprising:
- a therapeutic instrument having a heat transfer plate including a first surface in contact with the living tissue and a second surface not in contact with the living tissue;
- a plurality of heating elements for generating heat based on fed driving power, each of the heating elements coupled to the second surface of the heat transfer plate such as to be arranged in a longitudinal direction of the heat transfer plate;
- a temperature level switch used to designate a temperature level associated with temperature values of the plurality of heating elements
- a temperature-of-heating element setting circuit for setting the temperature values, to which said heating elements should be heated, according to the temperature level designated using said temperature level switch; and
- a plurality of output circuits for feeding driving power to said heating elements according to the plurality of temperature values to which said heating elements should be heated and which are set by said temperature-of-heating element setting circuit.

11. The heating treatment system according to claim 10, wherein said temperature-of-heating element setting circuit has sets of temperature values, to which said heating elements should be heated, stored in a memory thereof in association with the types of therapeutic instruments.

12. The heating treatment system according to claim 11, further comprising an identifying unit that identifies the type of therapeutic instrument according to identification information of said therapeutic instrument, and a control unit that controls power feed from said output circuits using the temperature values, to which said heating elements should be heated, according to the result of identification provided by said identifying unit.

13. The heating treatment system according to claim 10, wherein said temperature-of-heating element setting circuit re-sets the temperature values, to which said heating elements should be heated, to the same value after a predetermined time has elapsed since the start of feeding the driving power.

14. The heating treatment system according to claim 10, further comprising a temperature measuring circuit that measures the temperatures of said plurality of heating elements, and a control unit that controls power feed from said output circuits according to a difference in temperature between one of said heating elements and the other heating elements or changes in the temperatures of said heating elements occurring during a predetermined time.

15. The heating treatment system according to claim 14, wherein said control unit controls power feed from said output circuits by stopping or restricting power feed to a heating element whose difference in temperature from the other heating elements or whose change in temperature is equal to or larger than a predetermined value.

16. The heating treatment system according to claim 15, wherein when a difference in temperature equal to or larger than the predetermined value does not occur between one of said plurality of heating elements incorporated in said therapeutic instrument and the other heating elements, if an average of the temperatures of said plurality of heating elements is equal to or larger than a predetermined set value, said control unit stops or restricts power supply to all the heating elements.

17. The heating treatment system according to claim 15, wherein when a change in temperature equal to or larger than the predetermined value does not occur in any of said heating elements included in said therapeutic instrument, if an average of the temperature changes of said plurality of heating elements is equal to or larger than a predetermined set value, said control unit stops or restricts power feed to all the heating elements.

18. The heating treatment system according to claim 10, further comprising a temperature measuring circuit that measures the temperatures of said plurality of heating elements, and a control unit that compares the measured temperature values with a predetermined temperature value and controls power feed from an output circuit to a heating element whose temperature has reached the predetermined temperature value.

19. The heating treatment system according to claim 10, further comprising a number-of-heating elements identifying unit that identifies the number of heating elements according to the identified type of therapeutic instrument, a state-of-heating element detecting unit that detects the states of said heating elements, and a control unit that controls power feed from said output circuits according to the result of identification provided by said number-of-heating elements identifying unit and the result of detection provided by said state-of-heating element detecting unit.

20. The heating treatment system according to claim 19, wherein even when only one of said plurality of heating elements is judged to be abnormal, said control unit stops power feed to all the heating elements.

* * * * *